United States Patent
Pijnappel et al.

(10) Patent No.: US 11,352,605 B2
(45) Date of Patent: Jun. 7, 2022

(54) METHOD FOR CULTURING MYOGENIC CELLS, CULTURES OBTAINED THEREFROM, SCREENING METHODS, AND CELL CULTURE MEDIUM

(71) Applicant: Erasmus University Medical Center Rotterdam, Rotterdam (NL)

(72) Inventors: Wilhelmus Wenceslaus Matthias Pijnappel, Vleuten (NL); Antje Tjitske van der Ploeg, Poortugaal (NL); Erik van der Wal, Schiedam (NL)

(73) Assignee: Erasmus University Medical Center Rotterdam, Rotterdam (NL)

( * ) Notice: Subject to any disclaimer, the term of this patent is extended or adjusted under 35 U.S.C. 154(b) by 589 days.

(21) Appl. No.: 16/300,869

(22) PCT Filed: May 12, 2017

(86) PCT No.: PCT/NL2017/050298
§ 371 (c)(1),
(2) Date: Nov. 12, 2018

(87) PCT Pub. No.: WO2017/196175
PCT Pub. Date: Nov. 16, 2017

(65) Prior Publication Data
US 2019/0161733 A1    May 30, 2019

(30) Foreign Application Priority Data

May 12, 2016    (EP) .................................... 16169396

(51) Int. Cl.
| | | |
|---|---|---|
| *C12N 5/077* | (2010.01) | |
| *C12N 5/074* | (2010.01) | |
| *C12N 5/00* | (2006.01) | |
| *C12Q 1/02* | (2006.01) | |

(52) U.S. Cl.
CPC ......... *C12N 5/0658* (2013.01); *C12N 5/0018* (2013.01); *C12N 5/0659* (2013.01); *C12N 5/0696* (2013.01); *C12Q 1/025* (2013.01); *C12N 2501/115* (2013.01); *C12N 2501/15* (2013.01); *C12N 2501/602* (2013.01); *C12N 2501/603* (2013.01); *C12N 2501/604* (2013.01); *C12N 2501/606* (2013.01); *C12N 2501/727* (2013.01); *C12N 2506/1307* (2013.01); *C12N 2506/45* (2013.01); *C12N 2533/54* (2013.01); *C12N 2533/90* (2013.01)

(58) Field of Classification Search
CPC ........................... C12N 5/0658; C12N 5/0696
See application file for complete search history.

(56) References Cited

U.S. PATENT DOCUMENTS

2015/0299659 A1    10/2015    Barberi et al.

OTHER PUBLICATIONS

Zammit (Journal of Cell Science, 119: 1824-1832).*
Shelton (2014, Stem Cell Reports, 3:516-529).*
Kim (2013, Sem Cell Res Ther, 4:147, pp. 1-11).*
Borcin et al., "Derivation and FACS-Mediated Purification of PAX3+/PAX7+ Skeletal Muscle Precursors from Human Pluripotent Stem Cells," Stem Cell Reports 1:620-631, 2013.
Clegg, Christopher H., et al. "Growth Factor Control of Skeletal Muscle Differentiation: Commitment to Terminal Differentiation Occurs in G1 Phase and is Repressed by Fibroblast Growth Factor" The Journal of Cell Biology, vol. 105, No. 2, pp. 949-956, Aug. 1, 1987.
Halevy, Oma, et al. "Pattern of Pax7 Expression During Myogenesis in the Posthatch Chicken Establishes a Model for Satellite Cell Differentiation and Renewal" Developmental Dynamics, vol. 231, No. 3, pp. 489-502, Nov. 1, 2004.
International Search Report and Written Opinion dated Aug. 7, 2017 in International (PCT) Application No. PCT/NL2017/050298 (13 pages).
Le Grand, Fabien, et al. "Skeletal muscle satellite cells and adult myogenesis" Current Opinion in Cell Biology, vol. 19, No. 6, pp. 628-633, Dec. 1, 2007.
Sarig, Rachel, et al. "Regeneration and Transdifferentiation Potential of Muscle-Derived Stem Cells Propagated as Myospheres" Stem cells, vol. 24, No. 7, pp. 1769-1778, Jul. 1, 2006.
Van Der Wal, Erik, et al. "GAA Deficiency in Pompe Disease is Alleviated by Exon Inclusion in iPSC-Derived Skeletal Muscle Cells" Molecular Therapy-Nucleic Acids, vol. 7, pp. 101-115, Jun. 16, 2017.

* cited by examiner

*Primary Examiner* — Valarie E Bertoglio
(74) *Attorney, Agent, or Firm* — Dentons US LLP

(57) ABSTRACT

The invention is in the field of cell culturing. More specifically, it is in the field of generating and expanding myogenic cells from induced pluripotent stem (i PS) cells. The invention relates inter alia to cells generated and expanded via such a method, a growth medium specifically suited for the purpose of expanding isolated myogenic cells, and methods for screening compounds on cell structures such as myotubes and myofibers.

16 Claims, 33 Drawing Sheets

Specification includes a Sequence Listing.

B)

C)

A)

B)

C)

F)

D)

E)

SEQUENCE LISTING

```
<160> NUMBER OF SEQ ID NOS: 34

<210> SEQ ID NO 1
<211> LENGTH: 19
<212> TYPE: DNA
<213> ORGANISM: Artificial Sequence
<220> FEATURE:
<223> OTHER INFORMATION: primer

<400> SEQUENCE: 1
aaccgcgaga agatgaccc                                                  19

<210> SEQ ID NO 2
<211> LENGTH: 21
<212> TYPE: DNA
<213> ORGANISM: Artificial Sequence
<220> FEATURE:
<223> OTHER INFORMATION: primer

<400> SEQUENCE: 2
gccagaggcg tacagggata g                                               21

<210> SEQ ID NO 3
<211> LENGTH: 18
<212> TYPE: DNA
<213> ORGANISM: Artificial Sequence
<220> FEATURE:
<223> OTHER INFORMATION: primer

<400> SEQUENCE: 3
aaactgaggc acggagcg                                                   18

<210> SEQ ID NO 4
<211> LENGTH: 18
<212> TYPE: DNA
<213> ORGANISM: Artificial Sequence
<220> FEATURE:
<223> OTHER INFORMATION: primer

<400> SEQUENCE: 4
gagtgcagcg gttgccaa                                                   18
```

<210> SEQ ID NO 5
<211> LENGTH: 16
<212> TYPE: DNA
<213> ORGANISM: Artificial Sequence
<220> FEATURE:
<223> OTHER INFORMATION: primer

<400> SEQUENCE: 5
ggcacggagc gggaca                                                    16

<210> SEQ ID NO 6
<211> LENGTH: 24
<212> TYPE: DNA
<213> ORGANISM: Artificial Sequence
<220> FEATURE:
<223> OTHER INFORMATION: primer

<400> SEQUENCE: 6
ctgttagctg gatctttgat cgtg                                           24

<210> SEQ ID NO 7
<211> LENGTH: 17
<212> TYPE: DNA
<213> ORGANISM: Artificial Sequence
<220> FEATURE:
<223> OTHER INFORMATION: primer

<400> SEQUENCE: 7
aggcacggag cggatca                                                   17

<210> SEQ ID NO 8
<211> LENGTH: 20
<212> TYPE: DNA
<213> ORGANISM: Artificial Sequence
<220> FEATURE:
<223> OTHER INFORMATION: primer

<400> SEQUENCE: 8
tcggagaact ccacgctgta                                                20

<210> SEQ ID NO 9
<211> LENGTH: 20
<212> TYPE: DNA
<213> ORGANISM: Artificial Sequence
<220> FEATURE:
<223> OTHER INFORMATION: primer

<400> SEQUENCE: 9
cactccggtc ccaaatgtag                                                20

<210> SEQ ID NO 10
<211> LENGTH: 20
<212> TYPE: DNA
<213> ORGANISM: Artificial Sequence
<220> FEATURE:
<223> OTHER INFORMATION: primer

<400> SEQUENCE: 10
ttccctgtag caccacacac                                                20

<210> SEQ ID NO 11
<211> LENGTH: 20
<212> TYPE: DNA
<213> ORGANISM: Artificial Sequence
<220> FEATURE:

```
<223> OTHER INFORMATION: primer

<400> SEQUENCE: 11
cactccctca cctccatcgt                                              20

<210> SEQ ID NO 12
<211> LENGTH: 19
<212> TYPE: DNA
<213> ORGANISM: Artificial Sequence
<220> FEATURE:
<223> OTHER INFORMATION: primer

<400> SEQUENCE: 12
catctgggaa ggccacaga                                               19

<210> SEQ ID NO 13
<211> LENGTH: 20
<212> TYPE: DNA
<213> ORGANISM: Artificial Sequence
<220> FEATURE:
<223> OTHER INFORMATION: primer

<400> SEQUENCE: 13
gtgttagtgg cacccaggtc                                              20

<210> SEQ ID NO 14
<211> LENGTH: 20
<212> TYPE: DNA
<213> ORGANISM: Artificial Sequence
<220> FEATURE:
<223> OTHER INFORMATION: primer

<400> SEQUENCE: 14
ggaaggcctg tcttgttcac                                              20

<210> SEQ ID NO 15
<211> LENGTH: 20
<212> TYPE: DNA
<213> ORGANISM: Artificial Sequence
<220> FEATURE:
<223> OTHER INFORMATION: primer

<400> SEQUENCE: 15
cctggattgc gaattttacc                                              20

<210> SEQ ID NO 16
<211> LENGTH: 20
<212> TYPE: DNA
<213> ORGANISM: Artificial Sequence
<220> FEATURE:
<223> OTHER INFORMATION: primer

<400> SEQUENCE: 16
atggaattct gatggccaaa                                              20

<210> SEQ ID NO 17
<211> LENGTH: 38
<212> TYPE: DNA
<213> ORGANISM: Artificial Sequence
<220> FEATURE:
<223> OTHER INFORMATION: primer

<400> SEQUENCE: 17
gctcttttag aattttggga gcaggttttc tgacttcg                          38
```

```
<210> SEQ ID NO 18
<211> LENGTH: 38
<212> TYPE: DNA
<213> ORGANISM: Artificial Sequence
<220> FEATURE:
<223> OTHER INFORMATION: primer

<400> SEQUENCE: 18
cgaagtcaga aaacctgctc caaaaattct aaaagagc                           38

<210> SEQ ID NO 19
<211> LENGTH: 37
<212> TYPE: DNA
<213> ORGANISM: Artificial Sequence
<220> FEATURE:
<223> OTHER INFORMATION: primer

<400> SEQUENCE: 19
cctggctcgc tacagatgca taggaggacg gaggacg                            37

<210> SEQ ID NO 20
<211> LENGTH: 37
<212> TYPE: DNA
<213> ORGANISM: Artificial Sequence
<220> FEATURE:
<223> OTHER INFORMATION: primer

<400> SEQUENCE: 20
cgtcctccgt cctcctatgc atctgtagcg agccagg                            37

<210> SEQ ID NO 21
<211> LENGTH: 17
<212> TYPE: DNA
<213> ORGANISM: Artificial Sequence
<220> FEATURE:
<223> OTHER INFORMATION: primer

<400> SEQUENCE: 21
gtaaaacgac gggccag                                                  17

<210> SEQ ID NO 22
<211> LENGTH: 17
<212> TYPE: DNA
<213> ORGANISM: Artificial Sequence
<220> FEATURE:
<223> OTHER INFORMATION: primer

<400> SEQUENCE: 22
caggaaacag ctatgac                                                  17

<210> SEQ ID NO 23
<211> LENGTH: 27
<212> TYPE: DNA
<213> ORGANISM: Artificial Sequence
<220> FEATURE:
<223> OTHER INFORMATION: primer

<400> SEQUENCE: 23
aggttctcct cgtccgcccg ttgttca                                       27

<210> SEQ ID NO 24
<211> LENGTH: 27
<212> TYPE: DNA
<213> ORGANISM: Artificial Sequence
<220> FEATURE:
<223> OTHER INFORMATION: primer
```

```
<400> SEQUENCE: 24
tccaagggca cctcgtagcg cctgtta                                          27

<210> SEQ ID NO 25
<211> LENGTH: 29
<212> TYPE: DNA
<213> ORGANISM: Artificial Sequence
<220> FEATURE:
<223> OTHER INFORMATION: primer

<400> SEQUENCE: 25
gcgcctgcag taacaacata ggagctgtg                                        29

<210> SEQ ID NO 26
<211> LENGTH: 30
<212> TYPE: DNA
<213> ORGANISM: Artificial Sequence
<220> FEATURE:
<223> OTHER INFORMATION: primer

<400> SEQUENCE: 26
gcgcgtcgac cagatacgcg tttcctagga                                       30

<210> SEQ ID NO 27
<211> LENGTH: 70
<212> TYPE: DNA
<213> ORGANISM: Artificial Sequence
<220> FEATURE:
<223> OTHER INFORMATION: GAA pre-mRNA

<400> SEQUENCE: 27
gcagactgtg caagtgctct gcactcccct gctggagctt ttctcgccct tccttctggc      60
cctctcccca                                                             70

<210> SEQ ID NO 28
<211> LENGTH: 20
<212> TYPE: DNA
<213> ORGANISM: Artificial Sequence
<220> FEATURE:
<223> OTHER INFORMATION: CypA 1

<400> SEQUENCE: 28
tgtaccctta ccactcagtc                                                  20

<210> SEQ ID NO 29
<211> LENGTH: 25
<212> TYPE: DNA
<213> ORGANISM: Artificial Sequence
<220> FEATURE:
<223> OTHER INFORMATION: CypA 2

<400> SEQUENCE: 29
catgttgtac ccttaccact cagtc                                            25

<210> SEQ ID NO 30
<211> LENGTH: 20
<212> TYPE: DNA
<213> ORGANISM: Artificial Sequence
<220> FEATURE:
<223> OTHER INFORMATION: AON 1

<400> SEQUENCE: 30
gagtgcagag cacttgcaca                                                  20
```

```
<210> SEQ ID NO 31
<211> LENGTH: 25
<212> TYPE: DNA
<213> ORGANISM: Artificial Sequence
<220> FEATURE:
<223> OTHER INFORMATION: AON 2

<400> SEQUENCE: 31
gagtgcagag cacttgcaca gtctg                                        25

<210> SEQ ID NO 32
<211> LENGTH: 21
<212> TYPE: DNA
<213> ORGANISM: Artificial Sequence
<220> FEATURE:
<223> OTHER INFORMATION: AON 3

<400> SEQUENCE: 32
ccagaaggaa gggcgagaaa a                                            21

<210> SEQ ID NO 33
<211> LENGTH: 25
<212> TYPE: DNA
<213> ORGANISM: Artificial Sequence
<220> FEATURE:
<223> OTHER INFORMATION: AON 4

<400> SEQUENCE: 33
gccagaagga agggcgagaa aagct                                        25

<210> SEQ ID NO 34
<211> LENGTH: 60
<212> TYPE: DNA
<213> ORGANISM: Artificial Sequence
<220> FEATURE:
<223> OTHER INFORMATION: donor splice site of CypA exon 4

<400> SEQUENCE: 34
tttttcatct gcactgccaa gactgagtgg taagggtaca acatggcaca ctaaccacct  60
```

METHOD FOR CULTURING MYOGENIC CELLS, CULTURES OBTAINED THEREFROM, SCREENING METHODS, AND CELL CULTURE MEDIUM

FIELD OF THE INVENTION

The invention is in the field of cell culturing. More specifically, it is in the field of generating and expanding myogenic cells from induced pluripotent stem (iPS) cells. The invention relates inter alia to cells generated and expanded via such methods, to growth media specifically suited for the purpose of expanding isolated myogenic cells, and methods for in vitro screening and selection of therapeutically active or diagnostic compounds on cell structures such as myotubes and myofibers generated from expanded myogenic cells.

BACKGROUND OF THE INVENTION

Although more than 700 human disorders that affect skeletal muscle are known, very few therapies for skeletal muscle disorders have been developed. Notable exceptions are enzyme therapy for Pompe disease and exon skipping for Duchenne Muscular Dystrophy (DMD), which is based on blocking of canonical splice sites of DMD pre-mRNA using antisense oligonucleotides (AONs). AON-mediated therapy has also been successfully applied in animal models for a number of other diseases including Spinal Muscular Atrophy (SMA), type I Usher syndrome, and Hutchinson-Gilford progeria syndrome.

A muscular disorder in the spotlight is Pompe disease, which is caused by a deficiency of the lysosomal enzyme acid alpha-glucosidase (GAA). Current Enzyme Replacement Therapy (ERT) is only partially effective and very expensive, warranting the search for alternatives. A well-defined threshold of 20% residual GAA activity is known, and a small increase in GAA activity is sufficient to revert to a disease-free situation. In Caucasians, the splicing variant c.-13-32T>G (IVS1) is the most common pathogenic GAA variant with a frequency of 90% in adults and 50% in children. This causes skipping of exon 2, but also allows a low level (10-15%) of normal splicing. Exon 2 is the first coding exon, and its skipping results in mRNA degradation and failure to produce GAA protein. Promotion of exon inclusion may be achieved by blocking of a splicing repressor, which is difficult to identify due to the difficulty of reliable in silico prediction of such elements.

A major obstacle for the modeling of human diseases affecting skeletal muscle and the testing of potential drugs in vitro has been the lack of methods for reproducibly obtaining sufficient amounts of pure, preferably patient-derived, differentiated human skeletal muscle cells. It has not been possible to generate large amounts of isolated skeletal muscle cells from pluripotent stem cells, and to test therapies quantitatively. This is one of the major reasons that, as to date, very few therapies have been developed, as these therapies cannot be tested quantitatively in vitro.

Application of induced pluripotent stem (iPS) cells to model human disorders affecting skeletal muscle has been hampered by the difficulty to differentiate pluripotent stem cells into skeletal muscle cells in vitro and to obtain sufficient amounts of pure, patient-derived, differentiated human skeletal muscle cells. Alternatively, transgene overexpression of MyoD or Pax7, which are markers for certain stages of myogenic differentiation, is difficult. We have found that the use of small molecules that activate the WNT pathway to drive stem cell differentiation into the myogenic lineage still generally results in low recoveries of myogenic cells after purification by FACS (typically 250,000 cells from $10^6$ iPS cells) and variable viability and differentiation potential. All this prevents proper quantitative analysis of potential treatments.

It is clear that there is a great need for stem cell culturing conditions that allow for the generation and expansion of human myogenic progenitors derived from pluripotent stem cells of individual subjects. It is an aim of the invention to provide suitable culturing media for expansion of myogenic progenitors and to ultimately provide for (terminally) differentiated and fused myoblasts in the form of multi-nucleated myotube fibers that can be used in treatment or in assays for screening drugs.

SUMMARY OF THE INVENTION

The present inventors have now surprisingly established pluripotent stem cell culturing conditions allowing expansion of individually isolated myogenic cells up to at least about $7 \times 10^6$ fold following their isolation by, for instance, fluorescence activated cell sorting (FACS). It was further unexpectedly found that an expanded cell culture obtained by a method of the invention constitutes a novel class of myogenic cells, which are homogeneous and can be held in culture for a prolonged period of time. These cells are highly expandable when cultured under the appropriate conditions, and retain their ability for terminal differentiation. Using this novel class of cells, it was possible to generate differentiated myogenic tissue structures such as myotubes which ultimately provided for the possibility of quantitative in vitro testing, and discovery, of compounds or compositions that could potentially be of great benefit in the treatment of muscle disease, including such diseases as Pompe disease and other (neuro)muscular disorders. The differentiation conditions applied, such as the differentiation media, allow for the functional maturation of expanded cells of the invention into myotubes and even in more mature myofibers.

The culturing methods presented here enable the large-scale generation of myogenic cells, from, inter alia, iPS cells. Assuming that a drug screen will be performed in 96 wells plates containing 20,000 cells/well, the testing of 10,000 compounds in triplicate would require the seeding of $6 \times 10^8$ myogenic progenitors. This quantity of cells can now easily be attained using the methods presented herein, which are capable of yielding at least $10^{12}$ cells per line. The myogenic cells prepared by methods of the invention offer important advantages over primary human myoblasts preparations, as these latter preparations can be contaminated with fibroblasts and endothelial cells. Moreover, primary human myoblast preparations show a progressive loss of myogenic potential, in terms of both proliferation potential and/or differentiation potential upon successive passaging. The methods and means of the present invention allow for the generation of expanded myogenic progenitor cells that resemble myoblasts in terms of differentiation status, but remain culturable and expandable for prolonged periods of time, and will differentiate into myogenic end-structures under differentiation conditions, thereby overcoming the problems of culturing myoblasts, and the problem of low yields of viable and expandable myogenic cells after isolating by, for instance, FACS. The methods of the present invention allow for the generation of patient-derived cell lines at high cell densities, and their application in personalized medicine.

In a first aspect, the present invention provides an in vitro cell culture comprising a population of expanded myogenic progenitor cells produced by the cultural expansion for at least 1 passage of at least one isolated C-Met+ and Hnk1− myogenic progenitor starting cell, wherein at least 90% of the cells in said population is positive for myogenesis marker MyoD, wherein at least 50% of the cells in said population is negative for myogenesis marker Pax7, said cell culture further comprising a synthetic culture medium.

In a preferred embodiment of an in vitro cell culture of the invention, at least 70%, more preferably at least 90%, of the cells in said population is negative for myogenesis marker Pax7.

In another preferred embodiment of said in vitro cell culture, said population is produced by the cultural expansion of said at least one isolated C-Met+ and Hnk1− myogenic progenitor starting cell for at least 7 passages.

In yet another preferred embodiment of said in vitro cell culture, said at least one isolated C-Met+ and Hnk1− myogenic progenitor starting cell is isolated from a myogenic cell culture produced by culturing a pluripotent stem cell (PSC) in the presence of (i) a Wnt agonist and/or a glycogen synthase kinase 3 beta (GSK3B) inhibitor, and (ii) an FGF pathway activator.

In still another preferred embodiment of said in vitro cell culture, said PSC is an induced PSC (iPSC), preferably an iPSC obtained from a cell of a healthy human subject or a human subject suffering, or suspected of suffering, from a neuromuscular disorder.

In yet another preferred embodiment of said in vitro cell culture, said at least one isolated C-Met+ and Hnk1− myogenic progenitor starting cell is isolated by FACS.

In yet another preferred embodiment of said in vitro cell culture, said culture has a cell count of at least $10^6$, preferably at least $10^9$, more preferably at least $10^{12}$ cells.

In yet another preferred embodiment of said in vitro cell culture, said population of expanded myogenic progenitor cells is homogeneous.

In yet another preferred embodiment of said in vitro cell culture, said synthetic culture medium comprises fetal bovine serum (FBS), preferably in a concentration of about 10%, and an amount of 90-110 ng/ml, more preferably about 100 ng/ml, of FGF2, optionally said synthetic culture medium further comprising synthetic extracellular matrix (ECM) protein, fibrillar Collagen, or a mixture thereof. ECM, mimetics thereof, or other fibrous proteins are suitably used as coating of culture wells or containers. Suitable examples include extracellular matrix (ECM) gel, preferably ECM gel from Engelbreth-Holm-Swarm murine sarcoma fibrillar collagen (E6909 Sigma), and/or preferably a combination of (rat tail) collagen type I and MaxGel ECM (E0282 Sigma), and/or fibrillar collagen, and/or a component of ECM gel, and/or a synthetic mimetic of an ECM component, and/or collagen type I.

In yet another preferred embodiment of said in vitro cell culture, the expanded myogenic progenitor cells in said culture medium are expandable in vitro and inducible to terminal differentiation into myotubes and/or myofibers.

In another aspect, the present invention provides myogenic progenitor cell of a cell culture of the invention as defined above, wherein said myogenic progenitor cell is positive for myogenesis marker MyoD and negative for myogenesis marker Pax7, preferably wherein said cell is isolated.

In certain preferred embodiments of the cell culture of the invention, or the cell of the invention as described above, the culture or cell is frozen or cryopreserved.

In another aspect, the present invention provides a method for producing a cell culture comprising a population of expanded myogenic progenitor cells in a synthetic culture medium, as well as a cell culture comprising a population of expanded myogenic progenitor cells in a synthetic culture medium, obtainable by said method.

The method for producing a cell culture comprising a population of expanded myogenic progenitor cells, in aspects of this invention comprises the steps of:

a) providing a pluripotent stem cell (PSC), preferably an iPSC;

b) culturing said PSC in a synthetic culture medium supporting differentiation of said PSC towards a myogenic cell lineage for (i) a first period of 3-8 days in the presence of between 2-5 microM, preferably about 3.5 microM, of CHIR99021, (ii) a second period of 5-20 days in the presence of 10-30 ng/ml of FGF2; and, optionally, (iii) a third period of 10-20 days in the presence of insulin-transferrin-selenium-ethanolamine (ITS-X), to thereby provide a cell culture of pre-differentiated PSCs comprising myogenic progenitors cells;

c) isolating from said cell culture comprising myogenic progenitors cells at least one C-Met+ and Hnk1− myogenic progenitor starting cell, preferably by FACS, to thereby provide a purified myogenic cell lineage;

d) expanding said at least one isolated C-Met+ and Hnk1− myogenic progenitor starting cell in a synthetic culture medium comprising fetal bovine serum (FBS), preferably in a concentration of about 10% (w/w), and 90-110 ng/ml of FGF2 for at least 1 passage, preferably at least 7 passages, to thereby provide a cell culture comprising a population of expanded C-Met+ and Hnk1− myogenic progenitor cells, wherein at least 50%, preferably at least 90% of said population of expanded C-Met+ and Hnk1− myogenic progenitor cells are myogenesis marker MyoD positive and myogenesis marker Pax7 negative.

In preferred embodiments of aspects of the method of the invention, the step of expanding said at least one C-Met+ and Hnk1− myogenic progenitor starting cell in step d) is performed in a culture medium comprising a ROCK inhibitor during at least the cultivation prior to the first passage, preferably the culture medium base is DMEM-HG.

In another aspect, the present invention provides a myotube or myofiber formed from the cell culture of the invention as described above. Optionally, said myotube or myofiber is formed on a scaffold.

In preferred embodiments of a myotube or myofiber of the present invention said myotube or myofiber has (i) a fusion index of at least 60%, preferably at least 70%, (ii) forms sarcomeres, (iii) expresses neuromuscular junctions, and/or (iv) shows spontaneous contraction in culture.

In another aspect, the present invention provides an in vitro method of screening for a test compound that modulates the function of myogenic cells in a culture of the invention as described, a myotube or myofiber of the invention as described, a cell of the invention as described, or a myogenic cell or cell structure intermediate to said cell and said myotube or myofiber in terms of differentiation status, comprising the step of a) contacting a test compound with a cell culture of the invention as described, a myotube or myofiber of the invention as described, a cell of the invention as described, or a myogenic cell or cell structure intermediate to said cell and said myotube or myofiber in terms of differentiation status;

b) observing a change in the function, phenotype, proteome, transcriptome, or interactome of said cells, cells in said culture, myotube or myofiber, or intermediate, compared to a control compound, and optionally c) selecting said test compound in the case a change is observed in step b) to thereby provide a candidate drug for treating skeletal muscle disorders.

In another aspect, the present invention provides the use of a cell culture of the invention as described, the cell of the invention as described, the myotube or myofiber of the invention as described, or a myogenic cell or cell structure intermediate to said cell and said myotube or myofiber in terms of differentiation status, for the in vitro screening of a test compound or drug.

In another aspect, the present invention provides the medical use of a cell culture of the invention as described, the cell of the invention as described, the myotube or myofiber of the invention as described, or a myogenic cell or cell structure intermediate to said cell and said myotube or myofiber in terms of differentiation status, the cell aspects as thus defined for use in medicine or in the manufacture of a medicament, preferably for use in the treatment of a muscle disorder, preferably wherein the mode of administration of said cell, myotube, myogenic cell or cell structure is by transplantation.

In another aspect, the present invention provides a synthetic culture medium for expanding myogenic progenitor cells, comprising a synthetic base medium, preferably DMEM HG; fetal bovine serum (FBS), preferably in a concentration of about 10%; and 90-110 ng/ml, more preferably about 100 ng/ml, of FGF2.

In preferred embodiments of this synthetic culture medium, the culture medium is for expanding isolated myogenic progenitor cells, preferably myogenic progenitor cells isolated by FACS, and wherein said culture medium further comprises a ROCK inhibitor.

In another aspect, the present invention provides a method for differentiating expanded myogenic progenitor cells into myotubes and/or myofibers, comprising the steps of:

a) plating cells of a cell culture according to the invention as described above on a container or plate for holding cells, wherein said container or plate is preferably coated with (synthetic) extracellular matrix (ECM) protein;

b) culturing the cells in a synthetic culture medium for expanding myogenic progenitor cells as described in the aspect hereinabove, or in a synthetic culture medium comprising DMEM, optionally further comprising an extracellular matrix (ECM) protein and/or PBS;

c) replacing the culture medium of step b) with a differentiation medium comprising, or consisting of, (i) DMEM high glucose, DMEM low glucose, or DMEM/F12, (ii) about 1% of ITS-X and (iii) 0.5%-5%, preferably about 1%, of knock-out serum replacement and/or 0.1-10 mg/ml, preferably about 0.5 mg/ml, of BSA; and d) allowing the cells to form myotubes or myofibers.

As an extracellular matrix (ECM) protein in step a) and/or b), one may use, for instance, extracellular matrix (ECM) gel, preferably ECM gel from Engelbreth-Holm-Swarm murine sarcoma fibrillar collagen (E6909 Sigma), and/or preferably a combination of (rat tail) collagen type I and MaxGel ECM (E0282 Sigma), and/or fibrillar collagen, and/or a component of ECM gel, and/or a synthetic mimetic of an ECM component, and/or collagen type I, or a combination thereof.

In preferred embodiments of this method for differentiating expanded myogenic progenitor cells at least 20%, preferably 30-60%, of said differentiation medium is replaced by fresh differentiation medium every second day.

In another aspect, the present invention provides a synthetic culture medium for differentiating expanded myogenic progenitor cells into myotubes and/or myofibers, comprising, or consisting of (i) DMEM high glucose, DMEM low glucose or DMEM/F12, (ii) about 1% of ITS-X and (iii) 0.5%-5%, preferably about 1%, of knock-out serum replacement and/or 0.1-10 mg/ml, preferably about 0.5 mg/ml, of BSA. In a preferred embodiment of this synthetic culture medium, the medium is supplemented with penicillin, streptomycin and/or glutamine.

Figure 5:
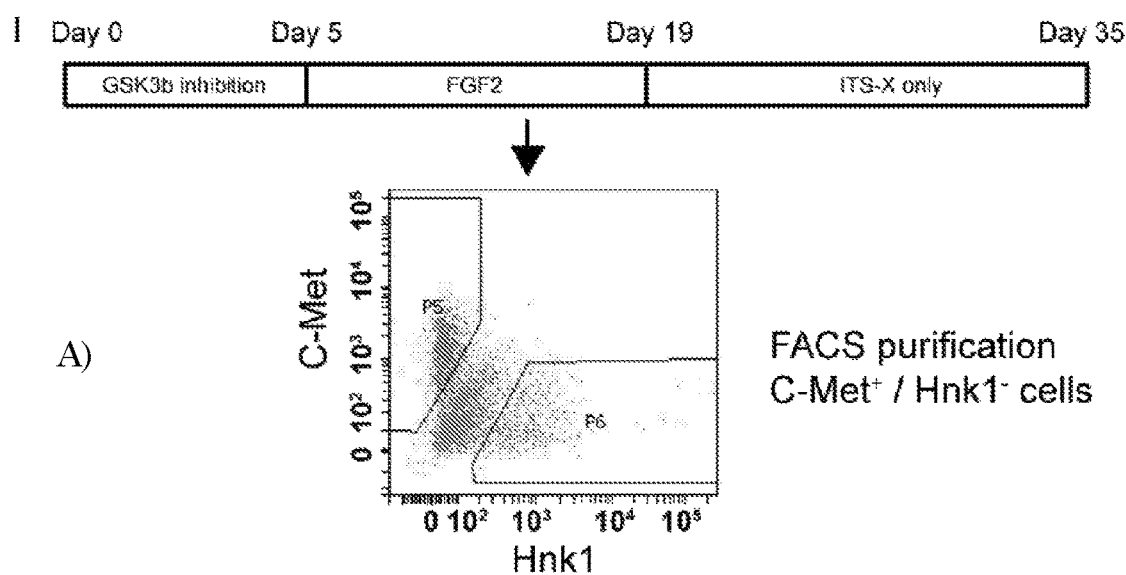
FIG. 5 panel A shows the differentiation protocol used for differentiating the iPS cell lines into myogenic progenitors and shows the selection criteria for the subsequent purification or isolation by FACS. The basal medium for the whole procedure consisted of DMEM/F12, 1% insulin-transferrin-selenium-ethanolamine (ITS-X) and Penicillin/Streptomycin/Glutamine, as detailed in the Examples section. The culturing scheme involved a series of additions to this basal medium as follows: a first period of glycogen synthase kinase 3 beta (GSK3B) inhibition, followed by a second period of culturing in a human basic fibroblast growth factor (FGF2) medium, followed by a third period of culturing in basal medium only. Finally, cells were isolated (or purified) by FACS. Panel B shows immunofluorescent staining for Pax7 (in red) in non-purified (i.e. not subjected to FACS isolation) myogenic progenitors following the 35-day differentiation protocol outlined in panel A. Nuclei were stained with Hoechst 33258 (blue). Pax 7 is a marker of quiescent and activated muscle stem cells (also known as satellite cells). Panel C shows an immunofluorescent staining for MHC (red) after myogenic progenitors of panel B were purified by FACS sorting for HNK-1⁻ and C-MET+ cells, and differentiated for 4 days into myotubes, which were stained with an MF-20 antibody to MHC (myosin heavy chain). Nuclei were stained with Hoechst 33258 (blue).
Figure 5:
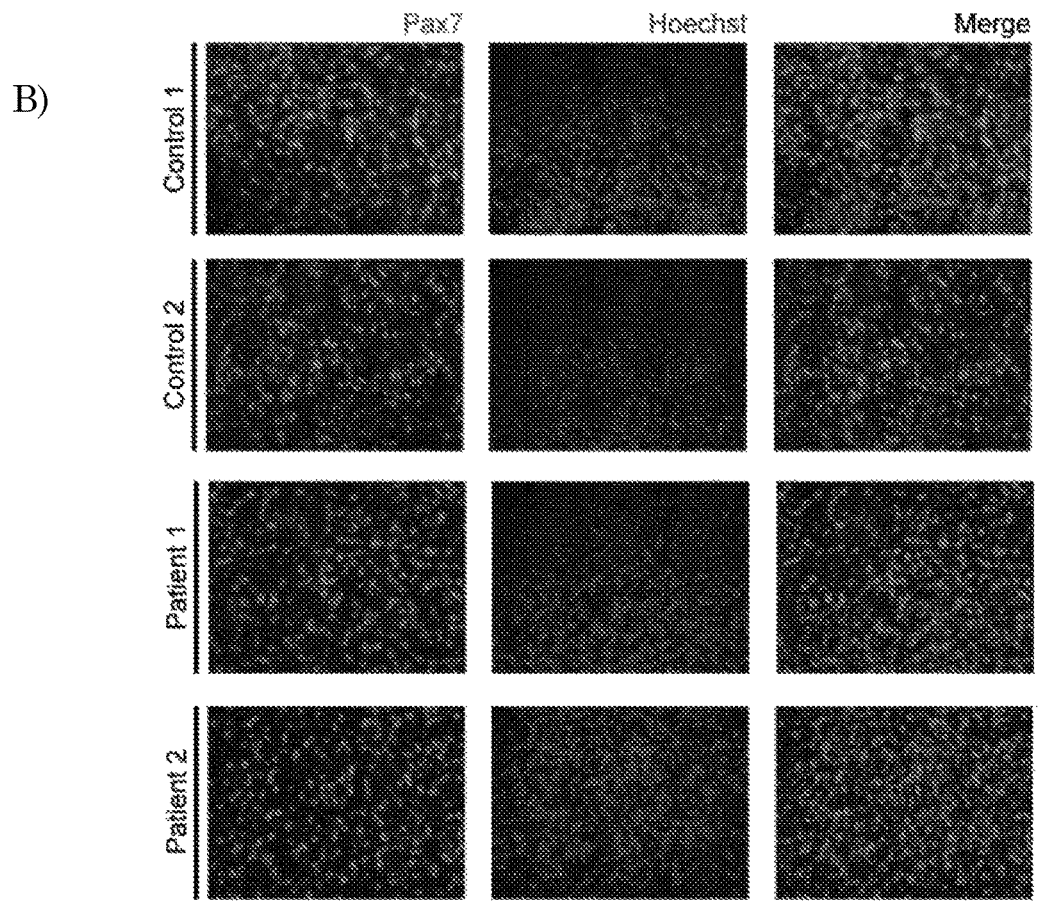
Figure 5:
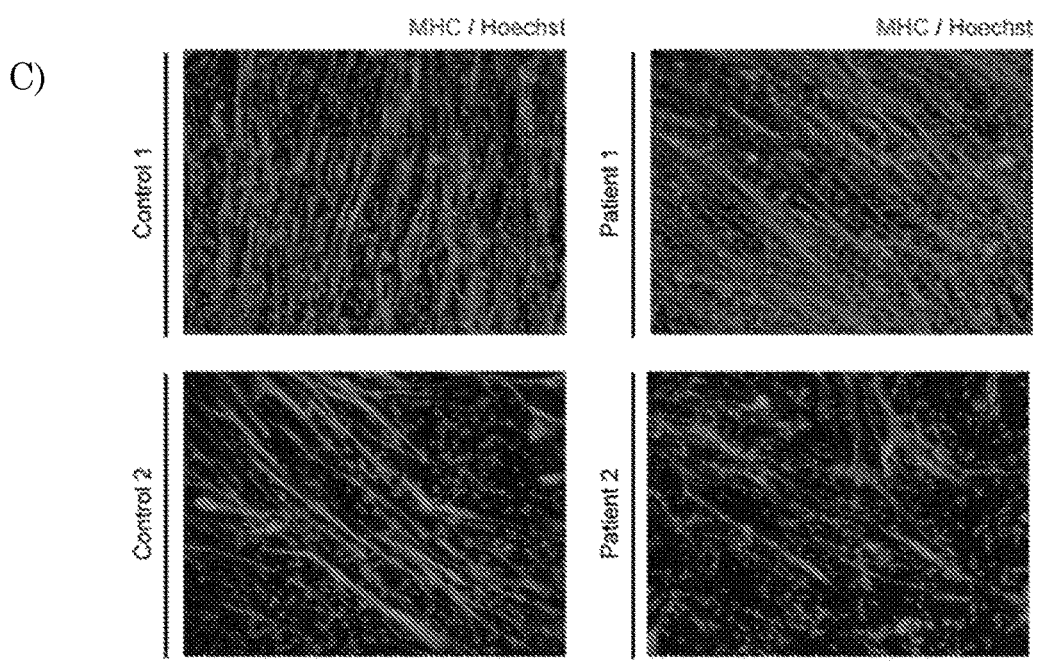
Figure 6:
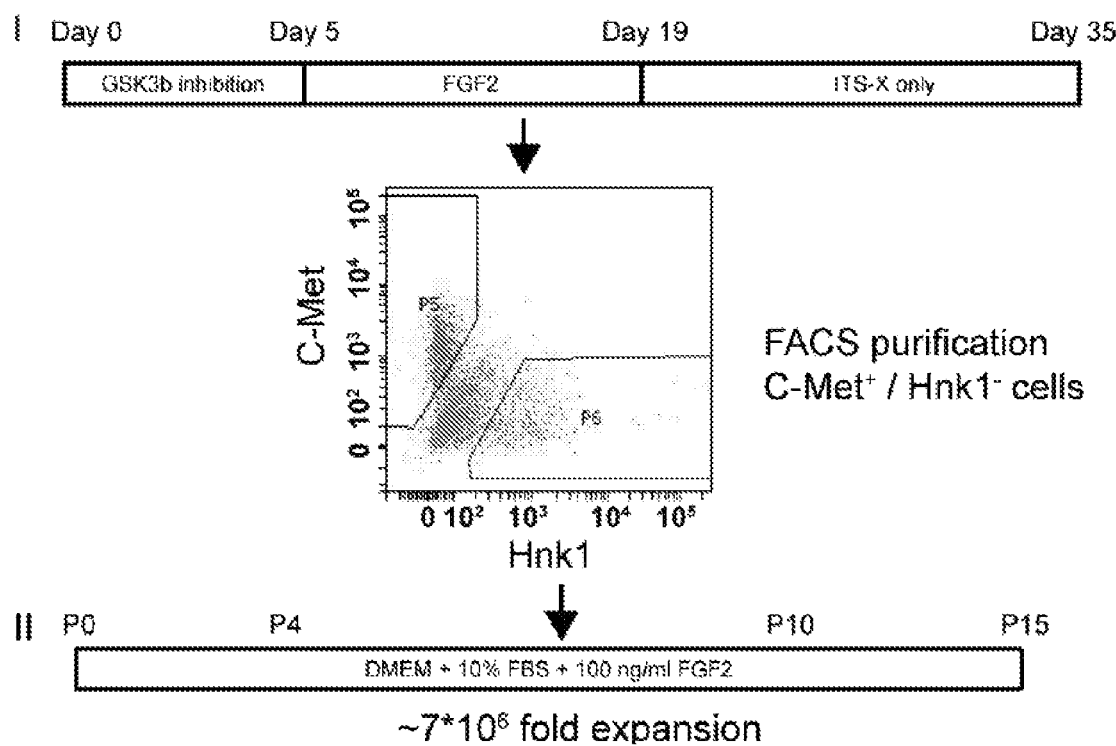
Figure 6:
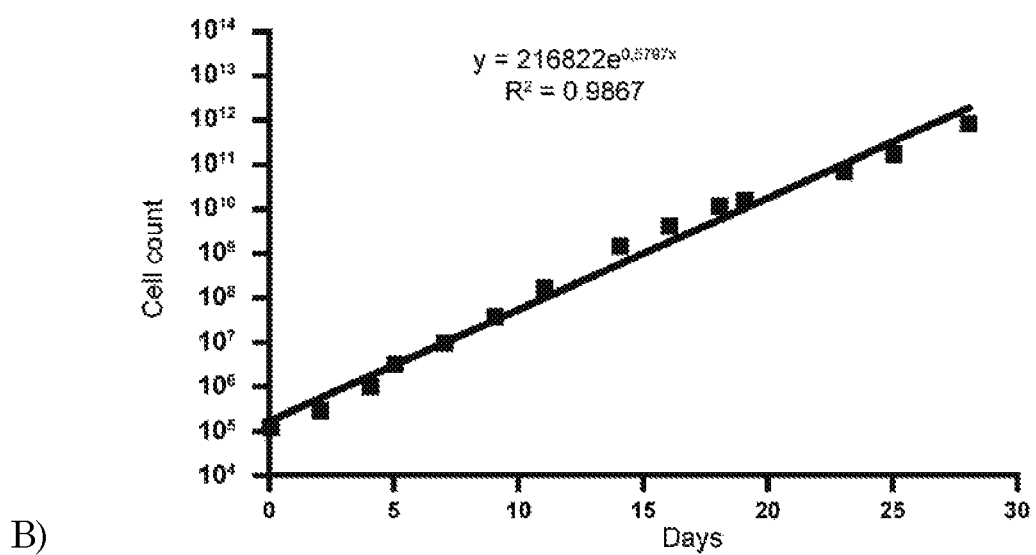
Figure 6:
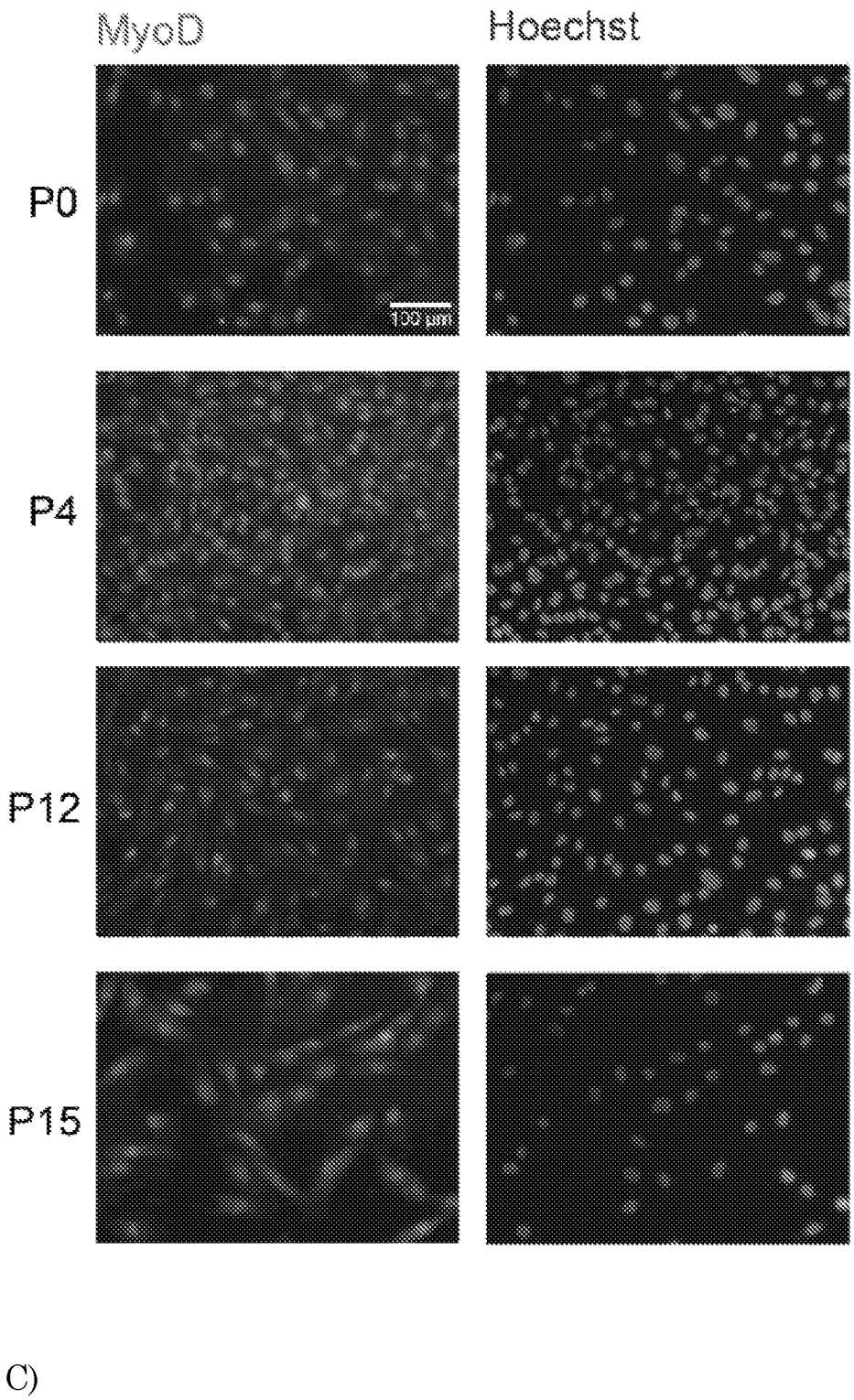
Figure 6:
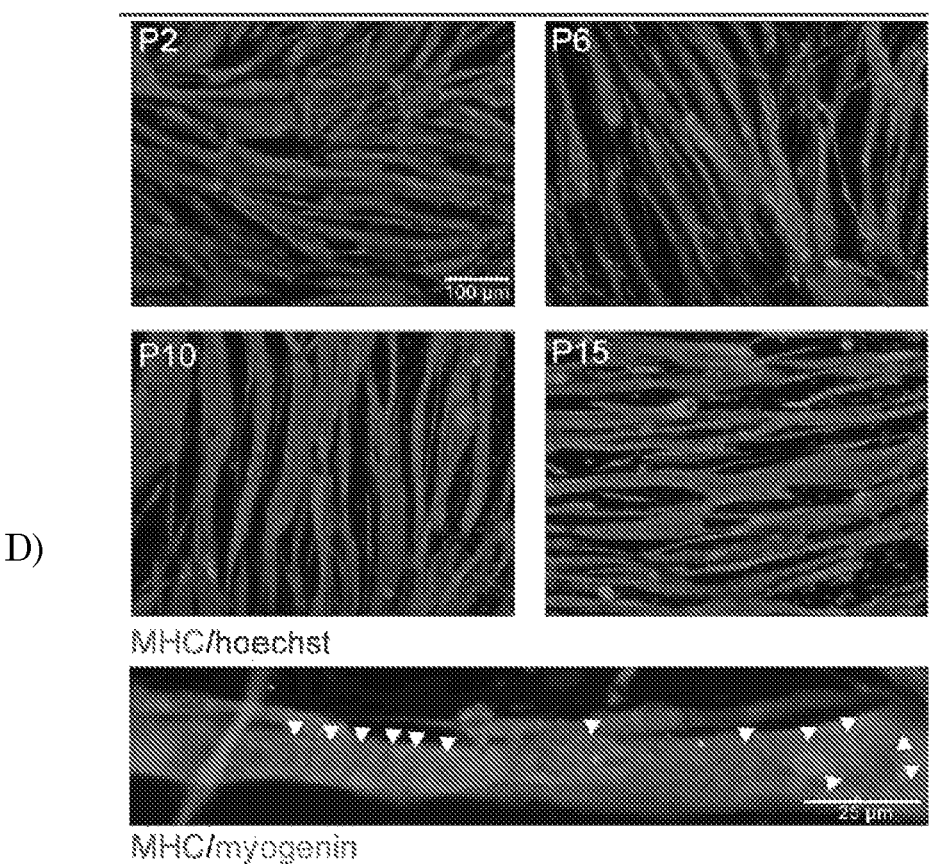
Figure 6:
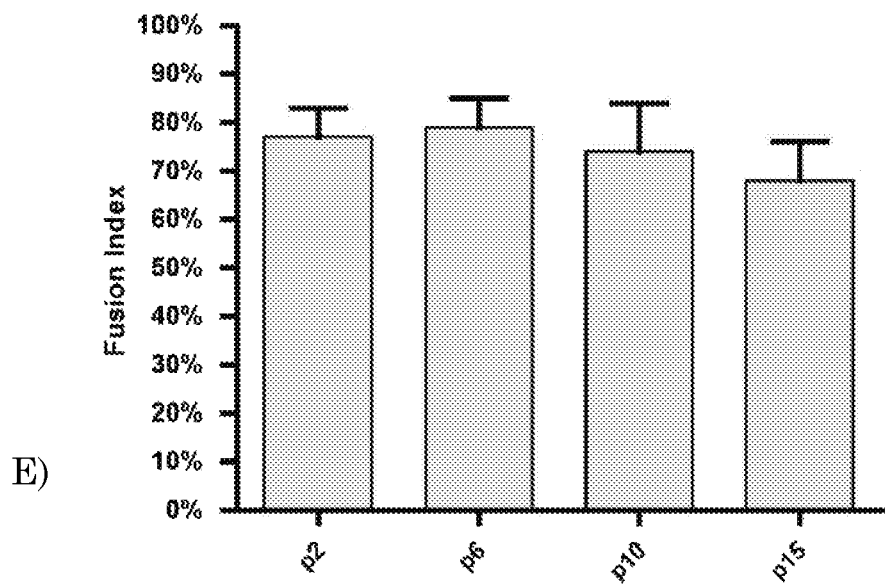
Figure 6:
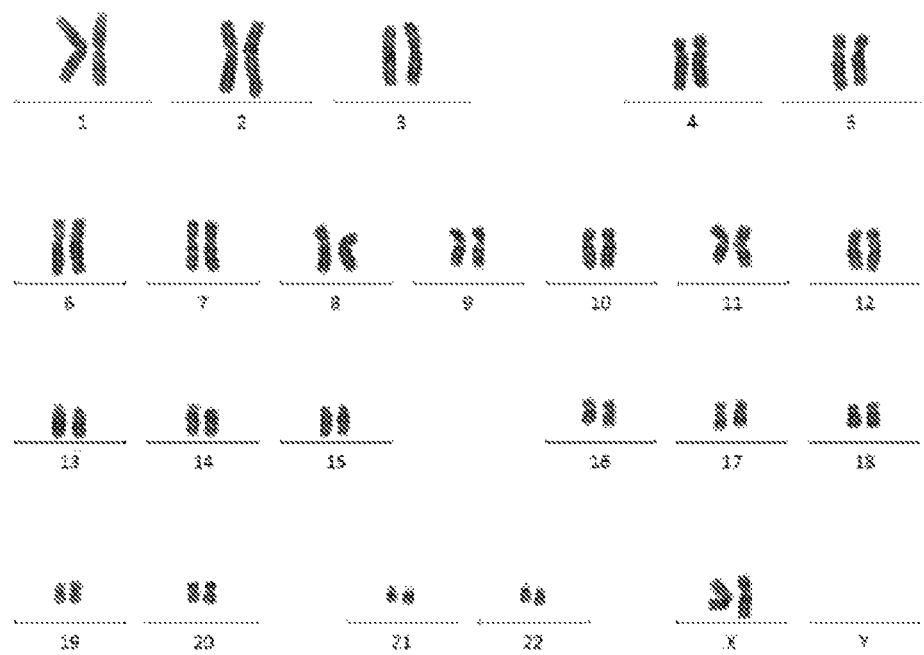

FIG. 6 shows in panel A a culturing and purification scheme I that is identical to that shown in panel A of FIG. 5. In addition, this panel shows a second alternative culturing scheme developed for expanding the purified myogenic progenitors cells obtained after the culturing and purification scheme I. The expansion of purified myogenic progenitors cells revolves around culturing these cells in a medium comprising FGF2 for multiple passages (passage numbers are denoted with a capital p), by which an unprecedented $7 \times 10^6$ fold expansion could be achieved. Panel B shows the cell count during expansion of the purified myogenic progenitor cells obtained from control #2 cell line. The last time point (28 days) corresponds to P15. Panel C shows an immunofluorescent MyoD staining of purified myogenic progenitor cells before and during the expansion process. Hoechst 33258 staining shows that all nuclei are MyoD-positive. It is demonstrated in Panel C that MyoD remains expressed in essentially all cells throughout the entire expansion process. MyoD is a marker for activated muscle stem cells and myoblasts, and is referred to as an intermediate (i.e. neither early, nor late) marker for skeletal muscle differentiation. Panel D shows nucleated myotubes stained with anti-MHC antibody (MF-20; red) and Hoechst 33258 (blue). At several time points during expansion, purified myogenic progenitor cells were differentiated into multinucleated myotubes and stained. The bottom figure shows detail of a typical myotube stained with MF-20 (red) and an anti-myogenin antibody (green). It is noted that expanded cells showed efficient and homogeneous differentiation into multinucleated myotubes that expressed nuclear Myogenin and Myosin Heavy Chain (MHC). Panel E shows the fusion index of myotubes from control #1 generated at several time points during expansion of purified myogenic progenitor cells. Data are means+/−SD (n=5 technical replicates). It follows from this figure that differentiation efficiencies remained similar throughout the expansion phase as is indicated by similar fusion indexes. Panel F shows a karyotype analysis after expansion of purified myogenic progenitors at P16 (a representative example of 15 nuclei). The karyotype remained normal after passage 16.

Figure 7:
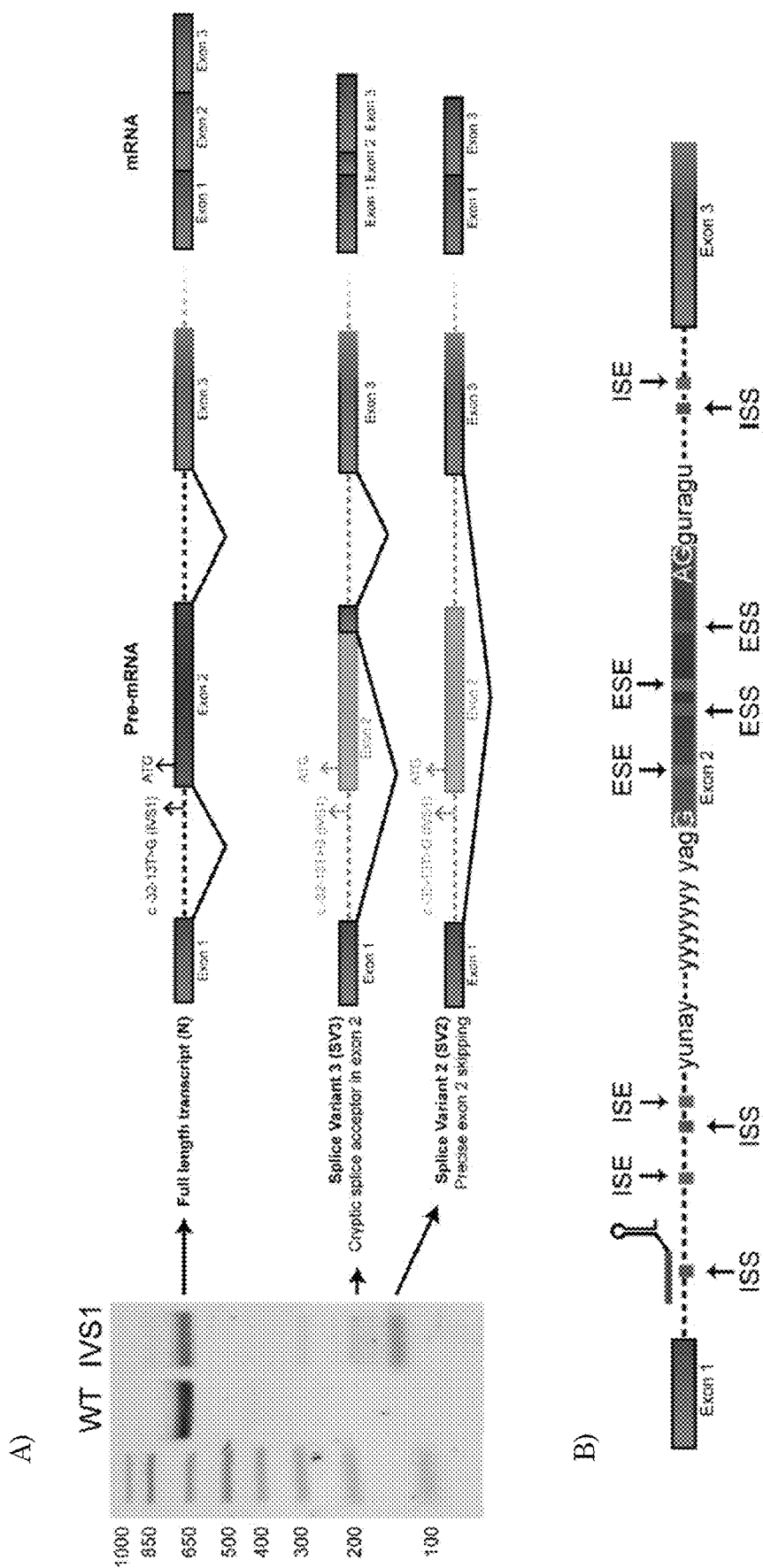
Figure 7:
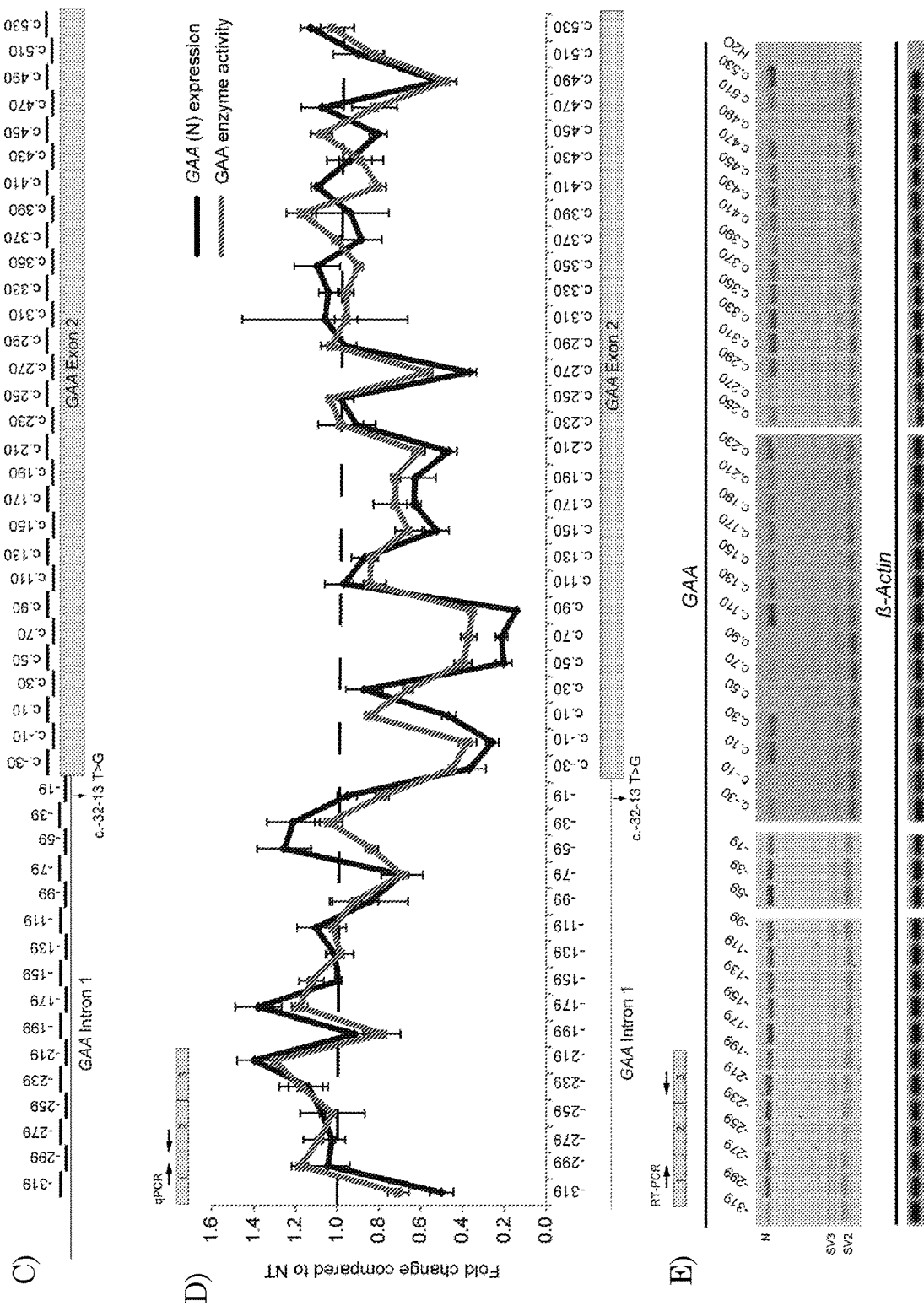
Figure 7:
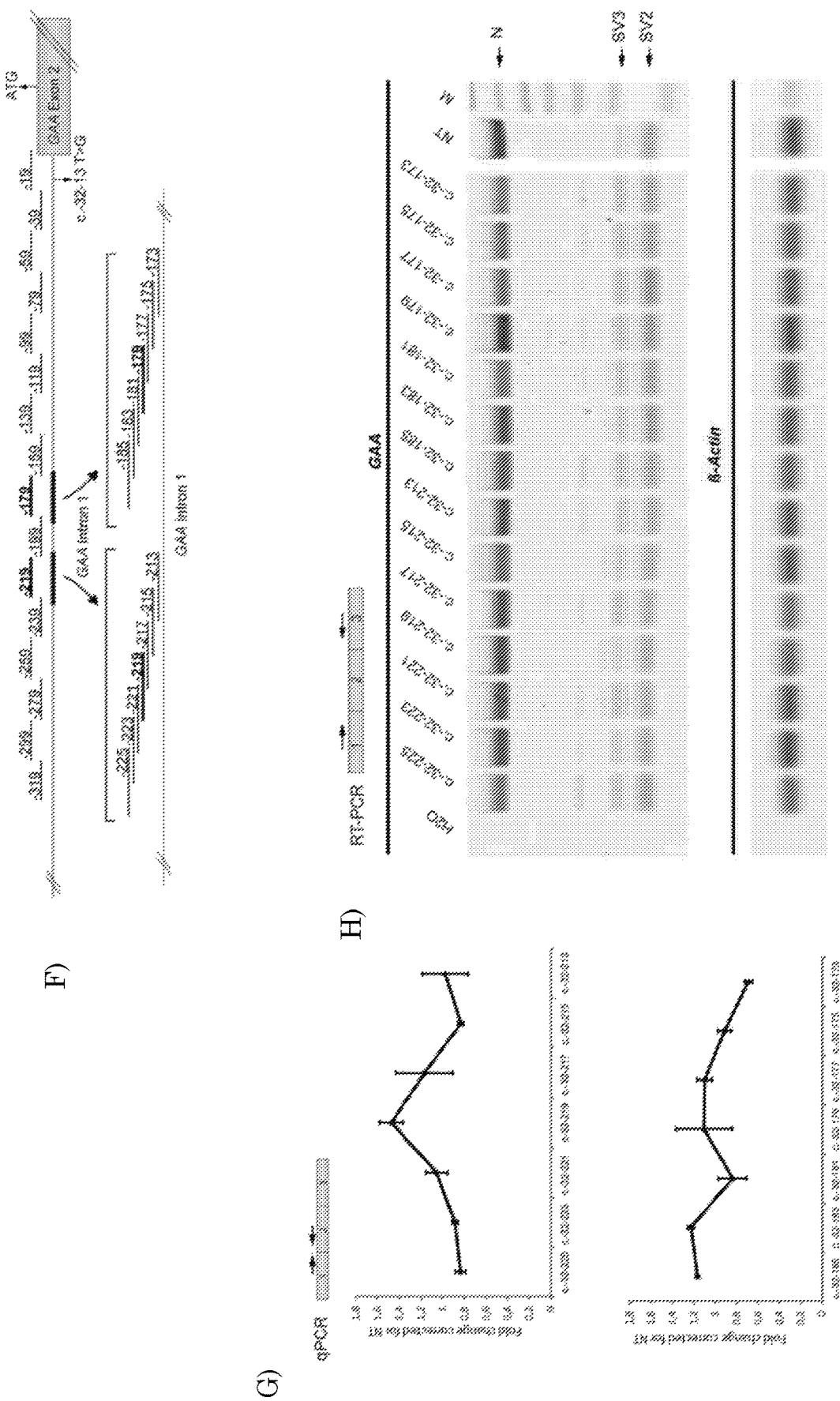

FIG. 7 relates to a screen to identify repressor sequences of aberrant GAA exon 2 splicing caused by the IVS1 variant. Panel A shows the outline of the three major splicing products caused by the IVS1 variant in primary fibroblasts. Panel B shows hypothetical splicing regulatory elements that may be subject to modulation. Splicing is subject to regulation by exonic or intronic splicing silencer (ESS, ISS) or splicing enhancer sequences (ESE, ISE). Panel C shows a schematic drawing of the GAA exon 2 and flanking part of intron 1 with locations complementary to antisense oligonucleotides tested in an intermediate throughput U7 snRNA-based screen. Panel D shows the effect of U7 snRNA-based AONs on GAA exon 2 inclusion in the mRNA (black; GAA (N) expression; measured using RT-qPCR using primers indicated in the upper left schematic drawing) and on GAA enzymatic activity (red) in primary fibroblasts derived from patient #1. The schematic drawing of GAA pre-mRNA below the graph indicates the positions of the AONs tested. Data are expressed relative to non-transduced (NT) fibroblasts and represent means+/−SD of three biological replicates. 200 ng of U7 snRNA expressing lentivirus was used per transduction. Samples were normalized for ß-Actin expression. This figure demonstrates that snRNAs targeting two regions in intron 1, at c.-32-179 and c.-32-219, promoted inclusion of exon 2. Exclusion of exon 2 was promoted by snRNAs that targeted regions in the 5' part of exon 2. Promotion and inhibition of exon 2 inclusion resulted in increased and decreased GAA enzymatic activity, respectively. Panel E shows the result of the same experiment as in Panel D, wherein analysis took place via flanking exon RT-PCR as in Panel A. beta-Actin mRNA was used as loading control. Panel F shows the set-up of a further experiment, a "microwalk", wherein hits from the screen shown in Panel D were further tested using the U7 snRNA system around the regions c.-32-179 and c.-32-219 with 2 nt difference. Panels G and H show the results of the "microwalk" experiment, as analyzed by RT-qPCR. These panels demonstrate that the identified locations were peak values, while two additional snRNAs were identified that promoted exon 2 inclusion when targeted to c.-32-182 and c.-32-184. Taken together, the U7-based snRNA screen of intron 1 and exon 2 identified regions potentially involved in repression of GAA exon 2 inclusion.

Figure 8:
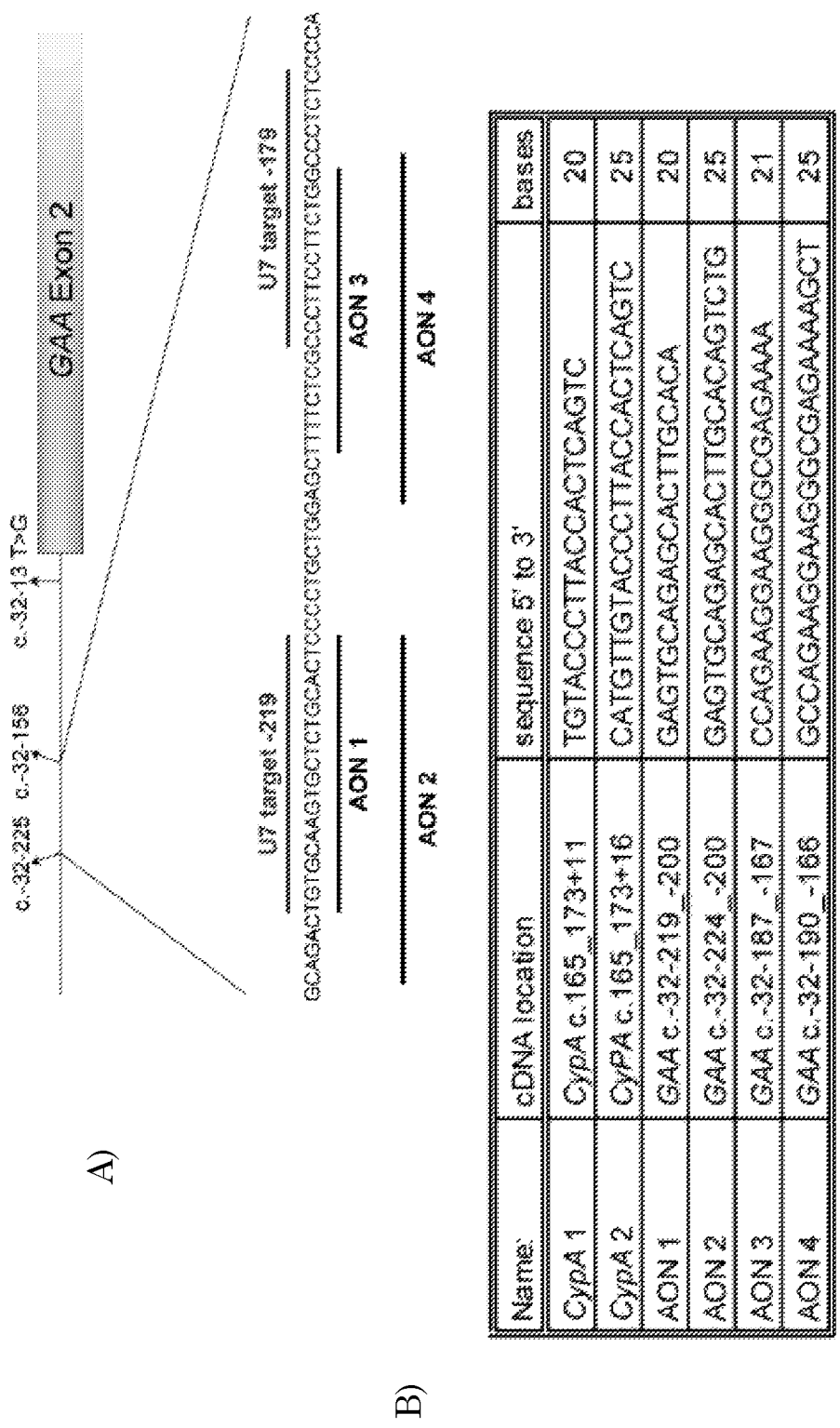
Figure 8:
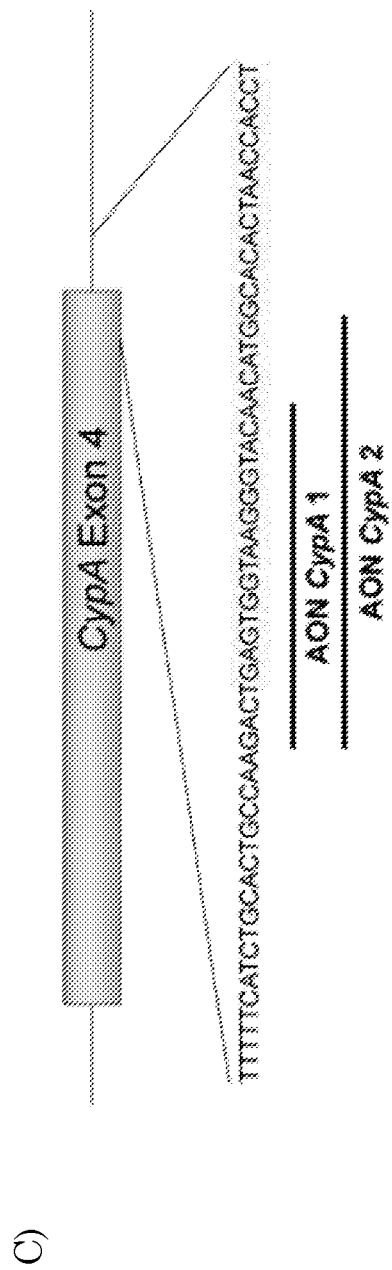

FIG. 8 shows in panel A the positions in the GAA pre-mRNA to which phosphorodiamidate morpholino oligomer (PMO)-based antisense oligonucleotides (AONs) 1-4 anneal, which were designed to target the two major putative repressor sequences at c.-32-219 (AONs 1 and 2) and c.-32-179 (AONs 3 and 4). Panel B shows the sequences of the PMO-AONs that were used. As a control, two PMO-based AONs were used that target the 3' donor splice site of exon 4 in the CypA pre-mRNA and these were able to promote skipping of exon 4 and exons 3+4 after transfection into primary fibroblasts. Panel C shows the location of AONs designed to block the donor splice site of CypA exon 4.

Figure 9:
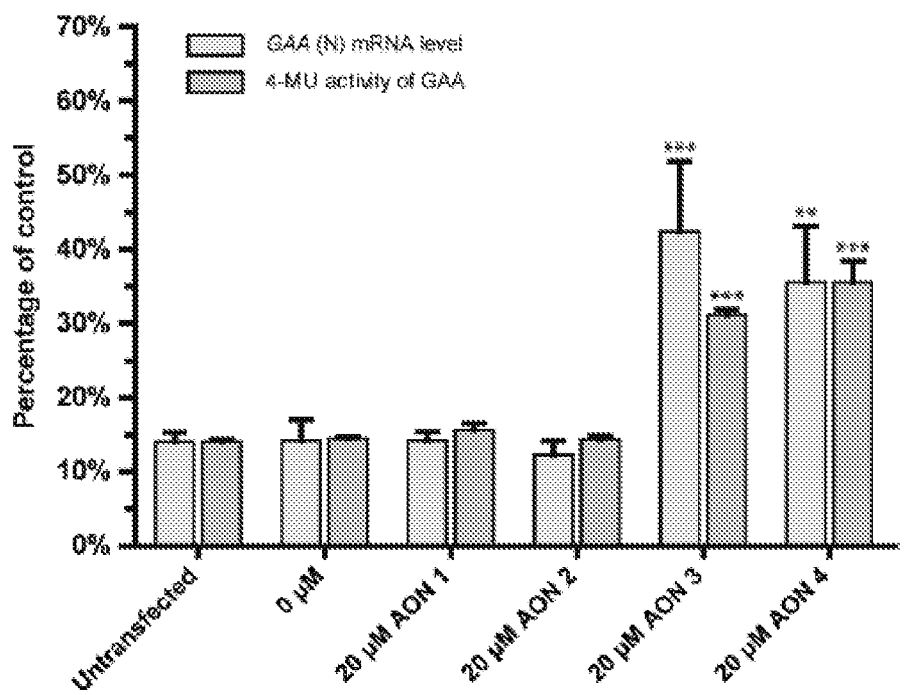
Figure 9:
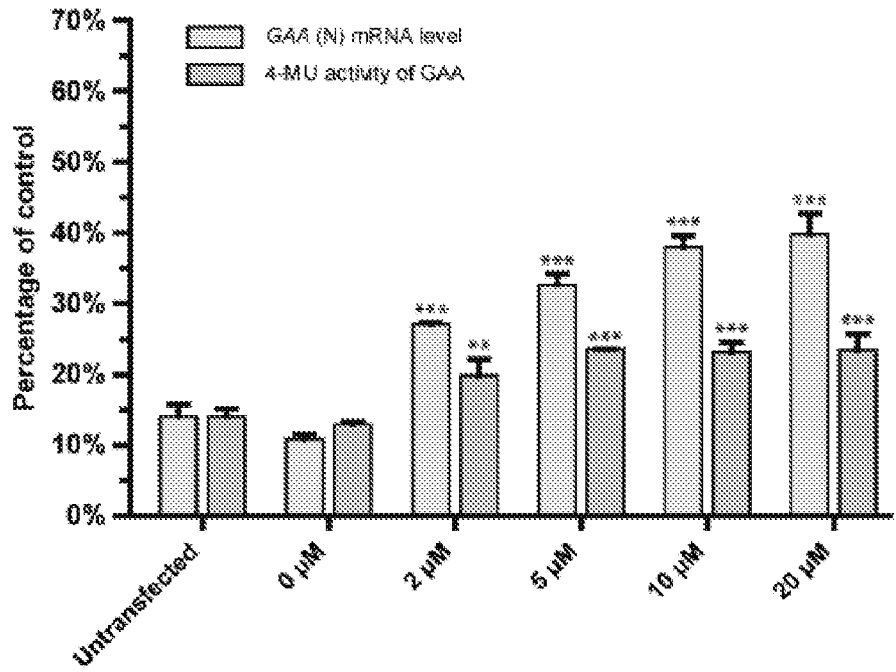
Figure 9:
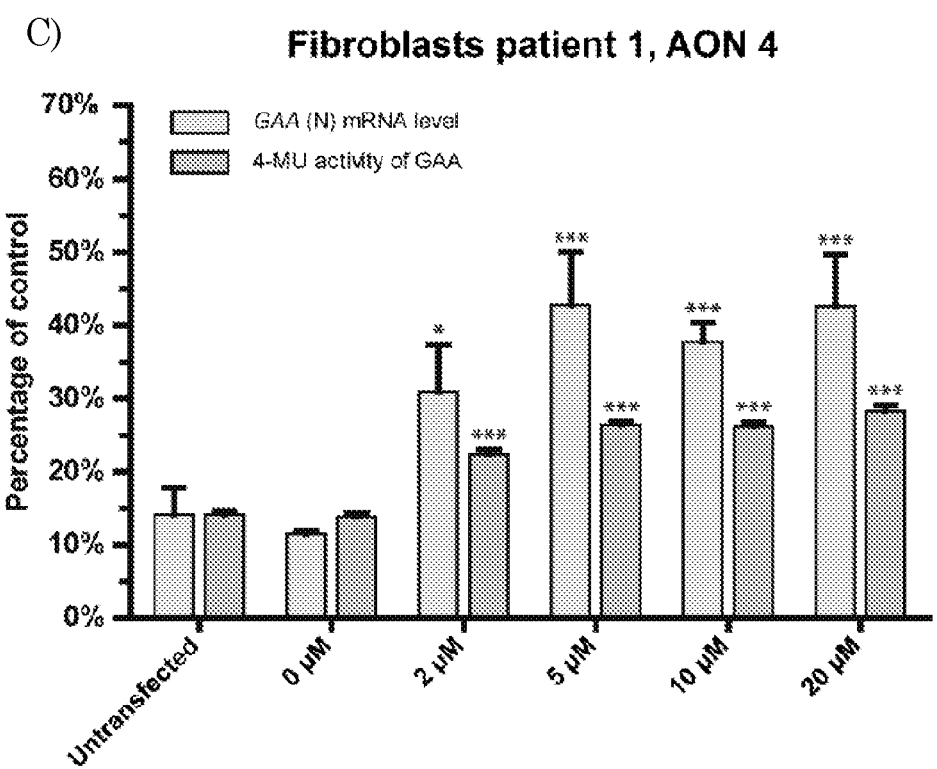
Figure 9:
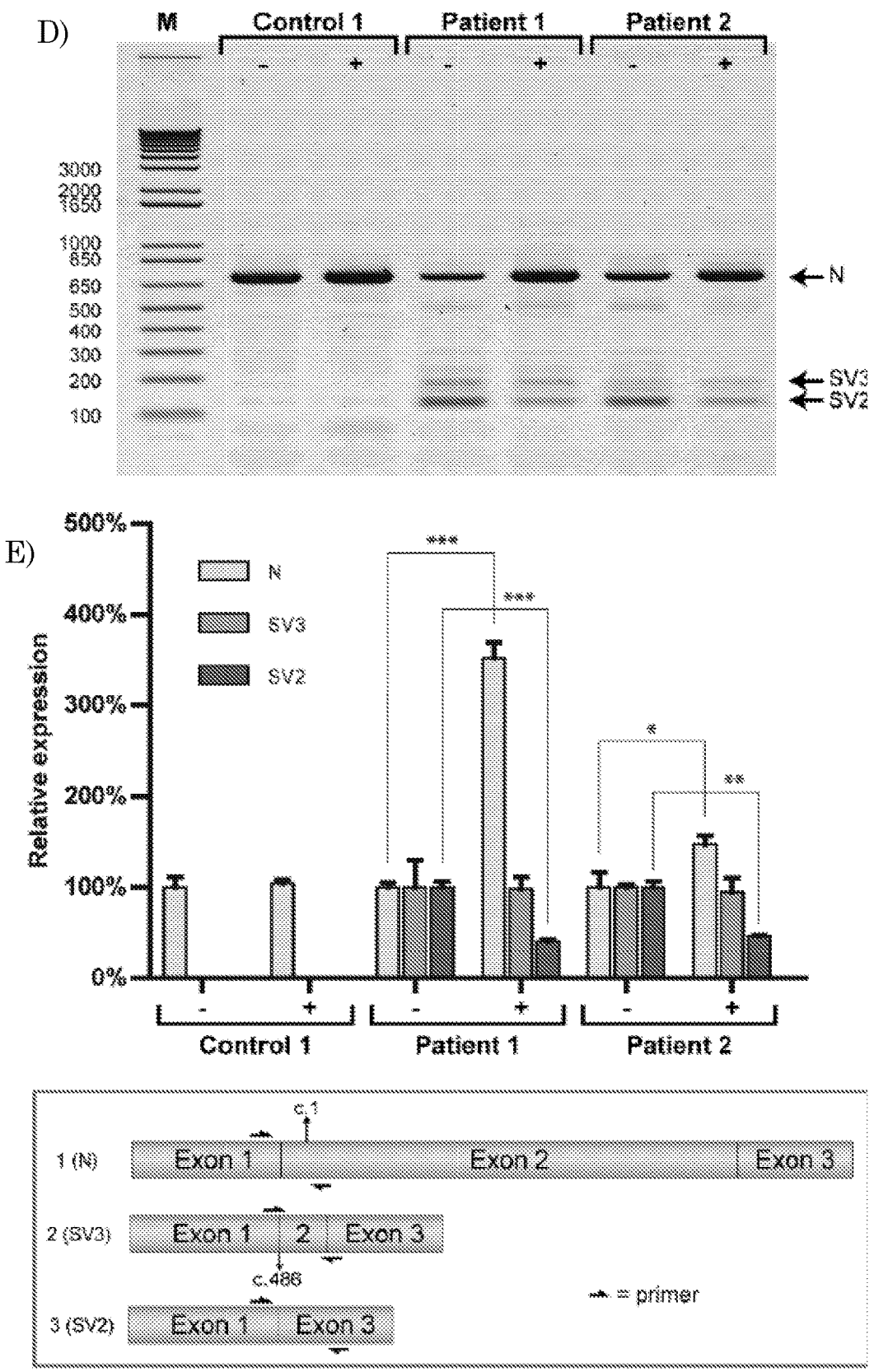

FIG. 9 shows the effect of AONs 1-4 on GAA exon 2 inclusion in fibroblasts from patient #1 using RT-qPCR and analysis of GAA enzymatic activity in panel A. Data are expressed relative to levels in healthy control fibroblasts and were corrected for ß-Actin expression. RT-qPCR analysis shows that AONs 3 and 4 promoted exon 2 inclusion more than 2-fold, whereas AONs 1 and 2 were ineffective. It is also shown for AONs 3 and 4 that 4-MU activity of GAA increased correspondingly with GAA N mRNA levels. Panels B and C show the same result as Panel A, but now in a concentration range of AONs 3 and 4, respectively. Effects of AON 3 and 4 were almost maximal at 2 μM AON and reached a maximum at 5-20 μM. Panel D shows the results of a RT-PCR analysis on the effect of AON 4 on GAA exon 2 inclusion in fibroblasts from patient #1 and #2. "−"=0 μM AON, "+"=20 μM AON. It is demonstrated herein that the expression level of the full length GAA transcript (N) is increased. Panel E shows an RT-qPCR analysis of the individual splicing products of GAA exon 2 splicing. The N, SV2, and SV3 products were quantified using primers as outlined in the schematic drawing, and the effect of AON 4 on GAA exon 2 splicing was determined in fibroblasts from patients #1 and #2 and control #1. To confirm that AONs enhanced GAA enzymatic activity occurs via splicing rather than total gene expression, individual splicing products were analyzed. RT-PCR analysis showed that in IVS1 patients, AON 4 treatment increased the amount of full-length (N) transcript, while the amount of full skip (SV2) transcript was reduced.

Figure 10:
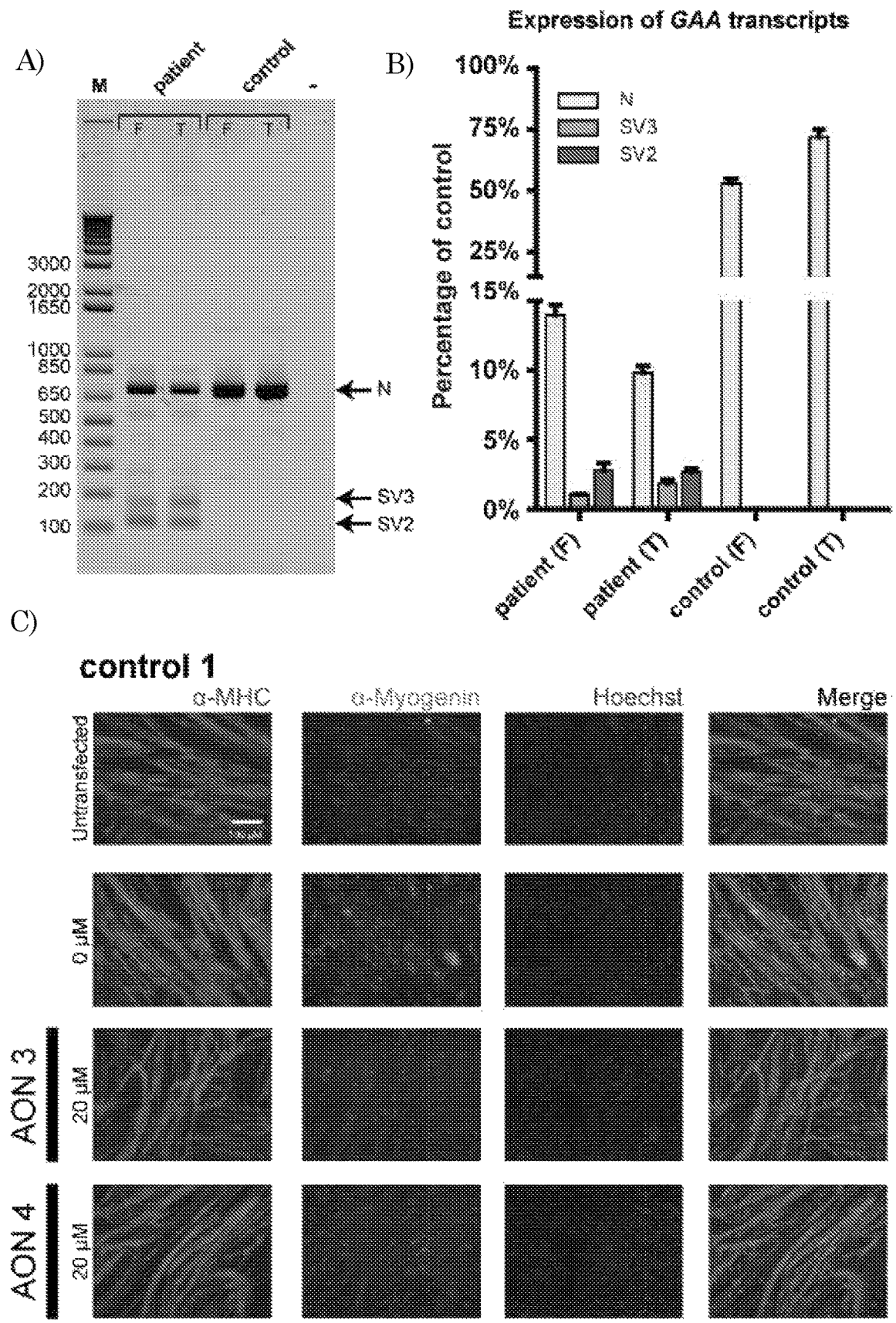
Figure 10:
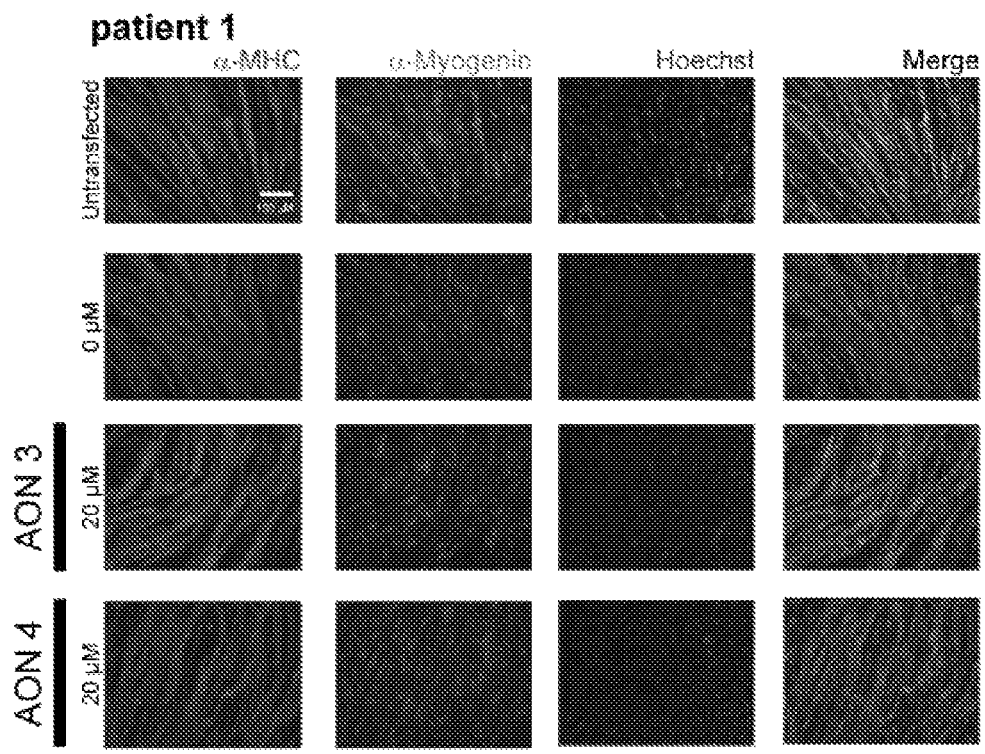
Figure 10:
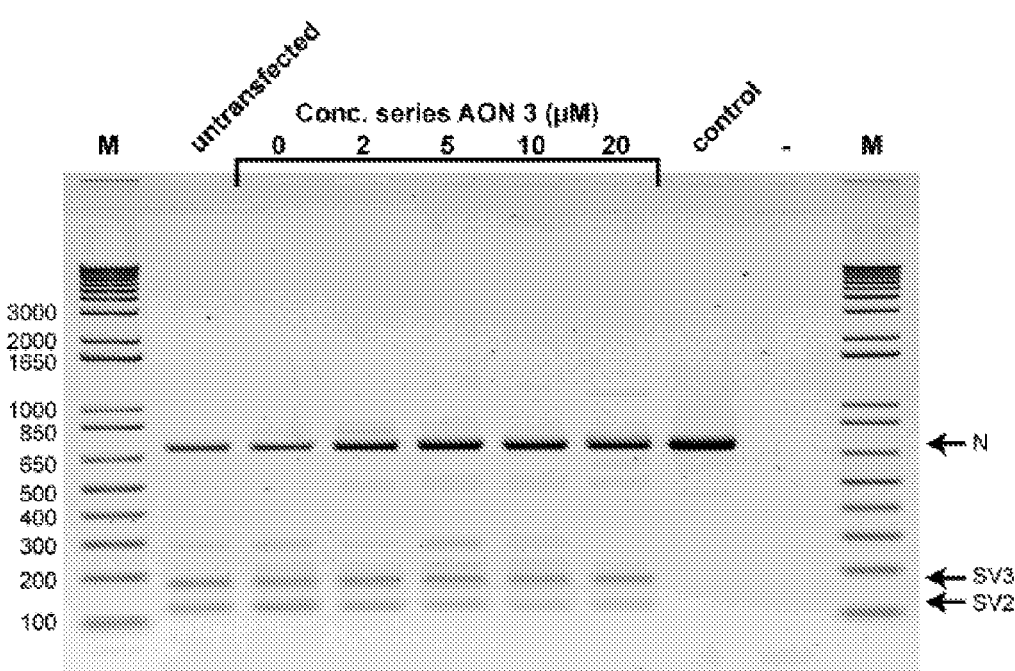
Figure 10:
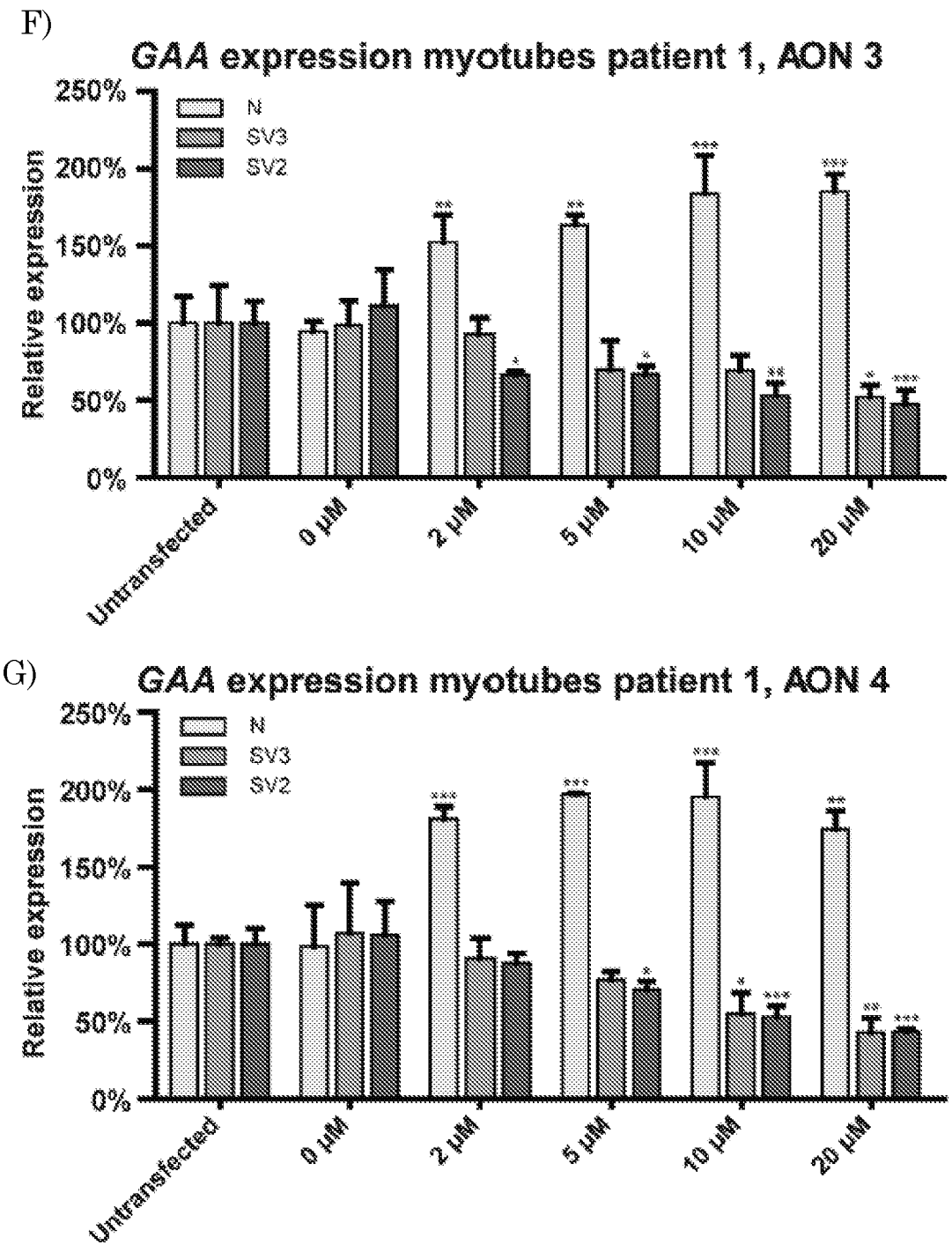
Figure 10:
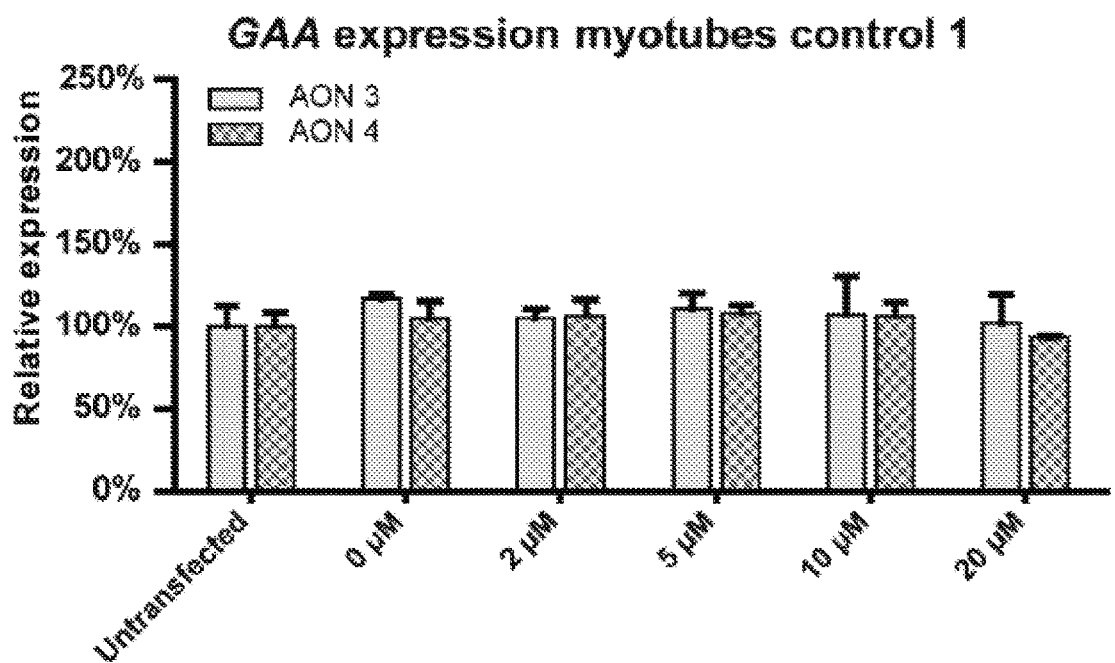
Figure 10:
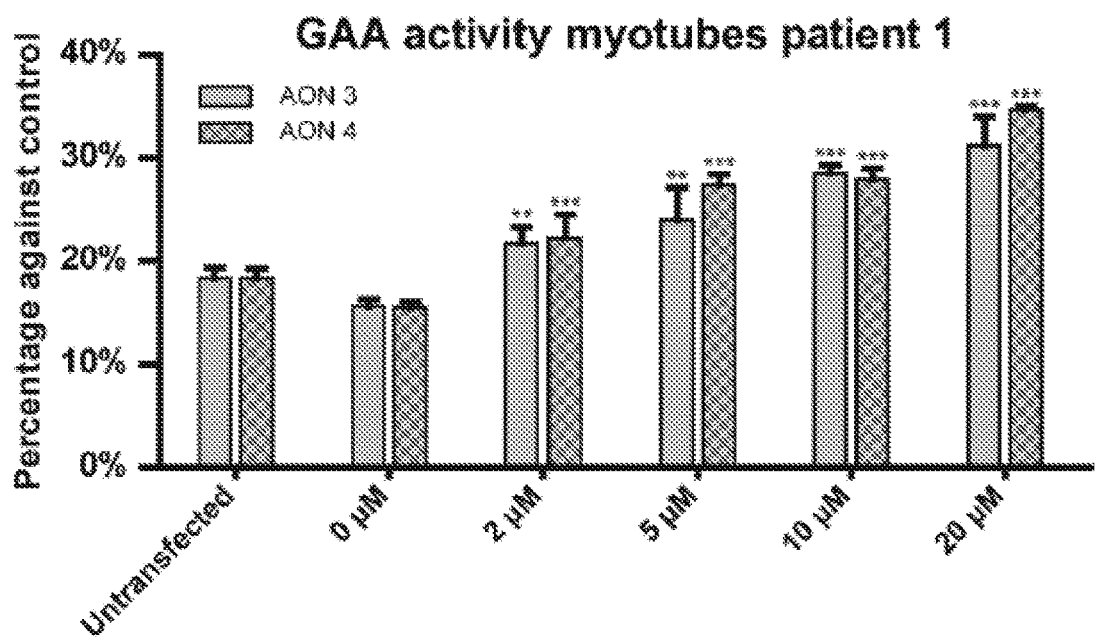
Figure 10:
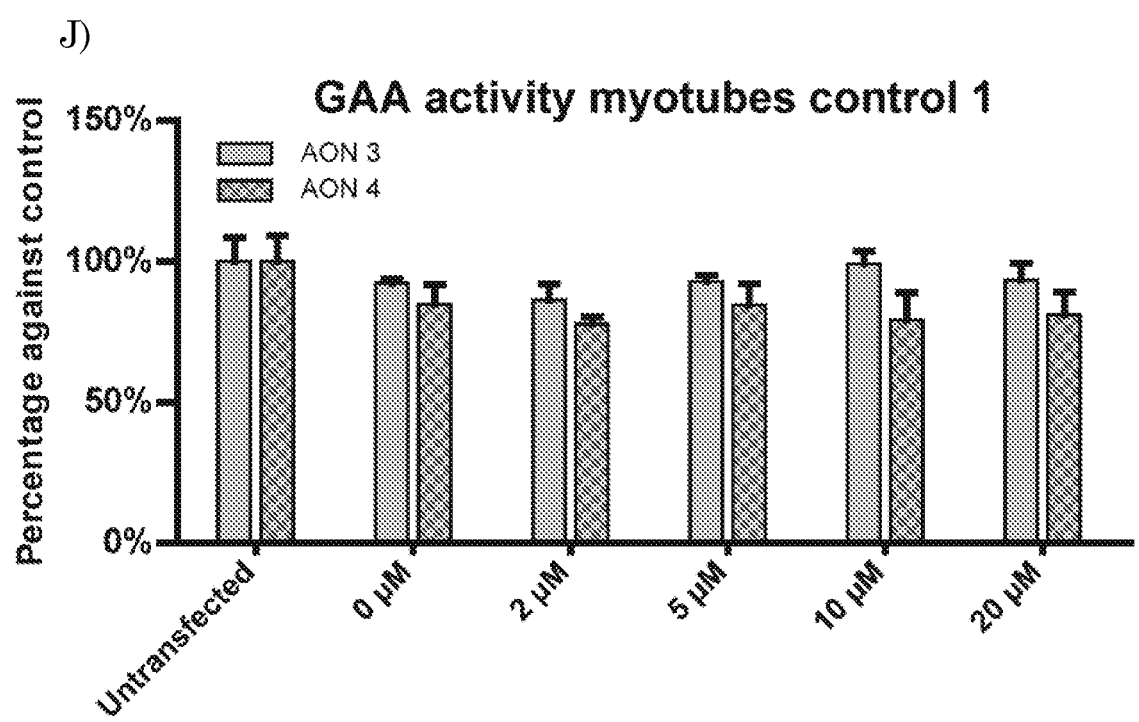

FIG. 10 shows in panel A the result of RT-PCR analysis in primary fibroblasts myotubes (F) and iPS-derived myotubes according to the invention (T) from patient #1 and control #2. All samples have the same RNA input. The effect of the IVS1 variant in skeletal muscle cells (which was unknown so far) was tested in iPS cell-derived myotubes. Flanking exon RT-PCR analysis showed a similar effect compared to fibroblasts. Control myotubes did not show obvious aberrant GAA pre-mRNA splicing. Panel B shows an analysis of individual splicing products using RT-qPCR. To facilitate comparison between different cell types, no normalization was used, and all products were compared to the value of average control fibroblast product N levels using the delta-Ct method. Panels C and D show the staining of myotubes obtained from expanded control #1 and patient #1 iPS cells, treated with AONs 3 and 4. Red: MHC (anti-MF-20); green: Myogenin; blue: nuclei (Hoechst 33258). 0 µM: mock transfection. Panel E shows an RT-PCR analysis of the effect of AON 3 on GAA exon 2 splicing in myotubes from patient #1 and control #1 as indicated in panels C and D. AON 3 causes a concentration-dependent increase in exon 2 inclusion, as judged from the increase in the amounts of the wild type variant (N) and a concomitant decrease in the amounts of the partial (SV3) and full exon 2 skip (SV2) variants. Panel F confirms the result of Panel E by using RT-qPCR with primers specific for individual splicing variants in myotubes from patient #1 treated with AON 3. Data were normalized against expression of four genes that showed no consistent changes in expression: MyoD, Myog, LAMP1, and LAMP2. Panel G shows the same result as Panel F, but now for AON 4. Panel H) shows the effect of AONs 3 and 4 on GAA expression in myotubes of control #1 (as measured using RT-qPCR analysis of product (N)). It was shown that AON 3 and AON 4 do not have any effect on the expression of (N). Panel I shows the effect of AON 3 and 4 on GAA enzymatic activity in myotubes from patient #1. It is demonstrated that AON 3 and AON 4 increase the GAA activity in myotubes of patient #1. Panel J shows that the GAA activity in myotubes of control #1 is unaffected by AON 3 and AON 4.

Figure 11:
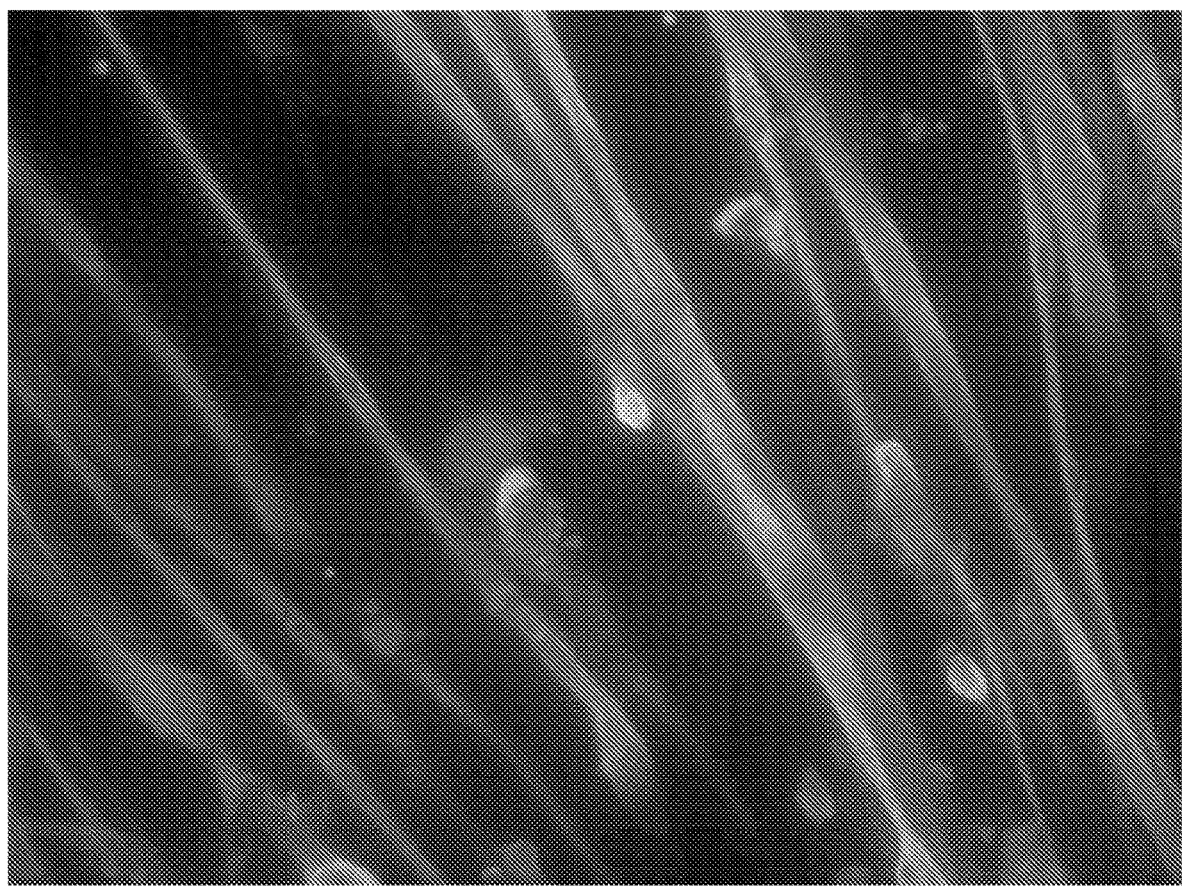

FIG. 11 shows the staining of myotubes obtained from expanded control #1 after 9 days differentiation in long-term differentiation medium. green: Titin; blue: nuclei (Hoechst 33258), as described in Example 7.

Figure 12:
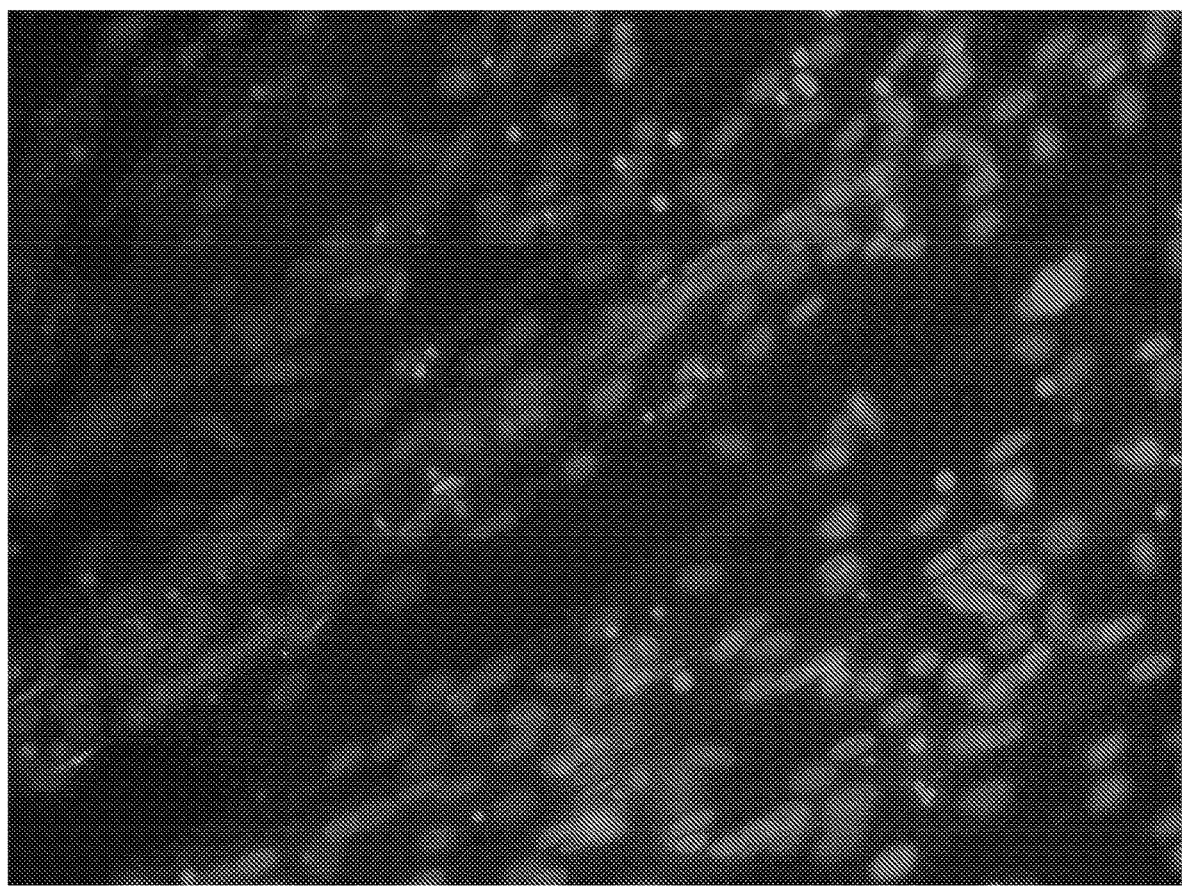

FIG. 12 shows the staining of myotubes obtained from expanded control #1 after 9 days differentiation in long-term differentiation medium. red: nicotinic acetylcholine receptor; blue: nuclei (Hoechst 33258), as described in Example 7.

Figure 13:
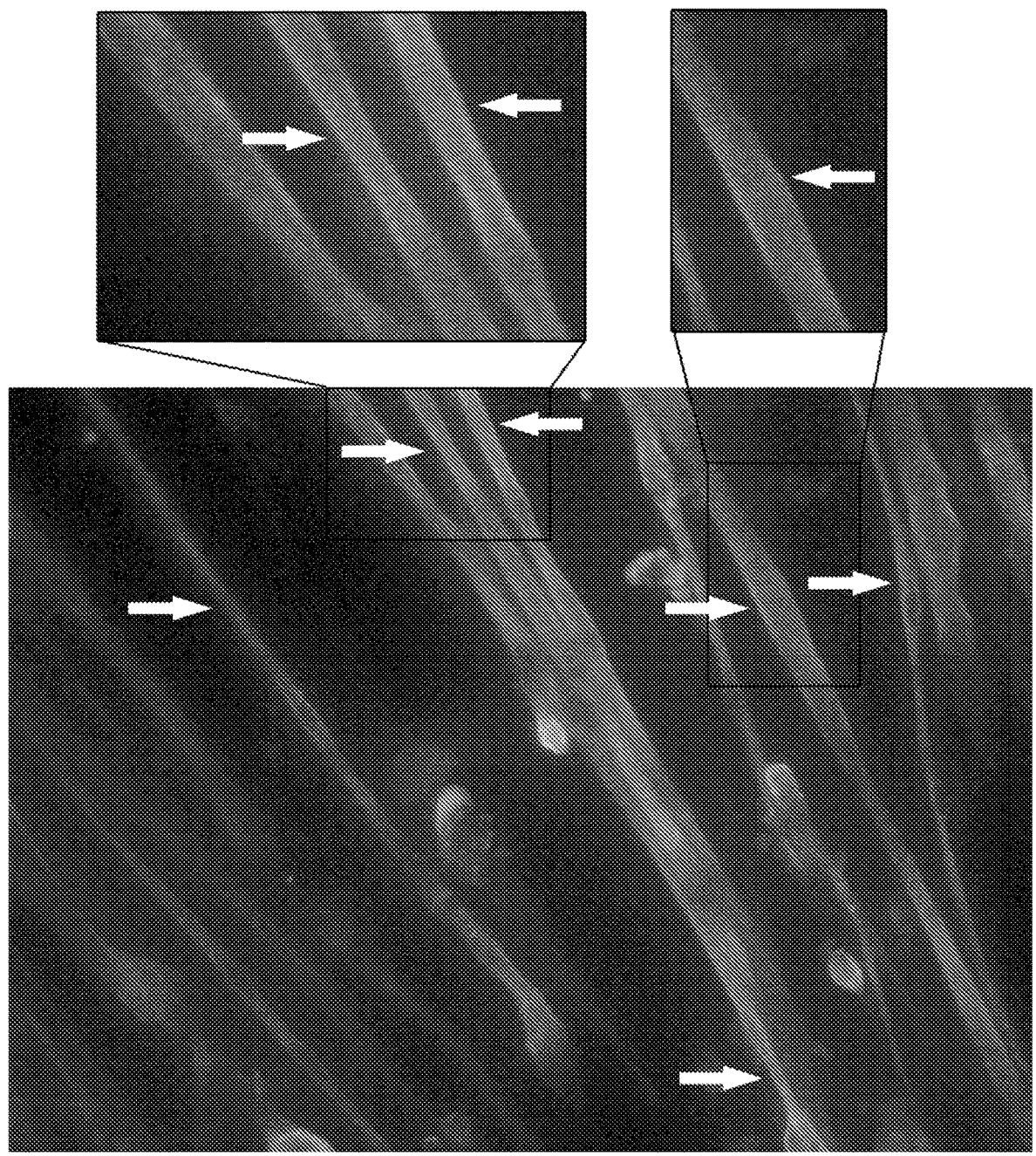

FIG. 13 shows the titin staining of myofibers obtained from expanded control #1 after 9 days differentiation in long-term differentiation medium, as described in Example 7. Arrows indicate the location of the titin staining.

Figure 14:
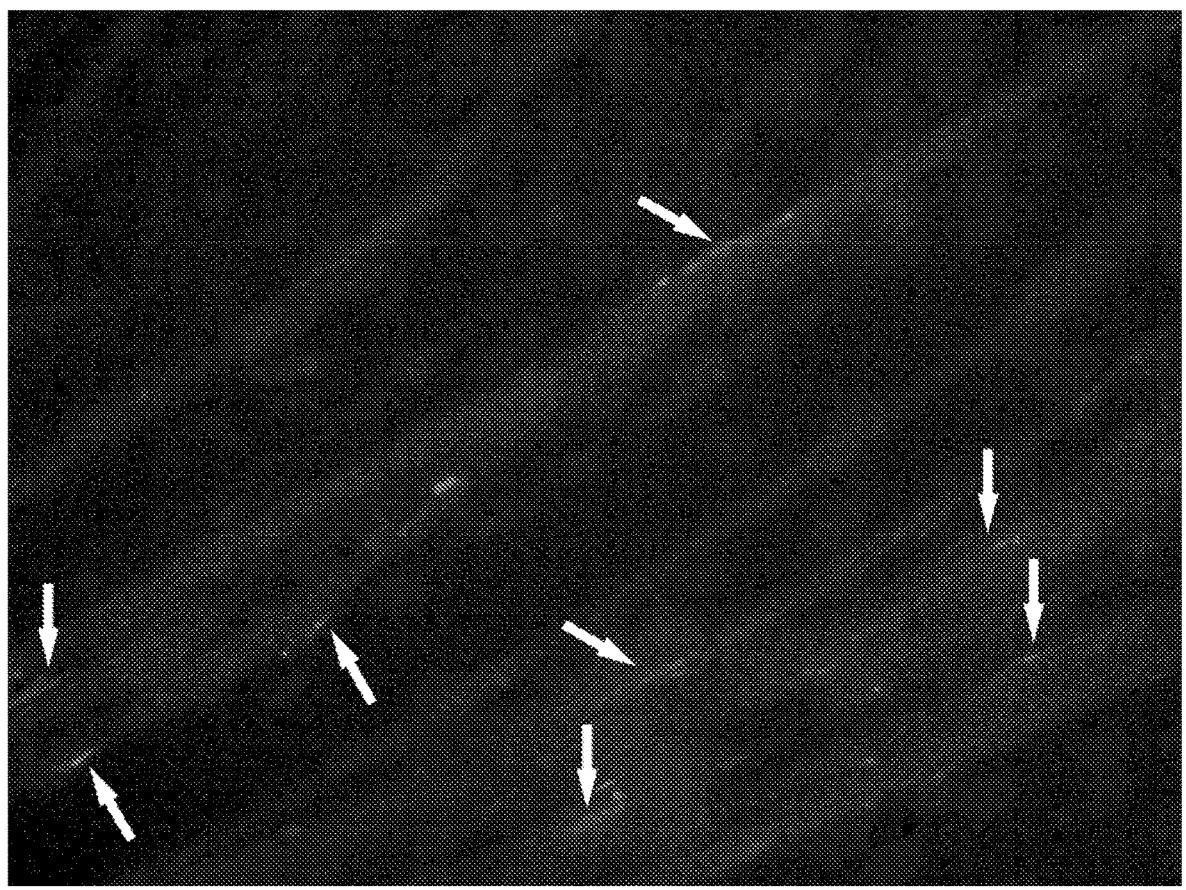

FIG. 14 shows the nicotinic acetylcholine receptor staining of myofibers obtained from expanded control #1 after 9 days differentiation in long-term differentiation medium, as described in Example 7. Arrows indicate the location of the nicotinic acetylcholine receptor staining.

Figure 15:
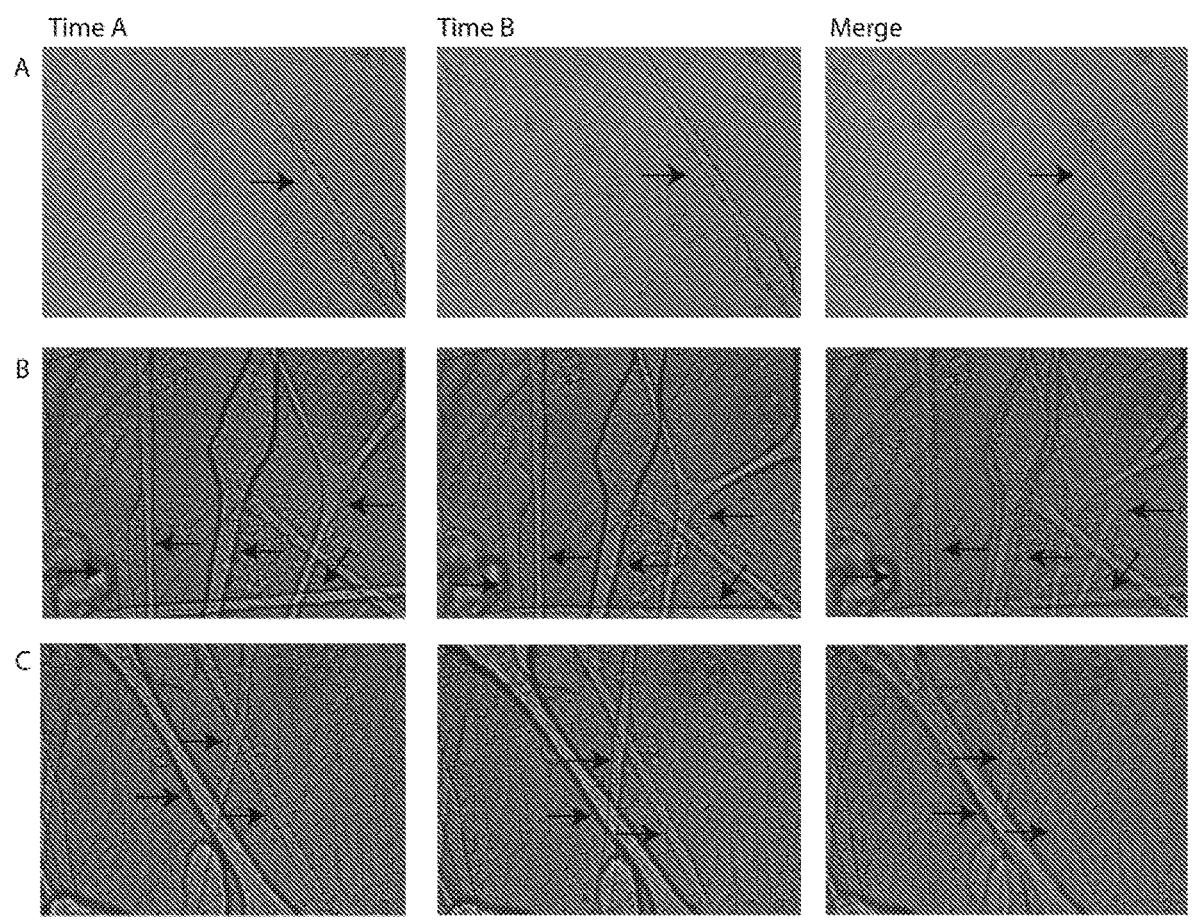

FIG. 15 shows the contractile properties of iPS-derived myofibers. Three examples from a culture are shown that are representative for the entire culture. This was observed in a minimum of 6 cultures per experiment and two independent experiments. A, B, and C show frames of fibers at different times (time A and time B, which are less than one second apart), the right panel shows the merge of the frames at two time points to illustrate that the fibers have moved. Arrows indicate the regions at which contractions were observed.

Figure 16:
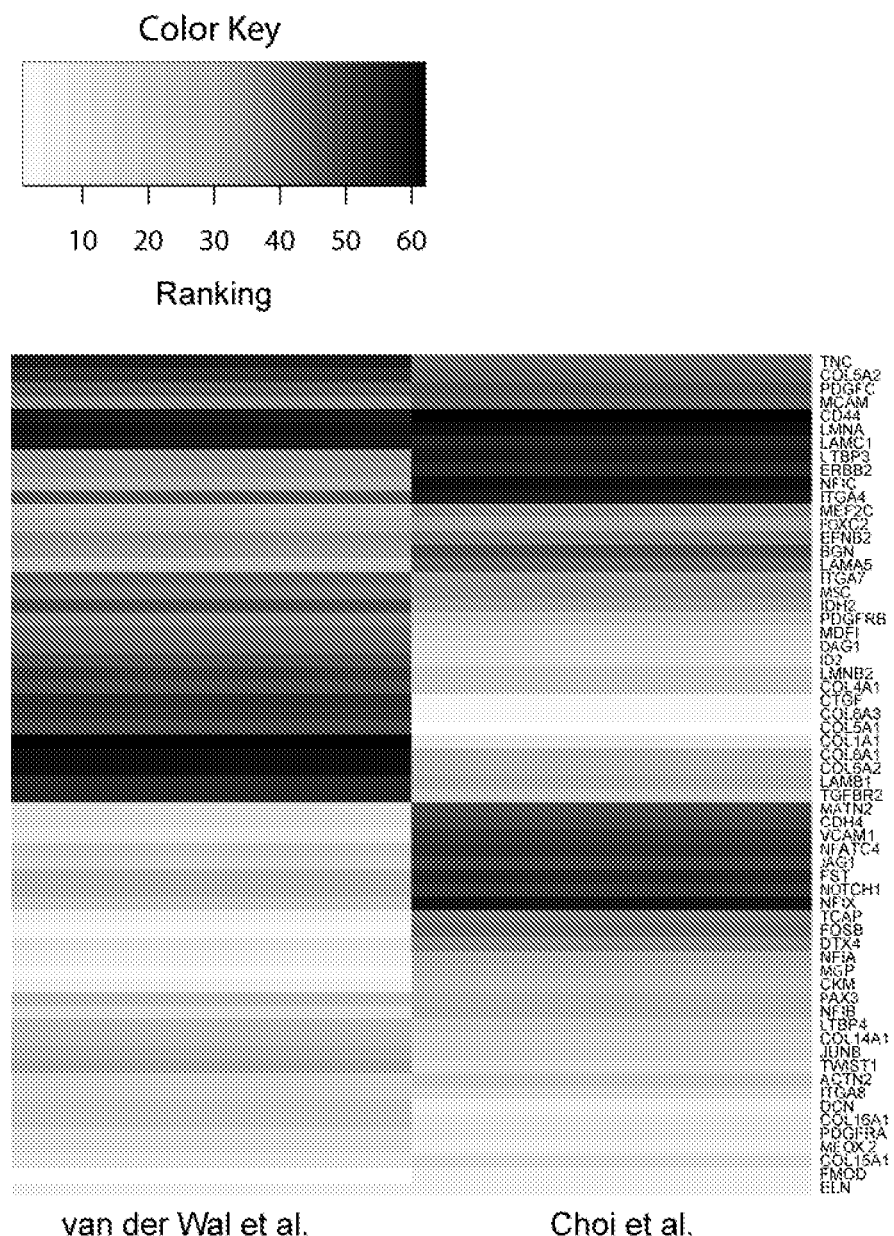

FIG. 16 Gene expression signature from human iPSC-derived myogenic progenitor cells.

We have analyzed the genome-wide mRNA expression profile of human iPS-derived myogenic progenitor cells (MPCs) described in this patent. The only published dataset for human iPS-derived skeletal muscle cells in which genome wide mRNA expression of all genes has been described (Choi et all.) is used for comparison. We have looked at 78 genes described in the literature to define and distinguish fetal from embryonic muscle stem cells in the mouse (Biressi et al.) and for which a similar role in human is suspected. We have compared the expression of these 78 genes between our dataset ("van der Wal et al.") and Choi's dataset ("Choi et al"). We have ranked the genes according to their expression level, with a low ranking in white indicating low expression, and a high ranking in black indicating high expression. This shows that the profiles of the iPSC-derived MPCs described in this study are substantially different compared to the cells described in Choi et al. Notably, there are genes that have relatively high expression levels in Choi et al but not in van der Wal et al, for example MATN2, CDH4, VCAM1, NFATC4, JAG1, FST, NOTCH1, NFIX, and there are also genes with a relatively high expression level in van der Wal et al but not in Choi et al., for example CTGF, COL6A3, COL5A1, COL1A1, COL6A1, LAMB1, TGFBR2. There are also genes that are not at all expressed in van der Wal et al., while these are expressed in Choi et al (Table 4).

DETAILED DESCRIPTION OF THE INVENTION

Definitions

The term "myogenic cell", as used herein, refers to a cell that, during further differentiation, gives rise to or forms muscle tissue, preferably skeletal muscle tissue, such as myotubes. The term myogenic cell includes reference to and includes cells expressing one or more of the myogenesis markers Pax3, Pax7, MyoD and/or myogenin. Such expression is, for instance, determinable by immunostaining. The term includes reference to a myogenic progenitor cell, i.e. a cell that is not yet fully or terminally differentiated, and includes satellite cells (muscle stem cells), activated satellite cells and myoblasts. Preferably, myogenic cells are not pluripotent stem cells and do preferably not express pluripotency markers such as NANOG, OCT4, SSEA4, TRA-1-81 and/or TRA-1-60, at least not to high levels. Before the expansion step and during isolation, as described in the context of the invention, it is preferred that a myogenic cell is C-Met+ and Hnk1−. Preferably, the myogenic cell is a human cell. Markers that can be used to identify myogenic cells of the present invention in certain embodiments of aspects herein described include Pax7 and Pax3 before expansion and during isolation.

The terms "expansion" and "expanded", as used herein, refer to the process, respectively, the result, of cell division, proliferation or multiplication that is accompanied by in an increase in cell number or cell count of a population of cells under cultivation. The term "expanded" in the context of the present invention, preferably includes reference to embodiments wherein cells are passaged.

The term "passaged", as used herein, refers to the process of enzymatic dissociation of individual cells from colonies, by, for instance, trypsin, and the replacement of the culture medium by fresh medium, to thereby allow the further growth f mammalian cells in culture.

The term "cell culture", as used herein, refers to an in vitro population of viable cells under cell cultivation conditions, i.e. under conditions wherein the cells are suspended in a culture medium that will allow their survival and preferably their growth, such as, for instance, a DMEM-based culture medium. The cell culture is usually comprised in a container holding the cell culture, referred to as a culture chamber, wherein sufficient exchange of gases such as oxygen and CO2 is allowed between the cell culture and the atmosphere to support cell viability. The term "cell culture", as used herein, includes reference to liquid forms, semi-solid forms, forms comprising extracellular matrix (ECM) protein as described below, and to frozen forms of the cell culture, and to single chamber as well as multi-chamber cultivation environments, such as, for instance, a plurality of wells in a multi-well plate. A cell culture of the invention, which comprises, is comprised in, or is present in a synthetic culture medium, is preferably provided in a container or plate for holding a cell culture. Said container or plate is preferably coated with extracellular matrix (ECM) protein. As an extracellular matrix (ECM) protein, one may use, for instance, extracellular matrix (ECM) gel, preferably ECM gel from Engelbreth-Holm-Swarm murine sarcoma fibrillar collagen (E6909 Sigma), and/or preferably a combination of (rat tail) collagen type I and MaxGel ECM (E0282 Sigma), and/or fibrillar collagen, and/or a component of ECM gel, and/or a synthetic mimetic of an ECM component, and/or collagen type I, or a combination thereof. It is envisaged herein that the invention may also be defined in terms of a synthetic culture medium comprising a cell culture of the invention. In the same manner, the invention may also be defined as a container or plate comprising a synthetic culture medium that comprises a cell culture of the invention.

The term "isolated C-Met+ and Hnk1− myogenic progenitor starting cell", as used herein, refers to the inoculum of the cell culture of the present invention, and includes reference to the cell that is isolated from a pre-differentiated population of PSCs comprising, amongst other cells, also cells referred to herein as progenitor cells of myogenic lineage, with which the expansion process of this invention is started. An isolated C-Met+ and Hnk1− myogenic progenitor starting cell is at passage 0 (P0). When cells in a cell culture of this invention are expanded and passaged for at least 1 passage relative to said starting cell, this means that passage 1 (P1) has occurred.

The term "homogeneous", as used herein in the context a population of expanded myogenic progenitor cells of the invention, refers to the circumstance that essentially or substantially all cells in said population have the same differentiation status, e.g. preferably more than 50%, more preferably more than 90%, even more preferably more than 91%, 92%, 93%, 94%, 95%, 96%, 97%, 98%, or 99% of the cells in said population is MyoD positive and Pax7 negative at the differentiation stage immediately prior to terminal differentiation into myotubes. Alternatively, or in addition, the term "homogeneous", as used herein in the context a population of expanded myogenic progenitor cells of the invention, refers to the circumstance that the cells of a cell culture of this invention are, in some embodiments produced from expansion of at least one isolated C-Met+ and Hnk1− myogenic progenitor starting cell origination from a single subject. Cells of a cell culture of this invention may, in other embodiments, be produced from expansion of at least 2, 5, 10, 20, 50, $10^2$, $2\times10^2$, $5\times10^2$, $10^3$, $2\times10^3$, $5\times10^3$, $10^4$, $2\times10^4$, $5\times10^4$, $10^5$, or more isolated C-Met+ and Hnk1− myogenic progenitor starting cells, isolated from a pre-differentiated population of PSCs, preferably originating from a single subject.

The term "isolated", as used in the context of a C-Met+ and Hnk1− myogenic cell, refers to the completed process of isolating or purifying C-Met+ and Hnk1− myogenic cells from a cell culture of myogenic cells resulting from the pre-differentiation of a pluripotent stem cell, preferably an iPSC, as described herein towards a myogenic lineage. It is generally known that, during the process of differentiating pluripotent stem cells into the myogenic lineage, many different cell types may be present in such a culture only a small fraction of which is myogenic, and the isolation of such cells—or their purification—based on the expression of a C-Met+ and Hnk1− phenotype, provides for a very beneficial starting culture for the production of skeletal muscle cells, or their progenitors, as provided herein. The term "isolated" can be used interchangeably with the term "purified". The term "isolated" can also be used with reference to the term "primary", meaning that the cell is isolated from a subject's tissue.

The term "culture medium", as used herein, refers to a medium generally used in the culturing of mammalian, preferably human, cells, including pluripotent stem cells, such as iPS cells, and myogenic progenitor cells and differentiated cells in the context of the invention. Preferably, such a medium is based on Dulbecco's Modified Eagle Medium (DMEM) or Ham's F12 nutrient medium, or combinations of such basal media, optionally supplemented with compounds that prevent bacterial contamination, such as antibiotics, preferably in the form of a combination of penicillin/ streptomycin/glutamine and/or compounds intended to reduce the amount of fetal bovine serum (FBS) in the medium, such as a combination of insulin, transferrin, selenium, and ethanolamine, commercially available under the name ITS-X from Thermo Fisher Scientific Inc., Waltham, Mass. USA. A "culture medium" is, in some embodiments, preferably serum-free. A "culture medium" in aspects of this invention may be a defined medium, but may also comprise animal serum components. In other preferred embodiments of aspects of this invention, the medium may comprise an animal serum. In other preferred embodiments of aspects of this invention, the medium is preferably animal serum-free. The use of media with serum, or serum-free media can depend on the phase of differentiation and the status of the myogenic cell in a method of this invention.

A "culture medium" in aspects of this invention may comprise feeder cells. Preferably mouse fibroblast feeders or immortalized human skin fibroblast feeder cells are used. In alternative preferred embodiments, a feeder layer-free medium may be preferred.

The term "FGF pathway activator", as used herein, refers to a compound that can increase or enhance the activity of the FGF pathway. The FGF pathway is defined and described in the art, such as for instance in Lee et al., *Science,* 245:57-60 (1989); Mignatti et al., *J. Cell Physiol,* 151:81-93 (1992); Miller et al., *Cell Mol. Life Set,* 58:1045-1053 (2001); Sorensen et al., *Bioessays.,* 28:504-514 (2006); Coulson, *J. Prog. Brain Res.,* 146:41-62 (2004); Miki et al., *Proc. Natl. Acad. Sci. USA,* 89:246-250 (1992); Gringel et al., *J. Biol. Chem.,* 385:1203-1208 (2004); Ornitz et al., *Genome Biol.,* 2:1-12 (2001); Huang et al., *Annu. Rev. Biochem.,* 72:609-642 (2003); and Rabizadeh et al., *Cytokine Growth Factor Rev.,* 14:225-239 (2003). The FGF pathway activator is preferably human basic fibroblast growth factor (FGF2).

Figure 3:
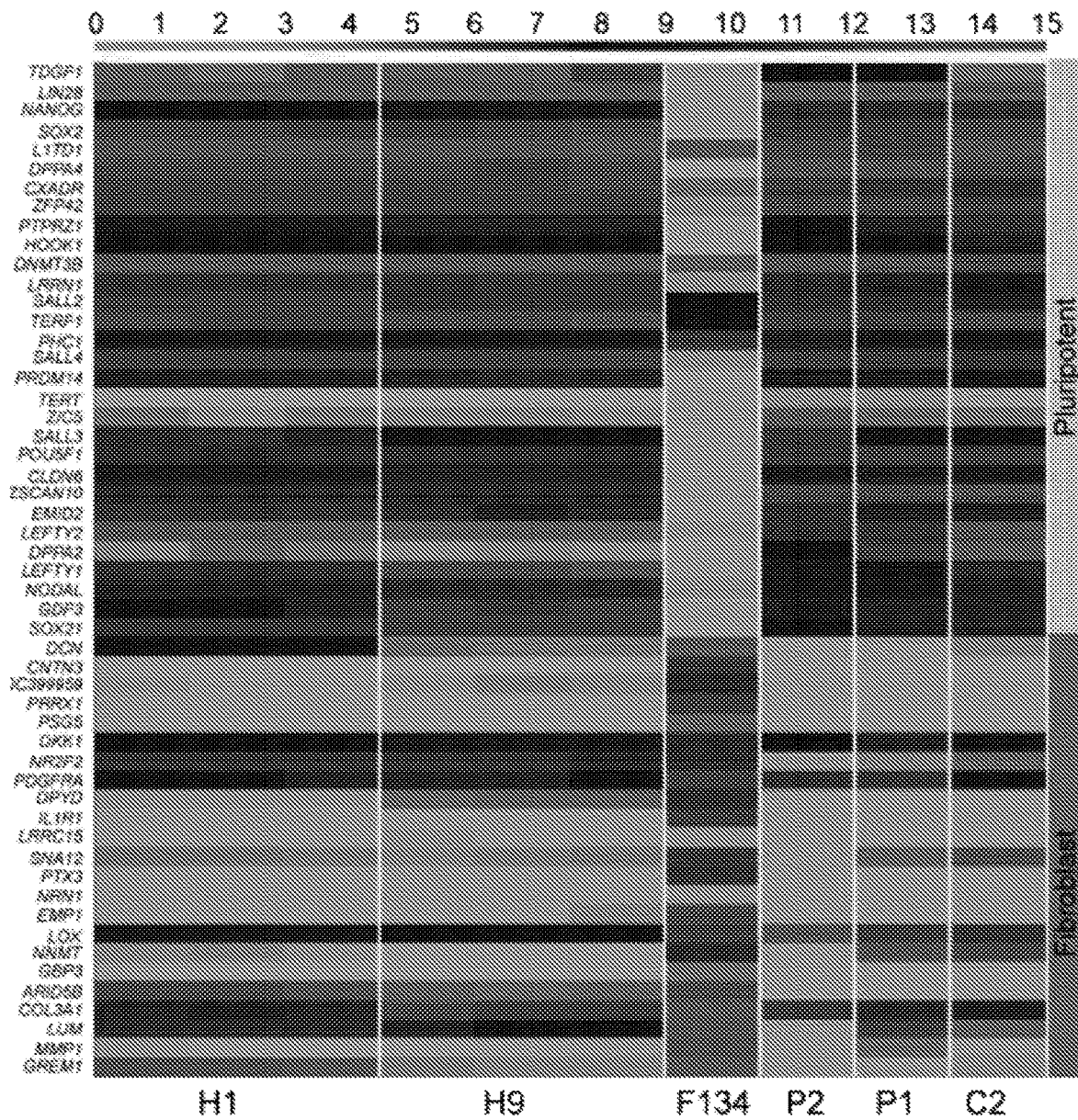
FIG. 3 shows the result of a microarray analysis of mRNA expression of pluripotency and fibroblast genes. The iPS cell are marked as P2 (patient #2), P1 (patient #1) and C2 (control #2). For comparison purposes, human embryonic stem cell lines H1 and H9 and fibroblast line F134 were also analyzed. The figure demonstrates that the iPS cell lines used herein showed marked expression of essential pluripotency genes, comparable to hES lines H1 and H9 and, in addition, showed reduced expression of fibroblast-associated genes.

The term "pluripotent stem cell", as used herein, refers to a cell with the capacity to differentiate to cell types characteristic of all three germ layers (endoderm, mesoderm and ectoderm; see also FIG. 3). Pluripotent stem cells can be characterized by expression of pluripotency markers, such as NANOG, OCT4, SSEA4, TRA-1-81 and TRA-1-60. It will be understood that the characterization of a pluripotent stem cell can be based on the characteristic expression of markers other than NANOG, OCT4, etc. The term pluripotent stem cell includes reference to iPS cells and embryonic stem (ES) cells. Preferably, the pluripotent stem cell is human, preferably the pluripotent stem cell is an iPS cell.

The term "Wnt agonist", as used herein, refers to a compound that activates Wnt signaling. In particular, such activation can promote paraxial mesoderm differentiation of a pluripotent stem cell. Examples of Wnt agonists include, but are not limited to 681665 Wnt agonist (EMD Millipore, Millipore Corp, Billerica, Mass., USA), Wnt agonist sc-222416 (Santa Cruz Biotechnology), or small molecule agonists as described, for example in Liu al., *Angew Chem Int Ed Engl,* 18:44(13):1987-90 (2005). Also foreseen is the use of the natural ligands Wnt1, Wnt2, Wnt2B, Wnt3, Wnt3A, Wnt4, Wnt5A, Wnt5B, Wnt6, Wnt7A, Wnt7B, Wnt8A, Wnt8B, Wnt9A, Wnt9B, Wnt10A, Wnt10B, Wnt11, Wnt16. Other Wnt agonists are R-spondin 1-4, Lgr4-6 and/or norrin. Preferred Wnt agonists are Wnt3A, Rspondin-1 and/or Rspondin-3.

The term "GSK3B inhibitor", as used herein refers to a compound that inhibits the Glycogen Synthase Kinase 3B enzyme, a proline-directed serine-threonine kinase. Preferably, GSK3B inhibitors activate the Wnt pathway, and may inter alia include CHIR99021, BIO, 3F8, A107022, AR-A 014418, BIO-acetoxime, CHIR 99021 trihydrochloride, 10Z-Hymenialdisine, Indirubin-3'-oxime, Kenpaullone, L803, L803-mts, Lithium carbonate, NSC 693868, SB 216763, SB 415286, TC-G 24, TCS 2002, TCS 21311, and TWS 119 (as available from Tocris Bioscience, Bristol, UK). Preferably, the GSK3B inhibitor is CHIR99021, also known as 6-[[2-[[4-(2,4-Dichlorophenyl)-5-(5-methyl-1H-imidazol-2-yl)-2-pyrimidinyl]amino]ethyl]amino]-3-pyridinecarbonitrile.

The term "induced pluripotent stem (iPS) cell", as used herein, refers to a type of pluripotent stem cell that can be generated directly from an adult somatic cell such as a fibroblast cell, by inducing expression of specific genes. The term encompasses pluripotent cells, that, unlike embryonic stem cells, are derived from differentiated somatic cells, that is, cells other than a gamete, germ cell, gametocyte or undifferentiated stem cell, that has a narrower, more defined or limited differentiation potential and that in the absence of experimental manipulation could not give rise to all types of cells in the organism. The differentiated somatic cells can be induced or reprogrammed to become iPS cells. The original set of reprogramming factors (also dubbed Yamanaka factors) are the genes Oct4, Sox2, cMyc, and Klf4. iPS cells are morphologically similar to ES cells, having a round shape, large nucleolus and scant cytoplasm. Colonies of iPS cells are similar to colonies of ES cells. In addition, iPS cells preferably express one or more key pluripotency markers measurable by a person skilled in the art, including, but not limited to, NANOG, OCT4, SSEA4, TRA-1-81 and TRA-1-60.

The term "subject", as used herein, refers to a vertebrate, preferably a mammal, more preferably a human.

The term "muscular disorder" or "muscle disorder", as used herein, refers to a disease or disorder that affects the muscle, preferably skeletal muscle, system. Such disorders include muscular dystrophy including duchenne muscular dystrophy, myotic dystrophy, limb-girdle dystrophy and facio-scapulo-humeral dystrophy; congenital muscular dystrophies; congenital myopathies; distal myopathies; myotonic syndromes; ion channel muscle diseases; malignant hyperthermias; metabolic myopathies; hereditary cardiomyopathies; congenital myasthenic syndromes; motor neuron diseases; hereditary ataxias; hereditary motor sensory neuropathies (HMSN); hereditary paraplegias. Fibromyalgia; ALS; myasthenia gravis; and Pompe disease are also included in this term. It is further noted that all specific muscular disorders individualized in the gene table of Kaplan et al., *Neuromuscular Disorders* 24:1123-1153 (2014) are referenced herein.

The term "culture", as used herein, refers to a cell culture. The cells that form the culture may be isolated or comprised in a culture medium.

The term "negative", in the context of a cell being negative for a myogenesis marker such as, e.g., Pax7, means that the expression of the gene product or protein product of the marker is absent or below a set threshold, especially and preferably in comparison to or normalized to the expression levels of control or so-called "housekeeping" genes, such as GAPDH, or may be normalized using e.g. actin as an internal control. The term "negative" in the context of a population of cells that is negative for a myogenesis marker such as, e.g. Pax7, may also refer to the fact that less than 30%, preferably less than 20%, 10%, 5%, 4%, 3%, 2% or 1% of the cells in a cell population express the indicated marker. Levels of expression of markers can be determined quantitatively or semi-quantitatively. A suitable, but by no means limiting method, is by immunocytochemical staining of cell proteins. The skilled person is well aware of method and means for assessing and ascertaining the presence or absence of such myogenesis markers. Those of skill in the art will recognize that known methods of immunofluorescent, immunochemical, polymerase chain reaction, in situ hybridization, Northern blot analysis, chemical or radiochemical or biological methods can readily ascertain the presence or absence of myogenesis markers.

The term "positive", in the context of a cell being positive for a myogenesis marker such as, e.g. MyoD, means that expression of the gene product or protein product of the marker is present and detectable and/or above a set threshold, especially and preferably in comparison to or normalized to the expression levels of control or so-called "housekeeping" genes, such as GADPH, or may be normalized using e.g. actin as an internal control. The term "positive" in the context of a population of cells that is positive for a myogenesis marker such as, e.g. MyoD, may also refer to the fact that more than 30%, preferably more than 40%, 50%, 60%, 70%, 80%, 90%, 95%, 96%, 97%, 98% or 99% of the cells in a cell population express the indicated marker. Preferably, in the context of a population of expanded myogenic progenitor cells of the invention, the cells that are positive for MyoD are also negative or Pax7. In the context of the invention, MyoD expression is preferably non-trangenic.

The term "myotube", as used herein, refers to a skeletal muscle fiber formed by the fusion of differentiated myogenic cells. Differentiation of myoblasts into myotubes is evidenced by increased fusion index, increased number of nuclei per myotube, and/or increased mRNA and protein expression of myogenic markers including myogenin and myosin heavy chain. Myosin heavy-chain expression may be determined by immunostaining using the MF20 monoclonal antibody by methods well known in the art. A fusion index (%) may be determined by dividing the number of nuclei within multinucleated myotubes by the total number of nuclei analyzed.

The term "myofiber", as used herein, refers to a matured myotube that is contractible inter alia due to the presence of titin, sarcomeres, nicotinic acetylcholine receptors and/or calcium channels. Myofibers are preferably further characterized by the presence of a basal lamina. In some instances, when reference is made to myotubes that are matured in that they are contractible, reference to myofibers is intended.

The term "function", as used in the context of the function of myogenic cells for modulation by a test compound, refers to parameters such as parameters of a muscle disorder, which can include parameters related to gene expression, protein expression and/or symptoms related to a muscle disorder. Alternatively, the function of normal or healthy myogenic cells, myotubes, or intermediate myogenic cell or cell structure of the invention may be assessed by test compounds, for example for studying the general effect of a compound on normal or healthy myogenic cells, myotubes or a myogenic cell or cell structure that is intermediate to a myogenic cell or myotube of the invention.

DESCRIPTION OF THE PREFERRED EMBODIMENTS

A method for the generation of human skeletal muscle cells from pluripotent stem cells according to the present invention comprises, as a first step, the step of providing a pluripotent stem cell.

A method for the generation of human skeletal muscle cells from pluripotent stem cells according to the present invention comprises, as a second step, the step of generating a cell culture comprising myogenic progenitors cells by culturing a pluripotent stem cell with (i) a Wnt agonist and/or a glycogen synthase kinase 3 beta (GSK3B) inhibitor, and (ii) an FGF pathway activator. This step comprises differentiating the PSC cell lines into myogenic progenitors using a specific differentiation protocol.

A method for the generation of human skeletal muscle cells from pluripotent stem cells according to the present invention further comprises, as a third step, the step of isolating from said cell culture comprising myogenic progenitors cells a C-Met+ and Hnk1− myogenic progenitor cell to thereby provide a myogenic cell lineage.

A method for the generation of human skeletal muscle cells from pluripotent stem cells according to the present invention further comprises, as a fourth step, the step of expanding said isolated C-Met+ and Hnk1− myogenic progenitor cell in a culture medium comprising an FGF pathway activator to thereby provide an cell culture of expanded C-Met+ and Hnk1− myogenic progenitor cells. This cell culture of expanded myogenic progenitor cells provides for very high numbers of myogenic cells that maintain their myogenic potential.

A method for the generation of human skeletal muscle cells from pluripotent stem cells according to the present invention further comprises, as an optional fifth step, the step of differentiating the expanded myogenic progenitor cells to form differentiated human skeletal muscle cells and/or myotubes, and optionally allowing said myotubes to mature to muscle fibers.

Provision of Pluripotent Stem Cells

A method for the generation of human skeletal muscle cells from pluripotent stem cells according to the present invention comprises, as a first step, the step of providing a pluripotent stem cell.

In order to produce pluripotent stem cells (PSCs), such as e.g. iPSCs, the skilled person is aware of a multitude of viral and non-viral methods, including methods using adenovirus, plasmids, or excision of reprogramming factors using Cre/LoxP or piggyBAC transposition, methods using episomal vectors derived from the Epstein-Barr virus, or methods using a minicircle DNA vector (US Patent Publn. 2015/0183141). The vector comprises one or a plurality of sequences encoding reprogramming factors. In some embodiments the vector comprises a plurality of reprogramming factor-coding sequences, where the combination of factors present on the single vector is sufficient to induce pluripotency. The plurality of coding sequences may be operably linked to a single promoter, where coding sequences are separated by self-cleaving peptide sequences. A non-limiting example of factors sufficient to reprogram a somatic cell to pluripotency is: Oct4, Sox2, Lin28, and Nanog. An alternative non-limiting example of factors sufficient to reprogram a somatic cell to pluripotency is: Oct4, Sox2, c-Myc, and Klf4. In some embodiments, the vectors are optimized to remove expression-silencing bacterial sequences, where in many embodiments the vectors include a unidirectional site-specific recombination product sequence in addition to an expression cassette. In other methods of the invention, a population of human somatic cells is contacted with a cocktail of reprogramming factors, and maintained in a culture medium for a period of time sufficient to reprogram said human somatic cells to pluripotency. Methods of producing PSCs, such as e.g. iPSCs, are described in detail in for instance U.S. Pat. Nos. 8,058,065; 8,129,187; 8,211,697; 8,257,941; 8,278,104; 8,546,140; 8,791,248; 9,175,268; U.S. Patent Publn. Nos. 2008/0003560; 2008/0233610; 2010/0184227; 2013/0029866; 2013/0040302; 2013/0130387; EP 2 072 618 A1; WO/2009/032194; WO/2009/032456; WO/2010/042490; and WO/2010/077955, the contents of which are incorporated herein by reference in their entirety.

Any and all methods for generating PSCs are considered to be suitable for use in aspects of this invention and their inclusion herein is expressly foreseen. Such methods include lentiviral methods, retroviral methods, methods using Sendai virus, methods using protein transduction/nucleofection, as well as the method referred to as the iTOP method (D'Astolfo et al., 2015. Cell. Vol 161(3):674-90).

For reprogramming of somatic cells, in order to produce PSCs, such as e.g. iPSCs, certain aspects of the present methods may involve using the reprogramming factors sufficient to convert the somatic cell to a pluripotent stem cell when such factors are expressed in the somatic cell under appropriate cell culture conditions. For example, the reprogramming factor(s) can comprise one or more selected from the group consisting of Sox, Oct, Nanog, Lin-28, Klf4, C-myc, L-myc and SV40LT, for example, a set of Sox, Oct, Nanog, and optionally Lin-28, a set of Sox, Oct, Klf4, and optionally C-myc, or a combination of these factors. In certain aspects, to reduce the potential toxic effect of C-myc expression, the SV40 large T gene (SV40LT) may be included with c-Myc. In certain aspects to further improve reprogramming efficiency, Myc mutants, variants or homologs that are deficient in transformation may be used. Non-limiting examples include a Myc proto-oncogene family member such as LMYC (NM-001033081), MYC with 41 amino acid deleted at the N-terminus (dN2MYC), or MYC with mutation at amino acid 136 (W136E).

In certain aspects, the somatic cells for use in embodiments according to the invention are primary human cells, which are cells directly obtained from a living human subject, and may exclude the use of an established or immortalized cell line. Some aspects can comprise the use of terminally differentiated human cells. Non-limiting examples of the primary human cell include a fibroblast, a keratinocyte, a hematopoietic cell, a mesenchymal cell, an adipose cell, an endothelial cell, a neural cell, a muscle cell, an epithelial cell, a mammary cell, a liver cell, a kidney cell, a skin cell, a digestive tract cell, a cumulus cell, a gland cell, a pancreatic islet cell or cells present in urine, saliva (e.g. of the salivary gland), sputum or in snot. More specifically, the primary human cell may be a hematopoietic progenitor cell, such as a CD34+ cell. The primary human cell may be obtained from a blood sample, a hair sample, a skin sample, a saliva sample, a solid tissue sample or any sources known to a person of ordinary skill in the art. In preferred aspects of the present invention, use may suitably be made of dermal fibroblasts obtained via skin biopsy as the somatic cells that are reprogrammed. In other embodiments of aspects of this invention, use can be made of any and all cell types amenable to reprogramming into a pluripotent stem cell, including, but not limited to cells from diseased patients, as well as cells from healthy subjects, including fibroblasts, keratinocytes, cells from blood, cells from urine, cells from salivary fluid, cells from a muscle biopsy, pericytes, mesoangioblasts, lymphocytes, teeth cells, hair cells, etc.

In certain aspects, culturing cells under reprogramming conditions comprises culturing the cells in a reprogramming medium. For example, a reprogramming medium may comprise one or more signaling inhibitor(s) (e.g., an inhibitor that has been added to the medium). The signaling inhibitors may be one or more selected from the group consisting of a glycogen synthase kinase 3ß (GSK-3ß) inhibitor, a mitogen-activated protein kinase kinase (MEK) inhibitor, a transforming growth factor beta (TGF-ß) receptor inhibitor, leukemia inhibitory factor (LIF), and a combination thereof. Particularly, the reprogramming medium can comprise a combination of GSK-3ß inhibitor, MEK inhibitor, TGF-ß receptor inhibitor, and optionally, LIF. In aspects of this invention, suitable cultivation conditions for reprogramming further include cultivating cells in a medium wherein cells are subjected to the 2i/LIF condition of dual inhibition (2i) of mitogen-activated protein kinase signaling and glycogen synthase kinase-3 (GSK3) with leukaemia inhibitory factor (LIF). The medium may further comprise externally added ROCK inhibitor or Myosin II inhibitor. The ROCK inhibitor may be HA-100 and/or Y-27632 dihydrochloride. The medium in aspects of the present invention further comprises as a supplement fibroblast growth factor (FGF2). In certain aspects, the medium of the present invention may be a chemically defined medium. Non-limiting examples of a chemically defined media include mTeSR™1 or TeSR™-E7™ (STEMCELL Technologies SARL, Grenoble, France), Dulbecco's Modified Eagle's Medium (DMEM; ATCC® 30-2002), NBF medium (DMEM/F12 supplemented with N2, B27, and basic fibroblast growth factor; Liu et al., 2006, Biochem. Biophys. Res. Comm. 346(1):131-139), Essential 8™ medium (Thermo Fisher Scientific Inc.), Primate ES Cell Medium (ReproCELL, Inc., Yokohama, Japan), and derivatives thereof. Further methods for reprogramming of somatic cells are detailed in U.S. Patent Publn. 2011/0104125, incorporated herein by reference in its entirety.

In still further aspects, methods according to the embodiments comprise culturing cells in the presence of feeder cells, such as irradiated, or mitomycin C-treated, mouse embryonic fibroblast (MEF) feeder cells. Alternatively, cells may be cultured in conditions essentially free of feeder cells. For example, a method according to the invention may comprise culturing cells in the presence of a matrix component to replace feeder cells to support culture of the cell population. Such a matrix component for cell adhesion can be any material intended to attach stem cells or feeder cells (if used). Non-limiting examples of the matrix component include collagen, gelatin, poly-L-lysine, poly-D-lysine, vitronectin, laminin, and fibronectin and mixtures thereof, for example, Matrigel™ and lysed cell membrane preparations.

In a particular example, the matrix composition includes a fibronectin fragment, such as RetroNectin® (see, e.g., U.S. Pat. Nos. 5,686,278; 6,033,907; 7,083,979 and 6,670,177, incorporated herein by reference in their entirety).

In some aspects, culturing of cells under reprogramming conditions comprises culturing the cells for at least from about one day, one week or one month under reprogramming conditions. For example, the cells can be cultured in a reprogramming medium (e.g., a medium comprising signaling inhibitors as described above) for at least or about 1, 2, 3, 4, 6, 7, 8, 9, 10, 11, 12, 13, 14, 15, 16, 17, 18, 19, 20, 25, 30, or 35 days or more, or any range derivable therein.

In yet further aspects of the embodiments culturing the cells under reprogramming conditions may further optionally comprise selecting or screening the cells for the presence of pluripotency markers or differentiation markers. For example, the cells can be selected or screened by fluorescence activated cell sorting (FACS), magnetic activated cell sorting (MACS) or flow cytometry. Alternatively or additionally, the cells may comprise a drug resistance marker and the cells can be selected by addition of an appropriate drug to the cell culture medium (e.g., puromycin). Accordingly, in certain aspects, culturing the cells under reprogramming conditions comprises culturing the cells in a reprogramming medium. For example, cells can be cultured about 1 to 10 days (e.g., about 1 to 2 days, 1 to 3 days or 1 to 5 days). Likewise, in certain aspects, the cells are cultured for at least about 1 to 10 days, such as for about 5, 10, 15, 20, 25, 30 or more days. Cells may be cultured at least until PSCs are produced.

In yet a further aspect, the methods of the embodiments may further comprise selecting PSCs, for example, based on one or more embryonic cell characteristics, such as an ES cell-like morphology. Thus, in still further embodiments, a method comprises selecting pluripotent cells based on the expression of at least a first marker of pluripotency. For example, a population of cells that express at least a first marker of pluripotency (e.g., Tra-1-60) can be isolated by picking of a clonal cell colony or by FACS. The pluripotent population can optionally be further separated as required.

In further aspects of the embodiments, a method of the invention comprises the step of culturing the pluripotent stem cells under expansion conditions. For example, after reprogramming (and/or screening or selection), the cells are subjected to expansion conditions, such as by culturing in an expansion medium. The expansion medium may, for example, be essentially free of externally added GSK-3 inhibitor, MEK inhibitor, and TGF-ß receptor inhibitor. In certain aspects, the expansion medium may have one or more of the signaling inhibitors and/or (recombinant) leukemia inhibitory factor (LIF) to prevent differentiation. Examples of suitable expansion media include, but are not limited to, any of the media for cell reprogramming described above, normal ES cell culture medium (DMEM supplemented with 15% FBS, 0.1 mM non-essential amino acids, 0.1 mM 2-mercaptoethanol, 2 mM Glutamine, 100 U/ml penicillin/streptomycin and 1000 U/ml LIF).

Unless otherwise specified, all percentages herein are by weight and refer to the weight of the compositions.

The culture media used in aspects of this invention may comprise animal serum (e.g. fetal bovine serum) or other animal derived products to permit the desired proliferation during culturing. The presence of animal derived products in PSC culture media may however be undesired for in vivo application of the cells. In order to avoid the presence of toxic proteins or immunogens that evoke an immune response in the recipient and avoid the risk of contamination by animal pathogens, such as viruses, *mycoplasma* and prions, which can pose a serious health risk in cell therapy and other clinical applications, animal derived products in the culture media can be replaced by serum replacement compounds, serum-free media or xeno-free serum replacement media can be used. Several xeno-free serum replacements and media are currently available (X-Vivo 10, X-Vivo 20, SSS, Lipumin, Serex, Plasmanate, SR3). These serum replacements often are specifically formulated to support the culture of a single cell type. Suitably, in a xeno-free serum replacement formulation used in aspects of this invention, retinol may be used in a concentration of about 0.1 µM to about 50 µM, preferably about 10 µM to about 40 µM, and more preferably about 20 µM. As an alternative, or in combination with any of the above, as a serum replacement, Knockout™ SR medium (Invitrogen™, Thermo Fisher Scientific Inc., Carlsbad, Calif., USA), or Ultroser G (Pall Corporation, Port Washington, N.Y., USA may be used.

In still a further aspect a method of the invention may optionally comprise the step of characterizing the expanded PSCs. For example, characterizing the PSCs can comprise detecting one or more pluripotency markers; performing a karoytype analysis; detecting the presence of a nucleic acid molecule; determining the sequence of a nucleic acid molecule; detecting the presence of the extra-chromosomal genetic element; teratoma formation analysis; epigenetic analysis; RNA expression analysis; protein expression analysis; or small tandem repeat (STR) detection.

In certain aspects, starting cells for the present methods may comprise at least or about $10^4$, $10^5$, $10^6$, $10^7$, $10^8$, $10^9$, $10^{10}$, $10^{11}$, $10^{12}$, $10^{13}$ cells or any range derivable therein. The starting cell population may have a seeding density of at least or about 10, $10^1$, $10^2$, $10^3$, $10^4$, $10^5$, $10^6$, $10^7$, $10^8$ cells/ml, or any range derivable therein.

Embodiments discussed in the context of methods and/or compositions of the invention may be employed with respect to any other method or composition described herein. Thus, an embodiment pertaining to one method or composition may be applied to other methods and compositions of the invention as well.

In Vitro Differentiation of PSC Cells to Myogenic Cells

A method for the generation of human skeletal muscle cells from pluripotent stem cells according to the present invention comprises, as a second step, the step of generating a cell culture comprising myogenic progenitors cells by culturing the pluripotent stem cell with (i) a Wnt agonist and/or a glycogen synthase kinase 3 beta (GSK3B) inhibitor, and (ii) an FGF pathway activator. This step comprises differentiating the PSCs into myogenic progenitors using a specific differentiation protocol.

This protocol may, in one embodiment, comprise the steps of washing the colonies of PSCs, treating the colonies with collagenases IV, or a suitable other enzyme to liberate cells from said colonies, and suspending the cells in a pre-differentiation medium that allows for the development of the PSCs in the desired cell lineage. Preferably, PSC's are cultivated in the presence of a relatively high concentration of a GSK3B inhibitor such as CHIR99021. The amount of the GSK3B inhibitor in the pre-differentiation medium is preferably higher than 3 µM, more preferably at least 3.2 µM or at least 3.5, 4, 5, 6, 7, 8, 9, or 10, or 15 µM. Surprisingly, such high concentrations of GSK3B inhibitors are well tolerated by PSCs of the present invention and resulted in the generation of Pax7-positive cells in more than 35 independent differentiation experiments, indicating very reproducible production of a myogenic cell lineage from PSCs not previously attained. Preferably, the duration of culturing in the presence of a GSK3B inhibitor is for a longer duration (e.g. 5-10 days, such as 5-6 days). This duration of cultivation in the presence of a GSK3B inhibitor is well tolerated and resulted in the generation of Pax7-positive cells in more than 35 independent differentiation experiments. Alternatively, it is envisaged herein that a production of a myogenic cell lineage, suitable for the purposes of the invention, can be obtained by culturing cells with a GSK3B inhibitor at a concentration of 2-15 µM, preferably for a period of 2-10 days.

The in vitro differentiation of PSC cells to myogenic cells further comprises a second period of culturing the cells with a FGF pathway activator, preferably FGG2, at a concentration of 5-50 ng/ml, preferably 10-30 ng/ml, more preferably about 20 ng/ml, of FGF2. Preferably, the GSk3B inhibitor is not present anymore during the second period of culturing. The second period of culturing can be variable, but is preferably between 5-20 days, preferably 10-16 days.

Preferably, the in vitro differentiation of PSC cells to myogenic cells further involves a third period of culturing with a differentiation medium that pushes the cells further into the mesoderm orientation, i.e. towards a myogenic cell lineage positive for myogenesis marker Pax3 and/or Pax7. A suitable example of such a medium is DMEM/F12, ITS-X, such as 1×ITS-X, and Penicillin/Streptomycin-Glutamine (preferably all Gibco™).

The third period of culturing is preferably 5-30 days, more preferably 10-20 days, and most preferably 14-18 days.

Isolation of Myogenic Cells

A method for the generation of human skeletal muscle cells from pluripotent stem cells according to the present invention further comprises, as a third step, the step of isolating from said cell culture comprising myogenic progenitors cells a C-Met+ and Hnk1− myogenic progenitor cell to thereby provide a myogenic cell lineage. Alternatively, or in addition, it is envisaged that the step of isolating cells, or isolated cells as such, as referred to herein, may refer to the isolation of, or to an isolated, Hnk1− and AchR+ (acetylcholine receptor) myogenic progenitor cell(s).

It is an aspect of this invention that selection and isolation of the cell lineage of interest occurs prior to expansion. Usually, FACS sorting results in crippled or damaged cells, as a result of illumination and high shear force applied in the FACS isolation. However, the present inventors found that expansion after selection can surprisingly be very beneficial in that expanded cultures of pure, isolated cells can be obtained, which provides for very homogeneous lineages of myogenic cells. The present inventors have now found that following FACS isolation, cells are preferably allowed to recover from the cell sorting conditions. This can be achieved by cultivation in the presence of, for instance, a Rho Kinase inhibitor.

One of skill in the art will readily realize that various methods may be used to isolate the required cells from the cell culture comprising myogenic progenitors cells. Suitably, fluorescence associated cell sorting (FACS) is used to isolate the required cells.

The cells most suited for providing cells for the myogenic lineage of the invention are preferably Pax7 and/or Pax3 positive cells, more preferably Pax7-positive cells. Such cells can readily be isolated by FACS using cell-surface markers C-Met+ and Hnk1− as described herein. Such isolation procedures are well known to one of skill in the art.

The cells most suited for providing cells for the myogenic lineage of the invention are preferably MyoD positive cells, indicative of activated satellite cells. Such cells can readily be isolated by FACS using anti-MyoD fluorescent antibodies.

The cells most suited for providing cells for the myogenic lineage of the invention are preferably C-Met+ and Hnk1$^-$. Cells are suitably stained by immunocytochemical staining using anti-C-MET antibodies and anti-HNK1 antibodies. Cells positive for C-MET, negative for HNK-1 and optionally stained by Hoechst 33258 viability staining are isolated, preferably by FACS, and selected for further expansion.

In principle, FACS purification can be performed starting a few days after addition of FGF in the pre-differentiation stage, which is generally around day 9. It may alternatively also be performed much later, e.g. at day 40. It is preferred that the isolation of cells positive for C-MET, negative for HNK-1, such as by FACS sorting, is performed at day 35 or later.

Expansion of Myogenic Progenitor Cells

A method for the generation of human skeletal muscle cells from pluripotent stem cells according to the present invention further comprises, as a fourth step, the step of expanding said isolated C-Met+ and Hnk1− myogenic progenitor cell in a culture medium comprising an FGF pathway activator to thereby provide a cell culture of expanded C-Met+ and Hnk1− myogenic progenitor cells. This cell culture of expanded myogenic progenitor cells provides for very high numbers of myogenic cells that maintain their myogenic potential.

The concentration of the FGF pathway activator in the expansion medium for growing the isolated C-Met+ and Hnk1$^-$ myogenic cell is suitably 25-200 ng/ml, preferably 70-150 ng/ml, more preferably 90-110 ng/ml, most preferably about 100 ng/ml. Preferably, the FGF pathway activator is FGF2.

Expansion of isolated C-Met+ and Hnk1$^-$ myogenic progenitor cells, such as isolated by FACS, is performed in an expansion medium preferably using DMEM high glucose (Gibco™) as a basic medium component. The expansion medium is preferably supplemented with 100 U/ml Penicillin/Streptomycin/Glutamine (Life Technologies). As a further supplement the expansion medium is preferably supplemented with 10% fetal bovine serum (such as from Hyclone, Thermo Scientific). The expansion medium is preferably supplemented with 100 ng/ml of FGF pathway activator, preferably FGF2 (such as from Prepotech Inc.). Expansion of isolated myogenic progenitor cells, preferably when isolated by FACS, in the first stage of expansion, i.e. prior to the first passage, and preferably also during subsequent passages, is preferably performed using a medium comprising a Rho Kinase inhibitor (ROCK inhibitor). Suitable Rho Kinase inhibitors include RevitaCell™ Supplement (Gibco™), HA-100, Y-27632 dihydrochloride and Thiazovivin or a combination thereof. RevitaCell™ Supplement is preferred.

The process of expansion can be performed on a single, isolated myogenic cell or on a plurality of isolated myogenic cells. Preferably, the expanded myogenic progenitor cells are clonal cells, meaning that they are derived from a single PSC cell or clone. This ensures that such cells are genetically identical. It is an advantage of this invention that clonal populations can now be provided at a level suitable for drug screening/regenerative therapy scale ($10^4$, $10^5$, $10^6$, $10^7$, $10^8$, $10^9$, $10^{10}$, $10^{11}$, $10^{12}$, $10^{13}$ cells or more in totality in a single culture. The population of cells according to this invention does not need to be clonal, but can also be started by isolating 2-50,000 cell separately. Preferably the starting cell population is $10^4$, $10^3$, $10^2$, 10, or 1 isolated progenitor lineage cell Upon successive passages in the expansion medium, the selected and expanded cells of this invention maintain their MyoD expression, whereas Pax7 expression decreases during expansion cultivation. Preferably, at least 50%, 60%, 70%, 80%, more preferably at least 90%, of cells in a cell culture of the invention is negative for Pax7 following, preferably the $3^{rd}$, $4^{th}$, $5^{th}$, $6^{th}$, or even higher passage of the cells.

Preferably, colonies are passaged using the trypsin replacement enzyme system TrypLE™, which products are animal origin-free cell dissociation enzymes that have been shown to maintain normal karyotypes and high cell viability of hESCs after at least 20 consecutive passages.

Preferably, the expansion is continued for at least 5, 6, or 7, preferably 8, 9 or more passages. During such passages, the MyoD expression in the expanded cells will essentially be maintained, whereas Pax7 expression is gradually decreased.

Upon testing different expansion media, it was found that certain media were preferred when C-Met+ and Hnk1$^-$ myogenic progenitor cells were isolated by FACS.

Expansion of Myogenic Progenitor Cells

| Expansion medium | Ability to expand C-MET-positive cells* |
|---|---|
| DMEM HG/10% FBS/PSG/100 ng/ml bFGF | Yes |
| HAM F10/20% FBS/PSG | Poorly |
| HAM F10/20% FBS/PSG/100 ng/ml bFGF | Poorly |
| DMEM HG/10% FBS/PSG | Poorly |

*Hoechst 33258/C-MET-positive cells were plated at 40,000 cells/well on extracellular matrix ( ) (E6909 Sigma-Aldrich Co.)-coated 48 wells plates in iPS-myogenic progenitor proliferation medium containing FGF2 at 100 ng/ml. Cells were passaged using 2x diluted TrypLe.
DMEM HG (high glucose): cat: BE12-604F/U1, Lonza;
HAM F10: cat: BE02-014F, Lonza;
FBS: fetal bovine serum:
HyClone cat: SV30160.03 Thermo or S1810-500, Biowest;
PSG: penicillin, streptomycin, glutamine, cat 10378-016, Gibco ™.

Hence, when FACS isolation is used to isolate C-Met+ and Hnk1$^-$ myogenic progenitor cells, the expansion medium used in methods of the invention preferably comprises DMEM HG, 10% of FBS, and about 100 ng/ml of FGF pathway activator. In one aspect, the present invention provides a cell culture medium for the expansion the expansion medium comprising DMEM comprising an amount of 100 ng/ml FGF2, 10% of an animal serum, preferably FBS, or serum replacement factor. More preferably, the expansion medium of the invention comprises a ROCK inhibitor in a concentration supporting the expansion of FACS isolated cells. The medium may further comprise a penicillin/streptomycin/glutamine supplement.

The cell culture of myogenic cells of the invention obtained through the expansion protocol described herein above is an aspect of this invention. Such a cell culture is characterized in that it is a cell culture of expanded C-Met+ and Hnk1− myogenic progenitor cells, which cells exhibit stable MyoD expression while exhibiting decreased Pax7 expression upon successive passages. Pax7 expression in an expanded myogenic cell culture of the present invention is preferably such that less than 50%, preferably less than 40%, more preferably less than 30%, 25%, 20%, 15%, 10%, or 5% of the cells in said culture are positive for Pax7. Preferably, such low levels of Pax7 positive cells in cultures of this invention are attained after at least 2, 3, 4, 5, 6, 7, 8, 9, or 10, or more successive passages.

The expanded cell culture of myogenic cells according to the present invention can be in frozen form. The expanded cells are preferably taken up in a cryopreservation medium when they are frozen. Suitable cryopreservation media or methods of cryopreserving human stem cells are described in the art, such as for instance in US 20050026133 A1 or WO 2005118785 A1. It follows from the above that the present procedure to obtain a cell culture of the invention is preferably transgene-free.

It further has appeared that the cell culture, harbouring the expanded cells as produced by the above described method can be differentiated from similar cells in the prior art. To this extent the gene expression profile of the cells as produced according to the above method were compared with the expression profile of cells as described by Choi et al. Cell reports, 15:2301-2312, 2015). In this article Choi and co-workers have described the expression profile of hiPSC-derived myoblasts from patients with Duchenne muscular dystrophy and control subjects. This is the only publication to date where expression profiles of PSC-derived myoblasts have been described. A comparison of the expression profiles of those cells with the cells as produced in the present method revealed significant differences in the expression of genes that are thought to play an important role in myoblast formation and expansion (Bressi, S. et al., Developm. Biol. 304:633-651, 2007).

It appeared that the cells as produced by the present method showed no or little expression of the genes listed in table 4, while the cells reported by Choi et al. were expressing all of these genes. Other genes were expressed in all cells, but for the genes CTGF, COL6A3, COL5A1, COL1A1, COL6A1, LAMB1, TGFBR2 a relatively high expression level was found in the cells of the present invention where the cells of Choi et al. had a relatively low expression (see FIG. 16). For the genes MATN2, CDH4, VCAM1, NFATC4, JAG1, FST, NOTCH1, NFIX the opposite effect was observed (see FIG. 16).

Accordingly, the cell culture of the present invention may also be characterized as having cells that have a relatively high expression level of one or more of the genes selected from the group of CTGF, COL6A3, COL5A1, COL1A1, COL6A1, LAMB1 and TGFBR2, and/or a relatively low expression level of one or more of the genes selected from the group of MATN2, CDH4, VCAM1, NFATC4, JAG1, FST, NOTCH1 and NFIX. Also, the cells in the cell culture of the present invention may be characterised as substantially lacking the expression of one or more, preferably at least 5, more preferably at least 10, most preferably all of the genes selected from the group of ARX, CD34, CITED1, FGF4, FGF5, FGF6, FGF9, FOXC1, ITGA9, *LAMA*4, MEOX1, SEMA3D, SEMA4G, SMAD6, TCF15, and UNCX.

Differentiating Myogenic Cells into Myotubes

A method for the generation of human skeletal muscle cells from pluripotent stem cells according to the present invention further comprises, as an optional fifth step, the step of differentiating the expanded myogenic progenitor cells to form differentiated human skeletal muscle cells and/or myotubes, and optionally allowing said myotubes to mature to muscle fibers.

In order to produce myotubes from myogenic cells of the invention, one may use any one of the classical techniques for induction of terminal differentiation, e.g. by deprivation of serum in the medium, such as described by Yoshida et al. (J Cell Science 111, 769-779 (1998)), through formation of PSM-like cells as described in Chal et al. (Nature Biotechnology 33, 962-969 (2015)), or using the two-dimensional muscle syncytia (2DMS) technique of Yamamoto et al. (J Histochem Cytochem. 56(10): 881-892 (2008)), all incorporated herein by reference). To induce differentiation, cells may be seeded at a density of about $1\text{-}10\times10^4$ cells/well (12-24 well plate) in growth medium (e.g. DMEM supplemented with 10% fetal calf serum (FCS) and 60 µg/ml of kanamycin) and then 24 hours later switched to ITS serum-free medium (DMEM supplemented with 10 µg/ml of insulin, 5 µg/ml of transferrin, 10 nmol of sodium selenite, 1 mg/ml of bovine serum albumin (BSA) and 60 µg/ml of kanamycin). The medium is then routinely changed every 24 hours. Upon serum deprivation, many of the cells will show differentiation by virtue of continued expression of MyoD and de novo expression of myogenin, the earliest known event of terminal differentiation marking irreversible commitment, while non-differentiating cells down-regulate MyoD-expression. The skilled person understands that expression of myogenesis markers in an expanded culture of myogenic cells according to the invention can change when differentiating these cells in e.g. end-structures such as myotubes. For instance, Pax7 expression, which is decreased or preferably absent in an expanded cell culture of the invention, may be present in newly formed stem cells such as satellite cells in the myotube structure. After terminal differentiation, this may result in a mixed population of cells consisting of myotubes and newly formed Pax7+ cells. When analyzing this mixed cell population, Pax7 may be detected in some cells but this expression is attributable to newly formed stem cells.

An important problem with differentiated myotubes is that they are often of poor quality, have a short lifespan (generally 2-4 days) and are difficult to maintain. The cells of the present invention have the advantage that they show proper maturation (thicker fibers, formation of sarcomeres, expression of neuromuscular junction), and that the myotubes can be maintained in culture for about 2 weeks. This long-term differentiation of the myogenic progenitors of the invention is preferably performed by providing a three-dimensional differentiation environment (e.g. wells coated with an extracellular matrix (ECM) protein. As an extracellular matrix (ECM) protein, one may use, for instance, extracellular matrix (ECM) gel, preferably ECM gel from Engelbreth-Holm-Swarm murine sarcoma fibrillar collagen (E6909 Sigma), and/or preferably a combination of (rat tail) collagen type I and MaxGel ECM (E0282 Sigma), and/or fibrillar collagen, and/or a component of ECM gel, and/or a synthetic mimetic of an ECM component, and/or collagen type I, or a combination thereof. The long-term differentiation of the myogenic progenitors of the invention is preferably performed by providing a high FGF2 content (e.g. around 100 ng/ml FGF2 or more) in the medium. When myogenic progenitors reach about 90% (range 60-100%) confluence, the medium is replaced with a differentiation medium, preferably having as a basis DMEM HG, DMEM LG or DMEM/F12, more preferably DMEM HG, comprising 0.2-2%, preferably about 1%, of ITS-X and one of Knockout™ serum replacement (0.5%-5%, preferably about 1%) or BSA (0.1-10 mg/ml, preferably about 0.5 mg/ml), optionally supplemented with 100 U/ml Penicillin/Streptomycin/Glutamine (Life Technologies). It is preferred that every second day 50% of the medium is replaced by fresh differentiation medium. In this context, BSA is preferably a lipid-rich BSA such as AlbuMAX® I (Gibco).

In this context, it was found that the use of about 1% ITS-X without knock out serum replacement or BSA results in impaired maturation after day 4 of differentiation. Thereafter, the fibers become thinner and eventually die off. A range of cell densities was tested at the time of start of differentiation (from 60-100% confluent). It is most preferred that cultures are around 100% confluent at the start of differentiation, such as in a preferred embodiment of a method of differentiating according to the invention.

Preferably, the knock out serum replacement is a serum-free, eukaryotic cell culture medium supplement that comprises one or more ingredients selected from the group consisting of albumins or albumin substitutes, one or more amino acids, one or more vitamins, one or more transferrins or transferrin substitutes, one or more antioxidants, one or more insulins or insulin substitutes, one or more collagen precursors, and one or more trace element. More preferably, the knock out serum replacement comprises, or is obtained by combining, Albumax® I and one or more ingredients selected from the group consisting of glycine, L-histidine, L-isoleucine, L-methionine, L-phenylalanine, L-proline, L-hydroxyproline, L-serine, L-threonine, L-tryptophan, L-tyrosine, L-valine, thiamine, reduced glutathione, L-ascorbic acid-2-phosphate, iron saturated transferrin, insulin, and compounds containing the trace element moieties $Ag^+$, $Al^{3+}$, $Ba^{2+}$, $Cd^{2+}$, $Co^{2+}$, $Cr^{3+}$, $Ge^{4+}$, $Se^{4+}$, $Br^-$, $I^-$, $Mo^{2+}$, $F^-$, $Si^{4+}$, $V^{5+}$, $Mo^{6+}$, $Ni^{2+}$, $Rb^+$, $Sn^{2+}$ and $Zr^{4+}$ Suitable examples of such supplements and media are described in US 20020076747 A1, the contents of which are herein incorporated by reference. Reference is specifically made to Tables 1-3 of US 20020076747 A1, which specify the preferred ingredients, and their concentrations, in a supplement and medium of the invention as described in US 20020076747 A1. The subject-matter in Tables 1-3 of US 20020076747 A1 are incorporated herein by reference.

The skilled person is aware of assays, commonly used in the art, to measure parameters related to functional maturation of myotubes or myofibers of the invention. Such assays can test for viability and metabolism, calcium currents and other ion channel currents, contractions, field potential, action potential, impedance and/or sarcomere length. Reference, in this context, is made to Ribeiro et al., 2015 Biomaterials, 51: 138-150.

A method for differentiating expanded myogenic progenitor cells into myotubes and/or myofibers, in aspects of the present invention, may, in a preferred embodiment, be performed as follows:
a) an ampule of a frozen population of expanded myogenic progenitor cells of the invention is thawed and cultivated in a medium containing DMEM high glucose supplemented with about 100 U/ml Penicillin/Streptomycin/Glutamine, about 10% fetal bovine serum, and about 100 ng/ml FGF2;
b) the cells are grown to about 90-100% confluency;
c) the medium is replaced by a differentiation medium of the invention, preferably comprising DMEM high glucose with about 1% ITS-X plus 0.5%-5%, preferably about 1%, of serum replacement (preferably Knockout™ serum replacement) and about 1% (or 100 U/ml) Penicillin/Streptomycin/Glutamine;
d) at least 20%, preferably 40%-60%, of the differentiation medium is refreshed every two days and the cells are allowed to form myotubes and/or myofibers. This may take several days.
Medical Uses of the Cells of the Invention Cells and fused cell structures, such as myotubes or myofibers, produced according to the methods of this invention, can be used as model systems in methods for screening of drugs for use in the treatment or prevention of skeletal muscle disorders and to study the biology of skeletal muscle disease. Alternatively, cells and fused cell structures according to this invention can be used therapeutically as a transplant material in regenerative medicine in order to restore diseased muscle. Either of these application can be combined with gene correction (gene therapy) in various ways, using lentiviral, adeno-associated viral (AAV) expression, or using gene editing, in vitro at the level of iPS or muscle cells (using CRISPR-cas9, TALENs, ZFNs, or meganucleases).

The present invention in one aspect provides an in vitro method of testing candidate medicaments and/or to test therapies in a quantitative manner. This is one of the major reasons that, as to date, very few therapies have been developed, since such potential therapies cannot be tested quantitatively in vitro.

The present invention in one aspect provides a system for in vitro modeling of a human degenerative, (neuro)muscular disorder comprising an array of cell cultures wherein each cell culture is (a population of) an expanded cell according to the present invention, (a population of) a differentiated cell of the present invention, a (population of) myotubes, or a (population of) myofibers, wherein the array is contacted with a test compound and the reaction of the (population of) cells or cell structures on said array is monitored. Suitable reactions for monitoring include GAA expression, contraction of fibers or any other desired phenotype of the cells or cell structures. In the treatment of Pompe disease, any medicament for treatment of Pompe disease may be used in combination with enzyme replacement therapy (ERT) (recombinant human GAA, myozyme) and its novel forms, and candidate medicaments identified or selected through screening methods of this invention.

The present invention in one aspect provides a method of treating neuromuscular disorders in a subject by cell-based therapy comprising the ex vivo expansion according to a method of the present invention of a cell of said subject or a compatible donor, optionally genetically altering the cell in vitro as described above, optionally expanding the cell, and applying the cell in cell-based treatment of said neuromuscular disorders.

Interestingly and advantageously, since the present invention provides for a cell culture of a population of expanded myogenic progenitor cells, in combination with a reliable method for long-term differentiation of such cells into myotubes and ultimately in myofibers, it is now also to possible to assess the effect of a muscular disorder on the maturation or differentiation of myogenic progenitor cells into myotubes and/or myofibers, by a method comprising the step of a) plating cells of a cell culture according to the invention, preferably a cell culture based on a PSC that is an induced PSC derived from a cell of a human subject suffering, or suspected of suffering, from a muscular disorder, in a well coated with extracellular matrix protein and culturing the cells in the expansion medium of the invention or a medium comprising DMEM, collagen type I rat tail and PBS; b) replacing the medium in step a) with a differentiation medium comprising, or consisting of, (i) DMEM high glucose, DMEM low glucose or DMEM/F12, (ii) about 1% of ITS-X and (iii) 0.5%-5%, preferably about 1%, of knockout serum replacement and/or 0.1-10 mg/ml, preferably about 0.5 mg/ml, of BSA; wherein, every second day, 50% of said differentiation medium is replaced by fresh differentiation medium;
c) assessing the effect of said muscular disorder on the maturation or differentiation of myogenic progenitor cells into myotubes and/or myofibers.

FURTHER EMBODIMENTS OF THE INVENTION

Embodiment 1

The present invention provides a method for culturing an isolated myogenic cell, comprising the step of
a) culturing an isolated C-Met+ and Hnk1⁻ myogenic cell in a culture medium comprising an FGF pathway activator; wherein said myogenic cell is isolated from a myogenic cell culture obtained by culturing a pluripotent stem cell (PSC) with (i) a Wnt agonist and/or a glycogen synthase kinase 3 beta (GSK3B) inhibitor, and (ii) an FGF pathway activator.

Embodiment 2

The present invention provides a method according to Embodiment 1, wherein the pluripotent stem cell (PSC) is an embryonic stem cell (ESC) or induced PSC (iPSC), preferably a human PSC (hPSC), more preferably an iPSC derived from a fibroblast of a human subject, preferably a human subject suffering from a (neuro)muscular disorder.

Embodiment 3

The present invention provides a method according to embodiment 1 or embodiment 2, wherein culturing the pluripotent stem cell comprises a first period of culturing with a Wnt agonist and/or a glycogen synthase kinase 3 beta (GSK3B) inhibitor, and a second period of culturing with an FGF pathway activator.

Embodiment 4

The present invention provides a method according to embodiment 3, wherein the duration of the first period is 1-10 days, preferably 3-8 days, more preferably 5-6 days.

Embodiment 5

The present invention provides a method according to embodiment 3 or 4, wherein the duration of the second period is 5-20 days, preferably 10-16 days.

Embodiment 6

The present invention provides a method according to any one of the previous embodiments, wherein the concentration of the glycogen synthase kinase 3 beta (GSK3B) inhibitor is between about 1-10 μM, preferably between 2-5 μM, more preferably about 3.5 μM.

Embodiment 7

The present invention provides a method according to any one of the previous embodiments, wherein the glycogen synthase kinase 3 beta (GSK3B) inhibitor is CHIR99021.

Embodiment 8

The present invention provides a method according to any of the previous embodiments, wherein the FGF pathway activator is basic fibroblast growth factor (FGF2).

Embodiment 9

The present invention provides a method according to embodiment 8, wherein the concentration of the FGF pathway activator in the culturing of the pluripotent stem cell is 5-50 ng/ml, preferably 10-30 ng/ml, more preferably about 20 ng/ml, of FGF2.

Embodiment 10

The present invention provides a method according to embodiment 8 or embodiment 9, wherein the concentration of the FGF pathway activator in culturing the isolated C-Met+ and Hnk1⁻ myogenic cell is 25-200 ng/ml, preferably 70-150 ng/ml, more preferably 90-110 ng/ml, most preferably about 100 ng/ml, of FGF2.

Embodiment 11

The present invention provides a method according to any one of the previous embodiments, wherein the culture medium further comprises fetal bovine serum (FBS), preferably in a concentration of about 10%, optionally substituted by serum replacement.

Embodiment 12

The present invention provides a method according to any one of the previous embodiments, wherein the isolated C-Met+ and Hnk1⁻ myogenic cell is passaged at least 7 times, preferably 10-20 times, more preferably about 15 times.

Embodiment 13

The present invention provides a method according to any one of the previous embodiments, wherein the C-Met+ and Hnk1⁻ myogenic cell is isolated using fluorescence activated cell sorting (FACS).

Embodiment 14

The present invention provides a culture of myogenic cells obtainable by a method according to any of embodiments 1-13.

Embodiment 15

The present invention provides a culture according to embodiment 14, wherein at least 70%, preferably at least 90%, more preferably at least 95%, of the myogenic cells are positive for myogenesis marker MyoD, while less than 50% the cells is positive for myogenesis marker Pax7.

Embodiment 16

The present invention provides a culture according to embodiment 14 or embodiment 15, wherein the culture is frozen or cryopreserved.

Embodiment 17

The present invention provides a myogenic cell of the culture of any one of embodiments 14-16.

Embodiment 18

The present invention provides a myotube or myofiber formed after terminal differentiation of the culture according to any one of embodiments 14-15 or from the cell of embodiment 17, preferably said myotube or myofiber (i) has a fusion index of at least 60%, preferably at least 70%, (ii) forms sarcomeres, (iii) expresses neuromuscular junctions, and/or (iv) shows spontaneous contraction.

Embodiment 19

The present invention provides a method for in vitro screening of a test compound for modulating the function of myogenic cells in a culture according to embodiment 14 or 15, a myotube or myofiber according to embodiment 18, a cell according to embodiment 17, or a myogenic cell or cell structure intermediate to said cell and said myotube or myofiber in terms of differentiation status, comprising the step of
a) contacting a test compound with a culture according to embodiment 14 or 15, with a myotube or myofiber according to embodiment 18, with a cell according to embodiment 17, or with a myogenic cell or cell structure intermediate to said cell and said myotube or myofiber in terms of differentiation status;
b) measuring the effect of the test compound on the function, phenotype or genotype of said cell, myotube or myofiber, or cell or cell structure intermediate.

Embodiment 20

The present invention provides for the use of the culture according to embodiment 14 or embodiment 15, the cell according to embodiment 17, the myotube or myofiber according to embodiment 18, or a myogenic cell or cell structure intermediate to said cell and said myotube or myofiber in terms of differentiation status, for screening a test compound or drug in vitro.

Embodiment 21

The present invention provides a cell according to embodiment 17, the myotube or myofiber according to embodiment 18, or a myogenic cell or cell structure intermediate to said cell and said myotube or myofiber in terms of differentiation status, for use as a medicament.

Embodiment 22

The present invention provides a cell according to embodiment 17, the myotube or myofiber according to embodiment 18, or a myogenic cell or cell structure intermediate to said cell and said myotube or myofiber in terms of differentiation status, for use in the treatment of a muscle disorder.

Embodiment 23

The present invention provides a cell, myotube, myofiber, myogenic cell or cell structure for use according to embodiment 22, for administration by transplantation.

Embodiment 24

The present invention provides a medium for culturing myogenic cells, comprising fetal bovine serum (FBS), preferably in a concentration of about 10%, and 70-150 ng/ml, preferably 90-110 ng/ml, more preferably about 100 ng/ml, of FGF2.

Embodiment 25

The present invention provides a medium of embodiment 24, wherein the medium is for culturing isolated myogenic cells, preferably myogenic cells isolated by FACS.

Embodiment 26

A method for generating human skeletal muscle cells from pluripotent stem cells comprising the steps of:
providing a pluripotent stem cell; generating a cell culture comprising myogenic progenitors cells by culturing a pluripotent stem cell with (i) a Wnt agonist and/or a glycogen synthase kinase 3 beta (GSK3B) inhibitor, and (ii) an FGF pathway activator;
isolating from said cell culture comprising myogenic progenitors cells at least one C-Met+ and Hnk1− myogenic progenitor cell, to thereby provide a myogenic cell lineage;
expanding said isolated C-Met+ and Hnk1− myogenic progenitor cell in a culture medium comprising an FGF pathway activator to thereby provide a cell culture of expanded C-Met+ and Hnk1− myogenic progenitor cells, which cells exhibit stable MyoD expression while exhibiting decreased Pax7 expression upon successive passages;
optionally allowing the expanded myogenic progenitor cells differentiate and to form differentiated human skeletal muscle cells and/or myotubes, and optionally allowing said myotubes to mature to muscle fibres.

Still further embodiments are described herein above, in the Examples, and in the claims attached hereto.

In general, for the purpose of clarity and a concise description, features are described herein as part of the same or separate embodiments, however, it will be appreciated that the scope of the invention may include embodiments having combinations of all or some of the features described.

EXAMPLES

Example 1. General Materials and Methods

Generation of Induced Pluripotent Stem Cells
Dermal fibroblasts from control #1 (healthy individual not suffering from Pompe disease) and two patients (#1 and #2) with Pompe disease were obtained via skin biopsy. All patients and controls were negative for HIV, hepatitis B, hepatitis C as tested by quantitative PCR analysis at the diagnostic department of Virology of the Erasmus MC Rotterdam, The Netherlands. Both patient cell lines contain the IVS1 mutation on one allele. The second allele was c.525delT for patient #1, and c.923A>C (his>pro) for patient #2, which both are established pathogenic GAA variants. Primary fibroblasts were reprogrammed into iPS cells using a polycistronic lentiviral vector of Oct4, Sox2, Klf4, and c-Myc as described in Warlich et al., *Mol Ther*, 19:782-789 (2011). iPS control #2 cell line was a gift from Christian Freund and Christine Mummery and has been characterized previously (Dambrot et al., *Differentiation*, 85:101-109 (2013)). iPS cells were cultured on γ-irradiated mouse embryonic feeder (MEF) cells. The culture medium consisted of DMEM/F12 medium (Invitrogen™, Thermo Fisher Scientific Inc., Carlsbad, Calif., USA), 20% knock-out serum replacement (Invitrogen™), 1% non-essential amino acids (Gibco™), 1% penicillin/streptomycin/L-glutamine (100×, Gibco™), 2 mM ß-mercaptoethanol (Invitrogen™) and 20 ng/ml basic fibroblast growth factor (FGF2; Prepotech Inc.).

Immunofluorescence

Cells were fixed with 4% paraformaldehyde (Merck) in PBS for 10 minutes at room temperature, washed with PBS and permeabilized for 5 minutes with 0.1% Triton X-100 (AppliChem) in PBS. Blocking was performed for 45 minutes at room temperature with blocking solution containing PBS-T (0.1% Tween, Sigma) with 3% BSA (Sigma). Primary antibodies (Table 1) were diluted into 0.2% BSA in PBS-T and incubated either 1 hour at room temperature or overnight at 4° C. After incubation wells were washed three times for 5 minutes with PBS-T and incubated with the secondary antibodies (1:500, Alexa-Fluor-594-α-goat, Alexa-Fluor-488-α-mouse, Invitrogen™) in PBS-T for 30 minutes at room temperature. The wells were subsequently washed two times for 5 minutes with PBS and incubated for 15 minutes with Hoechst 33258 (Thermo Scientific). Afterwards cells were embedded in Vectashield Mounting Medium (Vector).

TABLE 1

Antibodies described herein

| Name | Dilution | Supplier |
| --- | --- | --- |
| Goat-α-NANOG | 1:50 | R&D Systems (AF1997) |
| Goat-α-OCT4 | 1:100 | Santa Cruz (sc-8629) |
| Mouse-α-SSEA4 | 1:100 | Millipore (SCR001) |
| Mouse-α-TRA-1-60 | 1:100 | Millipore (SCR001) |
| Mouse-α-TRA-1-81 | 1:100 | Millipore (SCR001) |
| Mouse-α-SMA | 1:50 | Dako (M0851) |
| Mouse-α-AFP | 1:200 | Sigma Aldrich (A8452) |
| Mouse-α-TUJ1 | 1:1000 | Sigma Aldrich (T8660) |
| Mouse-α-MF20 | 1:50 | DSHB |
| Rabbit-α-Myogenin | 1:100 | Santa Cruz (sc-576) |
| Rabbit-α-MyoD | 1:100 | Santa Cruz (sc-304) |
| Mouse-α-Pax7 | 1:100 | DSHB |
| Mouse-α-C-MET-APC | 1:50 | R&D Systems (FAB3582A) |
| Mouse-α-HNK1-FITC | 1:100 | Aviva Systems Biology (OASA02271) |
| Mouse-anti-Titin | 1:50 | DHSB |
| α-Bungarotoxin, biotin-XX conjugate | 1:500 | Thermo Fisher Scientific (B1196) |

Microarray Analysis

RNA samples to be analyzed by microarrays were prepared using RNeasy columns with on-column DNA digestion (Qiagen GmbH, Hilden, Germany). 300 ng of total RNA per sample was used as input into a linear amplification protocol (Ambion®, Thermo Fisher Scientific Inc.), which involved synthesis of T7-linked double-stranded cDNA and 12 hours of in vitro transcription incorporating biotin-labelled nucleotides. Purified and labeled cRNA was then hybridized for 18 h onto HumanHT-12 v4 expression Bead-Chips (Illumina) following the manufacturer's instructions. After recommended washing, chips were stained with streptavidin-Cy3 (GE Healthcare) and scanned using the iScan reader (Illumina) and accompanying software. Samples were exclusively hybridized as biological replicates. The bead intensities were mapped to gene information using BeadStudio 3.2 (Illumina). Background correction was performed using the Affymetrix Robust Multi-array Analysis (RMA) background correction model (Irizarry et al, *Nucleic Acids Res,* 31:e15 (2003)). Variance stabilization was performed using the $\log_2$ scaling and gene expression normalization was calculated with the method implemented in the lumi package of R-Bioconductor. Data post-processing and graphics was performed with in-house developed functions in Matlab. Hierarchical clustering of genes and samples was performed with one minus correlation metric and the unweighted average distance (UPGMA) (also known as group average) linkage method.

In Vitro Differentiation iPS colonies were washed once with PBS and treated for 45 minutes with 1 mg/ml collagenases IV (Invitrogen™, Thermo Fisher Scientific Inc., Carlsbad, Calif., USA) at 37° C., scraped and centrifuged for 15 seconds at 800 rpm. The pellet was slowly dissolved into EB medium (iPS medium without FGF2) with 10 µM of the ROCK inhibitor Y-27632 dihydrochloride (Ascent Scientific Ltd. Bristol, UK) and plated on low binding plates (Cyto one, USA Scientific, Inc., Ocala, Fla., USA). For the endoderm condition 10 µM of the TGF-β inhibitor SB 431542 (Ascent Scientific, Ltd.) was added to the EB medium. Six days later EBs were plated in 12 wells coated with 0.1% gelatin (Sigma-Aldrich Co, St. Louis, Mo., USA/Merck KGaA, Darmstadt, Germany) for endoderm and mesoderm differentiation or with matrigel coated plates for ectoderm differentiation in endo/meso/ectoderm medium (Table 2). Cells were fixed after 14 days of differentiation with 4% paraformaldehyde (Merck KGaA) in PBS for 5 minutes at room temperature and processed for immunofluorescence.

TABLE 2

Composition of in vitro differentiation medium into three germ layer derivatives.

| Medium | Component | Supplier |
| --- | --- | --- |
| Endoderm/Mesoderm | DMEM High Glucose | Gibco |
|  | 20% FBS | Thermo Scientific |
|  | 1% PSG | Gibco |
|  | α-Thioglycerol (4 µl/100 ml) | Sigma Aldrich |
|  | 1x NEAA | PAA |
|  | 0.1% ß-mercaptoethanol | Life Technologies |
| Ectoderm | 50% neurobasal medium | Gibco |
|  | 50% DMEM/F12 | Gibco |
|  | 1% PSG | Gibco |
|  | 0.1% ß-mercaptoethanol | Life Technologies |
|  | 1:500 7.5% BSA fraction V | Gibco |
|  | 1:200 N2 | Gibco |
|  | 1:100 B27 w/o VitA | Gibco |

Karyotype Analysis iPS or myogenic progenitors were detached with TrypLe (Gibco) for 5 minutes at 37° C. The pellet was incubated with 10 µg/ml colcemid (Gibco) for 30 minutes at room temperature. Cells were then centrifuged for 10 minutes at 1100 rpm and resuspended into prewarmed 0.075 M KCL and incubated for 10 minutes at 37° C. After incubation cells were five times washed with fixation solution (3:1 methanol: acetic acid) and spread onto glass slides. Hoechst 33258 staining was performed as described above.

Differentiation of iPS Cells to Myogenic Progenitor Cells

Briefly, 0.6 mm large iPS colonies cultured in 10 cm dishes on MEF feeders were treated for 5 days with 3.5 µM of CHIR99021 (Axon Medchem) in myogenic differentiation medium (DMEM/F12, 1×ITS-X and Penicillin/Streptomycin-Glutamine, all Gibco™). After 5 days, CHIR99021 was removed and cells were cultured in myogenic differentiation medium containing 20 ng/ml FGF2 (Prepotech Inc.) for 14 days and switched for an additional 16 days to myogenic differentiation medium only. Fusion index represent the % of nuclei inside myofibers relative to the total number of nuclei. Five random fields at 20× magnification were counted.

FACS Sorting

Cells were washed once with PBS, detached for 5 minutes with TrypLe (Gibco™) at 37° C., and filtered through a 0.45 µM FACS strainer (Falcon). Cells were stained with HNK-1-FITC (1:100, Aviva Systems Biology) and C-MET-APC (1:50, R&D Systems) for 30 minutes on ice in myogenic differentiation medium and washed three times with ice-cold 0.1% BSA in PBS before FACS sorting. Hoechst (33258, Life Technologies) was used as viability marker.

Expansion of Myogenic Progenitor Cells

Hoechst 33258/C-MET-positive cells were plated at 40,000 cells/well on extracellular matrix (ECM) (E6909 Sigma Aldrich)-coated 48 wells plates in iPS-myogenic progenitor proliferation medium containing DMEM high glucose (Gibco™) supplemented with 100 U/ml Penicillin/Streptomycin/Glutamine (Life Technologies), 10% fetal bovine serum (Hyclone, Thermo Scientific), 100 ng/ml FGF2 (Prepotech Inc.), and 1× RevitaCell™ Supplement (Gibco™). Cells were passaged using 2× diluted TrypLe. For differentiation to skeletal muscle cells, myogenic progenitors were grown to 90% confluence and the medium was then replaced with myogenic differentiation medium (see above).

Modification of the U7 snRNA Vector for Intermediate Throughput Cloning of AON Sequences The U7 snRNA gene and promoter was amplified by PCR from female mouse genomic DNA using Fw-ms-U7snRNA-Pst1 and Rv-ms-U7snRNA-Sall primers, which included Pst1 and Sall overhang restriction sites. The PCR fragment (425 bp) was cloned into a pCRII-TOPO vector according to the manufacture's manual (Invitrogen™). SMopt and NsiI sites were generated by site-directed mutagenesis according to an inner and outer primer design with Fw- and Rv-U7snRNA-SmOPT or Fw- and Rv-U7snRNA-NsiI as inner primers and with Fw-M13 and Rv-M13 as outer primers (Supplementary Table 3), and subcloned using the PstI and Sall sites in front of the polypurine tract fragment of the lentiviral vector used for reprogramming from which OSKM and the SF promoter were removed.

The nucleotide sequences described herein, and their use in medicine, are an aspect of the invention.

Supplementary table 3
Primers used for qRT-PCR, RT-PCR and Clonging

| Primer target | Sequence (5'-3') |
| --- | --- |
| β-Actin fw | AACCGCGAGAAGATGACCC |
| β-Actin rv | GCCAGAGGCGTACAGGGATAG |
| GAA Exon 1-2 fw | AAACTGAGGCACGGAGCG |
| GAA Exon 1-2 rev | GAGTGCAGCGGTTGCCAA |
| GAA Cryptic Exon 2 fw | GGCACGGAGCGGGACA |
| GAA Cryptic Exon 2 rev | CTGTTAGCTGGATCTTTGATCGTG |
| GAA Full Skip Exon 2 fw | AGGCACGGAGCGGATCA |
| GAA Full Skip Exon 2 rev | TCGGAGAACTCCACGCTGTA |
| MyoD fw | CACTCCGGTCCCAAATGTAG |
| MyoD rv | TTCCCTGTAGCACCACACAC |
| Myog fw | CACTCCCTCACCTCCATCGT |
| Myog rev | CATCTGGGAAGGCCACAGA |
| LAMP1 fw | GTGTTAGTGGCACCCAGGTC |
| LAMP1 fv | GGAAGGCCTGTCTTGTTCAC |
| LAMP2 fw | CCTGGATTGCGAATTTTACC |
| LAMP2 rv | ATGGAATTCTGATGGCCAAA |
| Fw-U7snRNA-smOPT | GCTCTTTTAGAATTTTGGAGCAGGTTTTCTGACTTCG |
| Rv-U7snRNA-smOPT | CGAAGTCAGAAAACCTGCTCCAAAAATTCTAAAAGAGC |
| Fw-U7snRNA-NsiI | CCTGGCTCGCTACAGATGCATAGGAGGACGGAGGACG |
| Rv-U7snRNA-NsiI | CGTCCTCCGTCCTCCTATGCATCTGTAGCGAGCCAGG |
| Fw-M13 | GTAAAACGACGGGCCAG |
| Rv-M13 | CAGGAAACAGCTATGAC |
| GAA Exon1-3 fw | AGGTTCTCCTCGTCCGCCCGTTGTTCA |

Supplementary table 3
Primers used for qRT-PCR, RT-PCR and Clonging

| Primer target | Sequence (5'-3') |
|---|---|
| GAA Exon1-3 rv | TCCAAGGGCACCTCGTAGCGCCTGTTA |
| Fw-ms-U7snRNA-PstI | GCGCCTGCAGTAACAACATAGGAGCTGTG |
| Rv-ms-U7snRNA-PstI | GCGCGTCGACCAGATACGCGTTTCCTAGGA |

Cloning of AONs into the U7 snRNA Vector

AONs were inserted via PCR amplification using a forward primer that contained the desired antisense sequence and the unique NsiI restriction site and the reverse primer Rv-ms-U7snRNA-SalI. The amplified PCR product was purified by agarose gel electrophorese, extracted (gel extraction kit, Qiagen), digested with NsiI and SalI, purified (PCR purification kit, Qiagen), and cloned into the NsiI and SalI sites of the U7 snRNA vector. Clones were verified by sequencing with the Fw-ms-U7snRNAPstI (Supplementary Table 3) and restriction enzyme digestion.

Cell Culture

HEK293T cells or human primary fibroblasts were cultured in Dulbecco's Modified Eagle's Medium (DMEM) high glucose (Gibco™) supplemented with 100 U/ml Penicillin/Streptomycin/Glutamine (Gibco™) and 10% Fetal bovine serum (Hyclone, Thermo Scientific). Cells were passaged after reaching 80/90% confluence with TrypLE (Gibco™).

Virus Production

Lentiviruses were produced by co-transfecting HEK293T cells at 80% confluency in a 10 cm culture dish with the lentivirus transfer vector (3 µg SF-OSKM or SF-U7snRNA vectors) and packaging plasmids (2 µg psPAX2 and 1 µg pVSV vectors) using Fugene 6 transfection according to manufacturer's protocol (Promega). Lentiviruses were harvested from the medium after 72 hours of transfection and filtered using a 0.45 µm PDFV filter (Milipore). After filtering, lentiviruses were concentrated by high speed centrifugation for 2 hours at 20000 rpm in a Beckman Coulter Ultracentrifuge with SW32 Ti rotor at 4° C. The supernatant was removed and the pellet was dissolved in 25 µl Dulbecco's Modified Eagle's medium Low Glucose (Invitrogen™) per plate and stored in aliquots at −80° C.

P24 ELISA

Viral titers were determined with the HIV-1 p24 antigen ELISA kit (Retrotek) according to manufacturer's manual. Each virus was diluted 1:40000 and 1:100000 and the OD450 nm was measured with a varioskan (Thermos Scientific) reader.

Transduction of U7 snRNA Vectors

One day before infection $6 \times 10^4$ cells of primary fibroblasts derived from patient #1 were seeded per single well of a 12-wells plate. One day later the cells were infected with 200 ng virus containing the SF-U7snRNA constructs, and after 24 hours cells were washed three times with PBS before adding fresh medium. After 4 days cells were washed with PBS and harvested with RLT buffer of the RNAeasy kit for RNA isolation (Qiagen). For GAA enzyme activity assay, cells were harvested after 12 days.

Morpholino Transfections

Human fibroblasts or myogenic progenitors (day 0 of differentiation) were transfected with morpholino AONs using Endoporter reagent (Gene-Tools, LLC). Cells were plated out and grown to 90% confluency before transfection. Endoporter was used at a concentration of 4,5 µl per ml of medium. Morpholino AON's were dissolved in sterile water to a concentration of 1 mM and the appropriate volume was added to each culture well. Cells were harvested after 3 to 5 days in culture.

RNA Isolation and cDNA Synthesis

RNA was extracted with the RNeasy mini kit with Dnase treatment (Qiagen) and was stored at −80° C. in RNase-free water. cDNA was synthesized from 500 ng RNA using iScript cDNA synthesis kit (Bio-Rad).

qPCR cDNA was diluted five, ten or twenty times and used with 7.5 µl iTaq Universal SYBR Green Supermix (Bio-Rad) and 10 pmol/µl forward and reverse primers (Supplementary Table 3) in a CFX96 real-time system (Bio-Rad). Ct values were related to amounts using standard curves of 4-6 dilutions.

Flanking Exon RT-PCR

Ten times diluted cDNA with GC GAA Exon1-3 fw and GC GAA Exon1-3 ry primers were used for RT-PCR with the Advantage GC 2 PCR kit (Clontech) and a GC-melt concentration of 0.5 M according to manufacturer's protocol. The whole GC-PCR reaction was analyzed on a 1.5% agarose gel containing 0.5 µg/ml ethidium bromide (Sigma).

GAA Enzyme Activity Assay

Cells were harvested with ice cold lysis buffer (50 mM Tris (pH 7.5), 100 mM NaCl, 50 mM NaF, 1% Triton X-100 and one tablet Protease Inhibitor Cocktail (cOmplete, with EDTA, Roche) and incubated for 10 minutes on ice. Samples were centrifuged at 14000 rpm for 10 minutes at 4° C. GAA enzyme activity was measured using 4-methylumbelliferyl α-D-glucopyranoside (Sigma) as substrate as described in Kroos et al., Neurology, 68:110-115, (2007). Total protein concentration was determined using a BCA protein assay kit (Pierce, Thermo Scientific).

Statistical Analysis

All data represent mean+/−SD, and p-values refer to two-sided t-tests. Bonferroni multiple testing correction was applied where necessary. A p-value <0.05 was considered to be significant.

Figure 1:
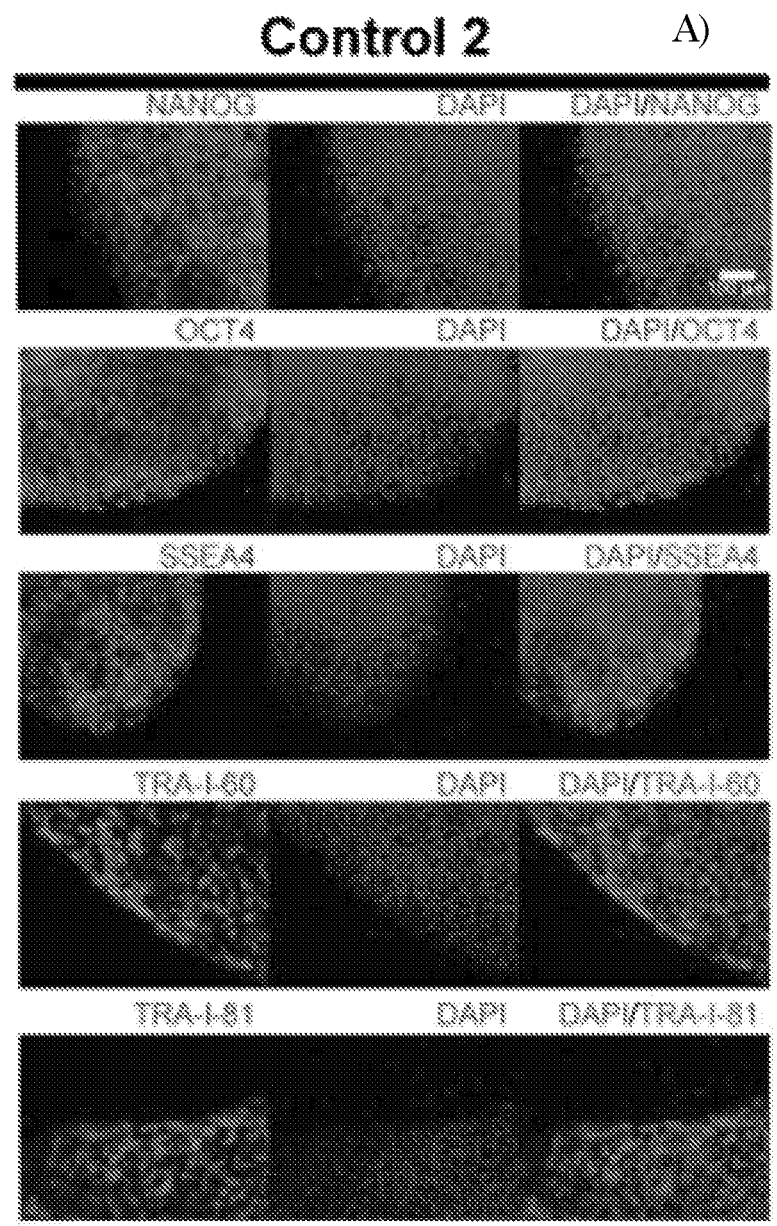
FIG. 1 shows in panels A-C the characterization of iPS cell lines used in this study. The characterization of iPS cells of control #1 (not shown) was previously published (Dambrot et al., *Differentiation* 85:101-109 (2013)). Panel A shows an immunofluorescent analysis of iPS cells from control #2 and Pompe disease patients #1 and #2 as labeled with antibodies against Nanog, Oct4, SSEA4, TRA-1-60 and TRA-1-81 (red). DAPI was used to stain nuclei (blue). All three lines expressed pluripotency markers Nanog, Oct4, SSEA4, TRA-1-60 and TRA-1-81.
Figure 1:
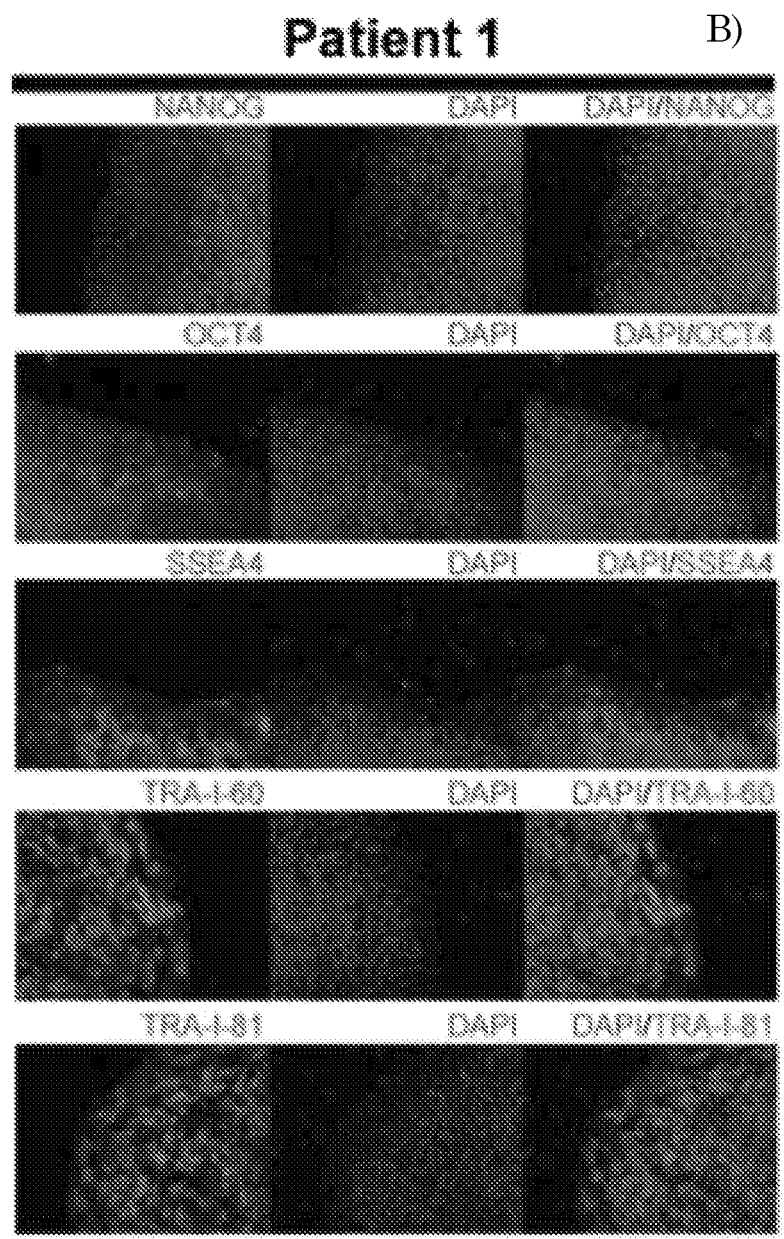
Figure 1:
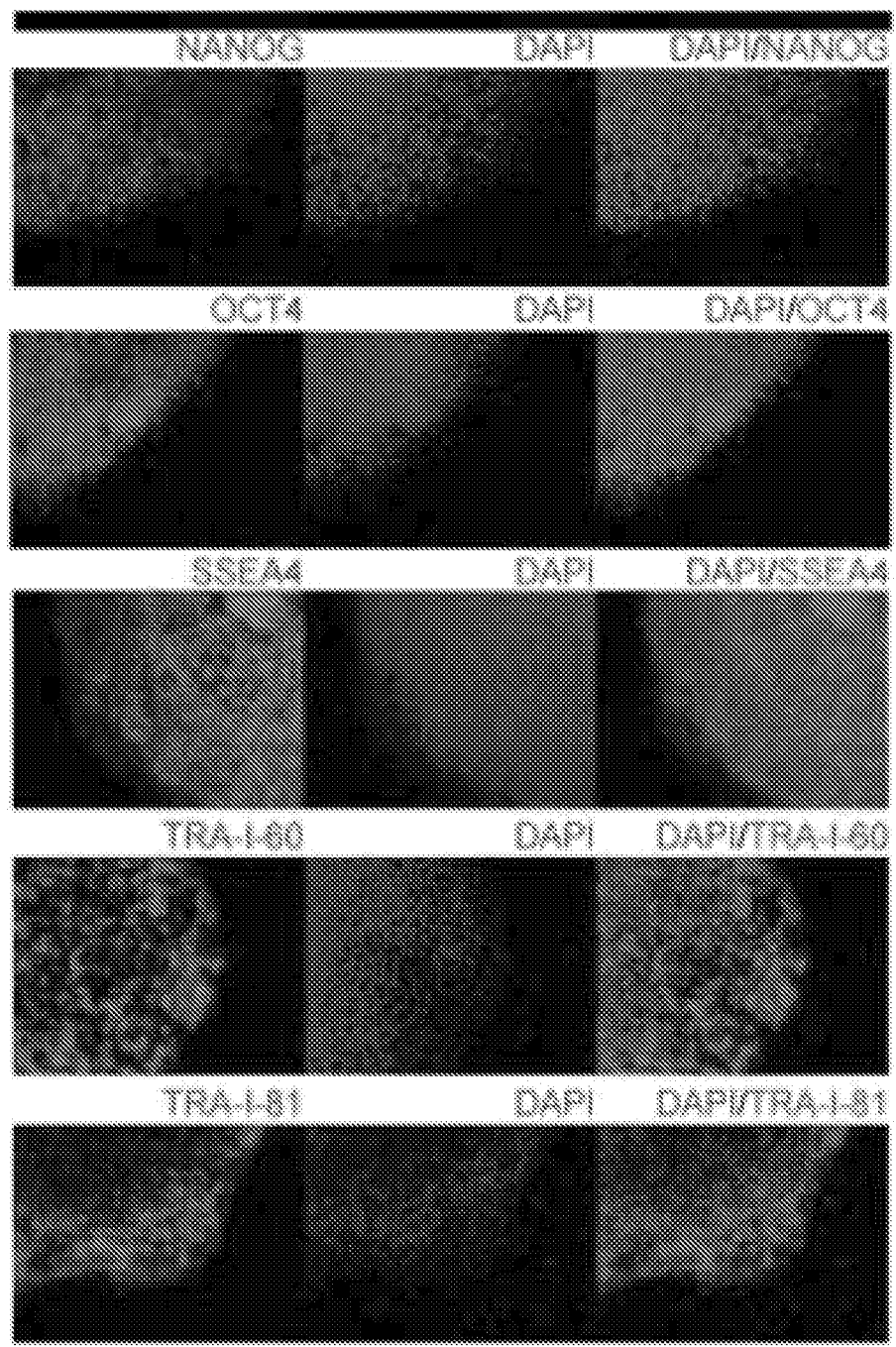
Figure 2:
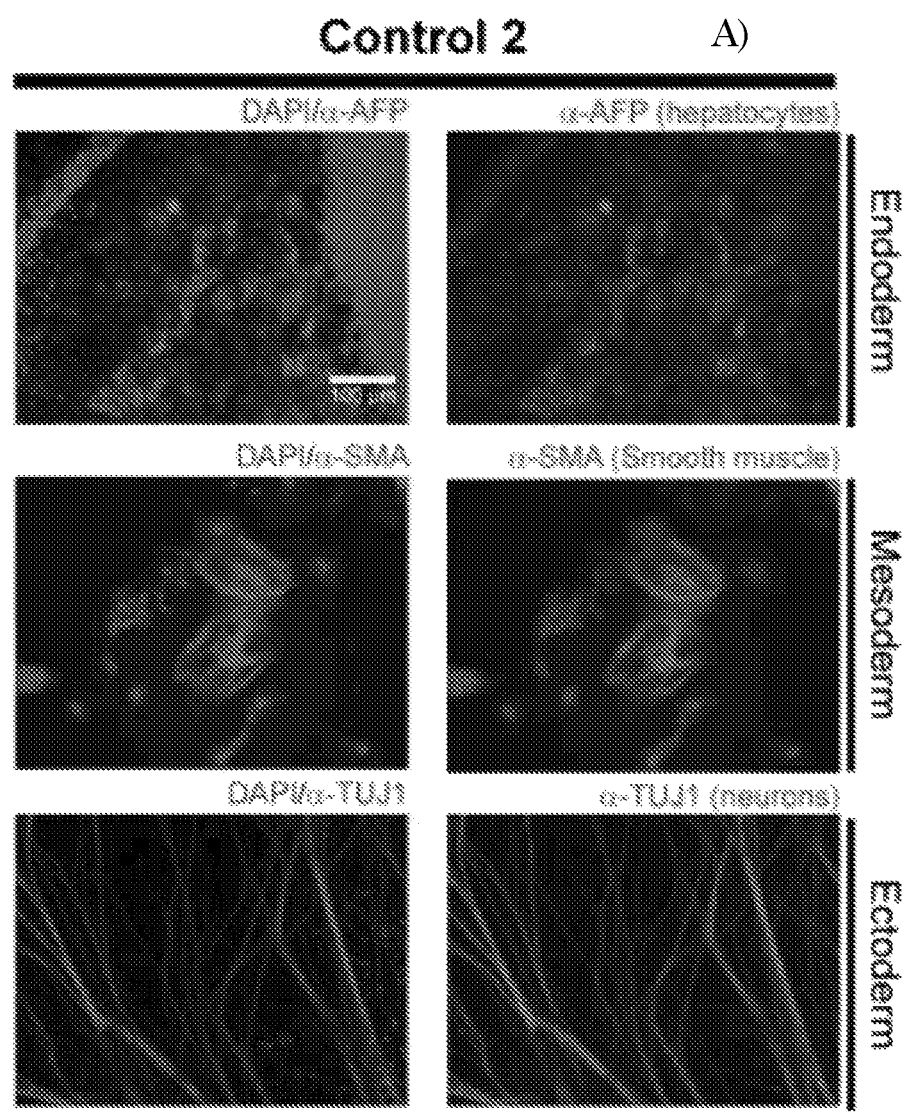
FIG. 2 shows in panels A-C the in vitro differentiation potential of the iPS lines of FIG. 1 into cell-types of the three germ layers. Stainings for alpha-Fetoprotein (AFP) show hepatocytes (endoderm; red), stainings for smooth muscle actin (SMA) show smooth muscle cells (mesoderm; red), and neuron-specific class III beta-tubulin (TUJ1) stainings show neurons (ectoderm; red). DAPI staining shows nuclei in blue.
Figure 2:
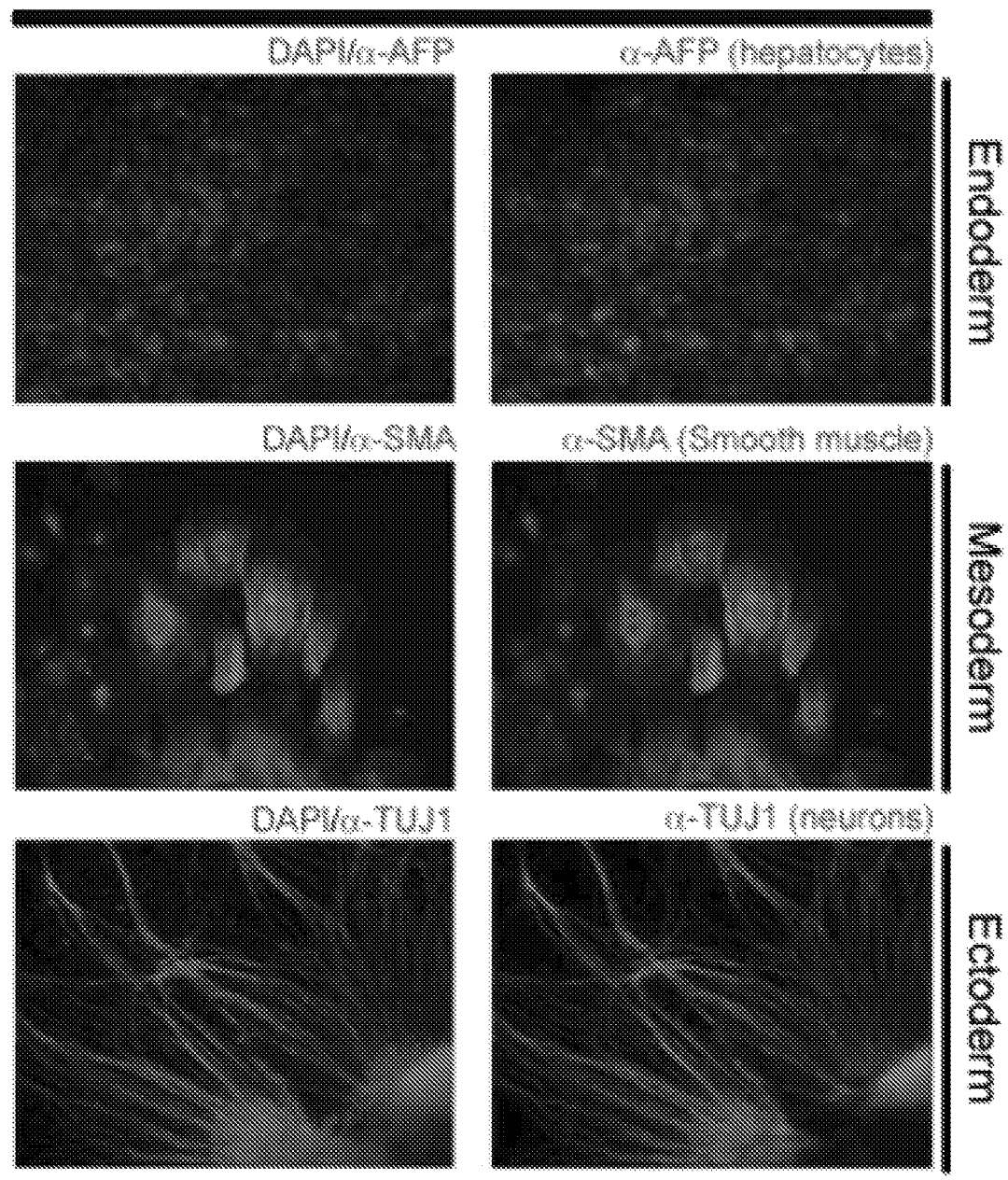
Figure 2:
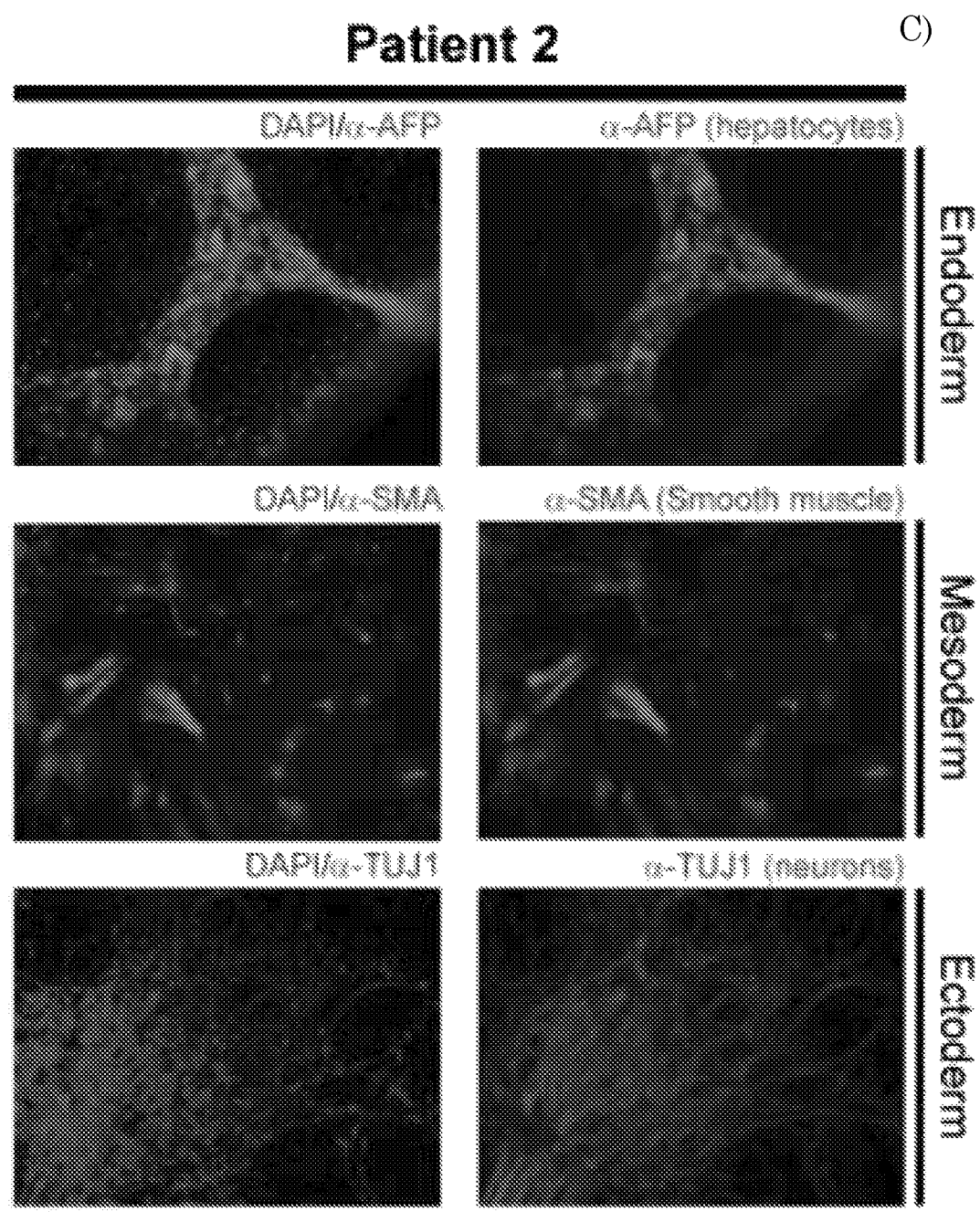
Figure 4:
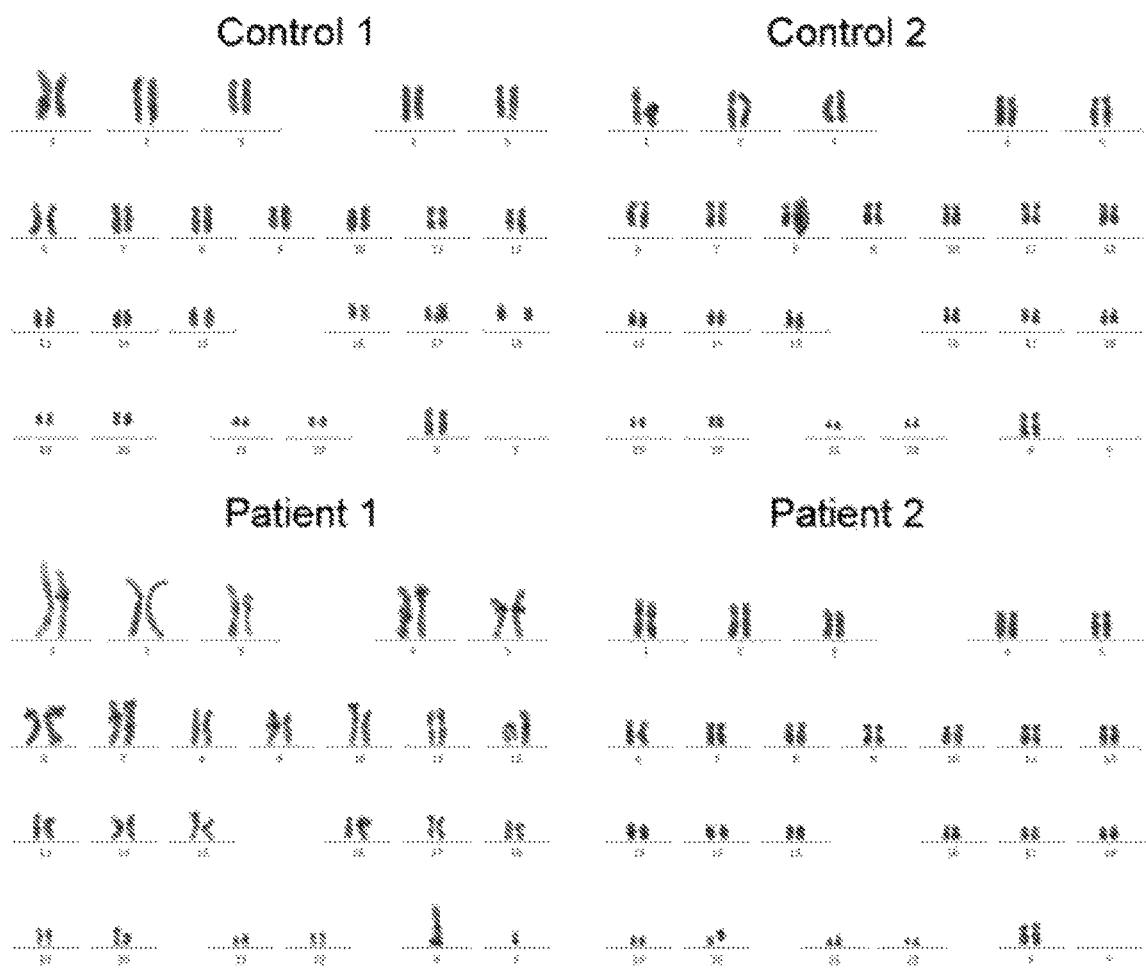
FIG. 4 shows a karyotype analysis of the four iPS lines used in this study (patient #1, patient #2, control #1 and control #2). All lines have normal karyotypes. Representative karyotypes of 10 nuclei per cell line are shown.

Example 2. Generation and Characterization of iPS Cells from Adult Pompe Patients Carrying the IVS1 GAA Variant To model childhood/adult onset Pompe disease, primary fibroblasts were reprogrammed into iPS cells using a polycistronic lentiviral vector of Oct4, Sox2, Klf4, and c-Myc. Two patients were modelled. In patient #1 (IVS1, c.525delT), the mRNA from the c.525delT allele is degraded, facilitating detection of splicing forms from the IVS1 allele. In patient #2 (IVS1, c.923A>C), the c.923A>C allele mRNA is expressed. Fibroblasts from a healthy control were also reprogrammed; a second, independent healthy control has been described previously (Dambrot et al., 2013 as mentioned hereinbefore). All three lines expressed pluripotency markers including NANOG, OCT4, SSEA4, TRA-1-81 and TRA-1-60 (FIG. 1), were capable of differentiating into cell-types of the three germ layers (FIG. 2), and showed expression of essential pluripotent genes comparable to hES lines H1 and H9 and reduction of expression of fibroblast-associated genes (FIG. 3). In addition, the iPS cells contained normal karyotypes (FIG. 4).

Example 3. Differentiation of iPS Cells into Skeletal Muscle Cells Via Expandable Myogenic Progenitors To differentiate iPS cells into skeletal muscle cells, available transgene-dependent protocols were tested with limited success due to low yields, low expression of transgenes, and/or variability between clones. We therefore developed a transgene-free protocol (FIG. 5A). Initial experiments resulted in Pax7-positive cells after a 35 day period, however, with low reproducibility in our hands. We then tested modifications and found that treatment with a higher concentration of CHIR99021 (3.5 µM) for a longer duration (5-6 days) was well tolerated and resulted in the generation of Pax7-positive cells in more than 35 independent differentiation experiments (FIG. 5B), although yields still varied considerably. Pax7-positive cells were purified by FACS using CMet+/Hnk1−. These could be differentiated into multinucleated myotubes within 5-9 days (FIG. 5C). Typical yields were low with 250,000 purified cells derived from $10^6$ iPS cells. To improve the yields and robustness of myogenic differentiation, expansion of purified muscle cells was tested. Basic DMEM supplemented with 10% FBS and 100 ng/ml FGF2 (as specified in the Examples hereinbefore) was supportive of myogenic progenitor proliferation and resulted in an expansion of at least $7 \times 10^6$ fold in 15 passages (FIG. 6A). While expression of Pax7 diminished at increasing passage number (early passages (p0-5): 1-30% pax7-positive cells; late passages (p7-15): 0-2% pax7-positive cells), MyoD remained expressed in virtually all cells during the entire expansion period (FIG. 6C). Expanded cells showed efficient and homogenous differentiation into multinucleated myotubes that expressed nuclear Myogenin and Myosin Heavy Chain (MHC) (FIG. 6D). Differentiation efficiencies remained similar throughout the expansion phase as indicated by similar fusion indexes (FIG. 6E). Cryopreservation of the expanded culture was possible at any moment and yielded high viabilities upon thawing. The karyotype remained normal at passage 16 (FIG. 6F). Myogenic progenitors from all four iPS lines showed reproducible capacity to expand and to differentiate into the myogenic lineage, as judged from MHC expression. This now enabled the use of these lines for drug testing and disease modeling.

Example 4. Identification of Repressors of GAA Exon 2 Inclusion

Splicing products from the IVS1 GAA variant include wild type GAA mRNA (N) caused by leaky normal splicing, partial skipping of exon 2 caused by utilization of a cryptic splice site in exon 2 (SV3), and full skipping of exon 2 (SV2) (Boerkoel et al., Am J Hum Genet, 56:887-897 (1995); Huie et al., Hum Mol Genet, 3:2231-2236 (1994); Dardis et al., Nucleic Acids Res, 42:1291-1302 (2014); and Bergsma et al., Hum Mutat, 36:57-68 (2015)). These products were identified by flanking exon RT-PCR in primary fibroblasts from patients (FIG. 7A). Splicing is subject to regulation by exonic or intronic splicing silencer (ESS, ISS) or splicing enhancer sequences (ESE, ISE) (FIG. 7B). We reasoned that it may be possible to promote exon 2 inclusion by inhibition of a splicing silencer element using an AON. To identify such putative splicing silencer, in silico predictions were performed which resulted in algorithm-dependent putative silencer and enhancer elements (data not shown here) without indicating an obvious candidate silencer element that could be amenable to inhibition by an AON. Therefore an unbiased screen was performed using a tiling array of U7 snRNAs-expressed AONs (FIG. 7C). The original U7 snRNA vector (Gorman et al., Proc Natl Acad Sci USA, 95:4929-4934 (1998)) was adapted to enable one-step cloning of an AON and intermediate throughput screening. In control experiments in fibroblasts of patient #1, a U7 snRNA-based AON targeting the splice sites of exon 4 of the cyclophilin A (CypA) pre-mRNA was capable of inducing skipping of exon 4. This confirmed previous reports (Liu et al., Nucleic Acids Res, 32:3752-3759 (2004)) and demonstrated that the modified U7 snRNA construct can be used to modulate splicing. Application of the screen to primary fibroblasts derived from adult onset Pompe patient #1 resulted in the identification of a number of snRNAs that modulated inclusion of exon 2 in the GAA mRNA, as shown with RT qPCR (FIG. 7D, black (darkest) line) and RT-PCR (FIG. 7E)) analysis. Importantly, snRNAs targeting two regions in intron 1, at c.-32-179 and c.-32-219, promoted inclusion of exon 2. Exclusion of exon 2 was promoted by snRNAs that targeted regions in the 5' part of exon 2. Promotion and inhibition of exon 2 inclusion resulted in increased and decreased GAA enzymatic activity, respectively (FIG. 7D, compare black (darkest) and red (lightest) lines). The lentiviral amount tested (200 ng) appeared to yield an optimal ratio between biological effect and nonspecific reduction of cell viability and GAA expression seen at high viral amounts (data not shown here). A microwalk was performed around the regions c.-32-179 and c.-32-219 with 2 nt difference (FIG. 7F). This showed that the found locations were peak values, while two additional snRNAs were identified that promoted exon 2 inclusion when targeted to c.-32-182 and c.-32-184 (FIG. 7G-H)). Taken together, the U7-based snRNA screen of intron 1 and exon 2 identified regions potentially involved in repression of GAA exon 2 inclusion.

Example 5. Blockage of Splicing Repressor Sequences Using Antisense Oligonucleotides Next, morpholino-based AONs were designed that targeted the two major putative repressor sequences at c.-32-219 (AONs 1 and 2) and c.-32-179 (AONs 3 and 4)(FIGS. 8A-B)). As control, two phosphorodiamidate morpholino oligomer (PMO)-based AONs were used that target the 3' donor splice site of exon 4 in the CypA pre-mRNA (FIGS. 8B-C) and these were able to promote skipping of exon 4 and exons 3+4 after transfection into primary fibroblasts (data not shown here). Next the GAA targeting AONs 1-4 were tested in primary fibroblasts from patient #1. RT-qPCR analysis of exon 2 inclusion showed that AONs 3 and 4 promoted exon 2 inclusion more than 2 fold, whereas AONs 1 and 2 were ineffective (FIG. 9A). Concomitant effects on GAA enzymatic activity were found, with more than two-fold enhancement by AON 3 and 4, while AONs 1 and 2 were ineffective. Effects of AON 3 and 4 were almost maximal at 2 µM AON and reached a maximum at 5-20 µM (FIGS. 9B-C). These results were confirmed in a fibroblast cell line from patient #2 (data not shown here). Based on our experience with diagnosing more than 600 patients in our reference center for Pompe disease, a two-fold increase in GAA enzyme activity in IVS1 patients (who typically have 10-15% of normal control activity) alleviates the disease and converts patients to the normal range. We therefore conclude that AONs 3 and 4 restore GAA exon 2 splicing in IVS1 cells to sufficient levels to alleviate the disease. To confirm that AONs enhanced GAA enzymatic activity via splicing rather than total gene expression, we analyzed individual splicing products. Of note, full skip (SV2) and cryptic splicing transcripts (SV3) lack the translation start codon and are subject to mRNA degradation. Semi-quantitative RT-PCR analysis showed that in IVS1 patients, AON 4 treatment increased the amount of full-length (N) transcript, while the amount of full skip (SV2) transcript was reduced (FIG. 9D). The amount of cryptic splicing transcript SV3 remained unchanged. AON 4 had no effect on GAA expression in control cells. RT-qPCR utilizing splicing product-specific primers (Bergsma et al., *Hum Mutat* 36:57-68 (2015)) confirmed this (FIG. 9E). This shows that AON 4 promoted exon 2 inclusion in the context of the IVS1 variant.

Example 6. Splicing Modulation in iPS-Derived Myotubes

To test the effect of the IVS1 variant in skeletal muscle cells (which was unknown so far), iPS cell-derived myotubes were analyzed. Flanking exon RT-PCR analysis showed a similar effect compared to fibroblasts (FIG. 10A). Products from myotubes at the position of the splicing products N, SV2, and SV3 were sequenced and found to be identical to their counterparts in fibroblasts (data not shown here). Control myotubes did not show obvious aberrant GAA pre-mRNA splicing. RT-qPCR showed that the wild type splicing product N was expressed to slightly higher levels in control myotubes, but to slightly lower levels in Pompe myotubes compared to fibroblasts (FIG. 10B). The SV3 product was slightly higher in Pompe myotubes compared to Pompe fibroblasts. To test whether AONs 3 and 4 promote exon inclusion in skeletal muscle cells, patient-derived myotubes obtained from expanding purified myogenic progenitors were used (FIG. 10C-D). FIG. 10E shows the impact of AON 3 on GAA exon 2 splicing in myotubes from patient #1, as analyzed by RT-PCR. AON 3 caused a concentration-dependent increase in exon 2 inclusion, as judged from the increase in the amounts of the wild type variant (N) and a concomitant decrease in the amounts of the partial (SV3) and full exon 2 skip (SV2) variants. This was confirmed by RT-qPCR with primers specific for individual splicing variants in myotubes from patient #1 treated with AON 3 (FIG. 10F) and AON 4 (FIG. 10G) and in myotubes from patient #2 treated with AON 3 and AON 4 (data not shown). No effect of AONs 3 and 4 on GAA expression and exon 2 splicing was observed in myotubes from control iPS cells (FIG. 10H). Importantly, AON 3 and 4 enhanced GAA enzymatic activity in myotubes derived from patient #1 (FIG. 10I) and patient #2 (data not shown), and was ineffective in myotubes from control #1 (FIG. 10J) and control #2 (data not shown here). To test possible toxic effects of AON treatment on myotube morphology and marker gene expression, immunofluorescence and RT-qPCR analysis were used. No toxic effects of the transfection itself, AON 3 or 4 on MHC or myogenin expression was observed using immunofluorescence (FIGS. 4C-D). RT-qPCR analysis showed no consistent changes in expression of MyoD, Myog, LAMP1 or LAMP2. Taken together, the AONs 3 and 4 corrected aberrant GAA exon 2 splicing in patient-derived myotubes. Importantly, AONs 3 and 4 treatment raised the GAA enzyme activity to levels above the disease threshold, offering a potential therapy for the childhood and adult onset from of Pompe disease.

Example 7. Maturation of Myotubes

This example illustrates the options for using the cells of the invention as disease models. Using such myotube models, the effect of a disease on the maturation may be assessed, including the assessment of the expression of maturation markers, and the formation of sarcomeres. Since also the acetylcholine receptor is expressed, the cells can be used to assess calcium signaling and allow for the testing of contractility.

Long-Term Differentiation

Myogenic progenitors were plated with 50,000 cells into a 24 well either coated with extracellular matrix (ECM) (E6909 Sigma Aldrich) (30 minutes R/T 1:200 in myogenic progenitor medium (expansion medium)) or a 1:1 mixture of 2.5% Collagen Type I rat tail (Millipore) in PBS with 1% MaxGel™ ECM (E0282 Sigma Aldrich) in DMEM coated overnight at room temperature. Plating medium consisted of DMEM high glucose (Gibco) supplemented with 100 U/ml Penicillin/Streptomycin/Glutamine (Life Technologies), 4% Ultroser G (pall) and 100 ng/ml FGF2 (Prepotech Inc.). When myogenic progenitors reached 90% confluence the medium was replaced with long term myogenic differentiation medium consisting of DMEM high glucose (Gibco™) supplemented with 100 U/ml Penicillin/Streptomycin/Glutamine (Life Technologies) with 1% ITS-X and 1% knockout serum replacement (Invitrogen™). Every second day 50% of the medium was replaced by fresh differentiation medium. This medium, and its use in the differentiation of cells of this invention, are aspects of the invention.

Example 8. Expression Profile of Expanded Cells

Control 1 and Control 2 MPCs were expanded for 8 passages in proliferation condition as described previously (van der Wal et al., 2017). RNA was extracted using the RNeasy minikit with DNAse step (Qiagen, Germantown, Md.). RNase-free water was used to elute RNA which was stored at −80° C. Sequencing libraries were prepared using TruSeq Stranded mRNA Library Prep Kit (Illumina, San Diego, Calif., USA) according to the manufacturer's instructions. These libraries were sequenced on an HiSeq2500 sequencer (Illumina, San Diego, Calif., USA) in rapid run mode according to the manufacturer's instructions. Reads were generated of 50 base-pairs in length. Reads were mapped to hg38 using the Tuxedo pipeline and the FPKM was calculated (Pertea et al., 2016). Genes with a FPKM of <5 were removed. FPKM from control 1 and control 2 were averaged. Publically available datasets from Choi et al. (GSM1824045, GSM1824046 and GSM1824047) were downloaded and samples were averaged (Choi et al., 2016). The genes described in Table 1 of Biressi et al. were selected in our dataset and from Choi et al and ranked according to expression level (Biressi et al., 2007).

TABLE 4

List of genes expressed in Choi et al but not in van der Wal et al. For description of the analysis, see text to FIG. 16

ARX
CD34
CITED1
FGF4
FGF5
FGF6
FGF9
FOXC1
ITGA9
LAMA4
MEOX1
SEMA3D
SEMA4G
SMAD6
TCF15
UNCX

REFERENCES

Biressi, S., Tagliafico, E., Lamorte, G., Monteverde, S., Tenedini, E., Roncaglia, E., Ferrari, S., Ferrari, S., Cusella-De Angelis, M. G., Tajbakhsh, S., et al. (2007). Intrinsic phenotypic diversity of embryonic and fetal myoblasts is revealed by genome-wide gene expression analysis on purified cells. Dev Biol 304, 633-651.

Choi, I. Y., Lim, H., Estrellas, K., Mula, J., Cohen, T. V., Zhang, Y., Donnelly, C. J., Richard, J. P., Kim, Y. J., Kim, H., et al. (2016). Concordant but Varied Phenotypes among Duchenne Muscular Dystrophy Patient-Specific Myoblasts Derived using a Human iPSC-Based Model. Cell Rep 15, 2301-2312.

Pertea, M., Kim, D., Pertea, G. M., Leek, J. T., and Salzberg, S. L. (2016). Transcript-level expression analysis of RNA-seq experiments with HISAT, StringTie and Ballgown. Nat Protoc 11, 1650-1667.

van der Wal, E., Bergsma, A. J., van Gestel, T. J. M., in't Groen, S. L. M., Zaehres, H., Araúzo-Bravo, M. J., Schöler, H. R., van der Ploeg, A. T., and Pijnappel, W. W. M. P. (2017). GAA Deficiency in Pompe Disease Is Alleviated by Exon Inclusion in iPSC-Derived Skeletal Muscle Cells. Molecular Therapy—Nucleic Acids 7, 101-115.

The invention claimed is:

1. A method for producing a cell culture comprising a population of expanded myogenic progenitor cells in a synthetic culture medium, comprising the steps of:
  a) providing a pluripotent stem cell (PSC);
  b) culturing said PSC in a synthetic culture medium supporting differentiation of said PSC towards a myogenic cell lineage for (i) a first period of 3-8 days in the presence of between 2-5 microM of CHIR99021, (ii) a second period of 5-20 days in the presence of 10-30 ng/ml of FGF2; and, optionally, (iii) a third period of 10-20 days in the presence of insulin-transferrin-selenium-ethanolamine (ITS-X), to thereby provide a cell culture of pre-differentiated PSCs comprising myogenic progenitors cells;
  c) isolating from said cell culture comprising myogenic progenitors cells at least one C-Met+ and Hnk1− myogenic progenitor starting cell, to thereby provide a purified myogenic cell lineage;
  d) expanding said at least one isolated C-Met+ and Hnk1− myogenic progenitor starting cell in a synthetic culture medium comprising fetal bovine serum (FBS), and 90-110 ng/ml of FGF2 for at least 1 passage to thereby provide a cell culture comprising a population of expanded C-Met+ and Hnk1− myogenic progenitor cells, wherein at least 50% of said population of expanded C-Met+ and Hnk1− myogenic progenitor cells are myogenesis marker MyoD positive and myogenesis marker Pax7 negative.

2. The method of claim 1, wherein the step of expanding said at least one C-Met+ and Hnk1− myogenic progenitor starting cell in step d) is performed in a culture medium comprising a ROCK inhibitor during at least the cultivation prior to the first passage.

3. A cell culture comprising a population of expanded myogenic progenitor cells in a synthetic culture medium, obtained by a method comprising the steps of:
  a) providing a pluripotent stem cell (PSC);
  b) culturing said PSC in a synthetic culture medium supporting differentiation of said PSC towards a myogenic cell lineage for (i) a first period of 3-8 days in the presence of between 2-5 microM of CHIR99021, (ii) a second period of 5-20 days in the presence of 10-30 ng/ml of FGF2; and, optionally, (iii) a third period of 10-20 days in the presence of insulin-transferrin-selenium-ethanolamine (ITS-X), to thereby provide a cell culture of pre-differentiated PSCs comprising myogenic progenitors cells;
  c) isolating from said cell culture comprising myogenic progenitors cells at least one C-Met+ and Hnk1− myogenic progenitor starting cell to thereby provide a purified myogenic cell lineage;

d) expanding said at least one isolated C-Met+ and Hnk1– myogenic progenitor starting cell in a synthetic culture medium comprising fetal bovine serum (FBS) and 90-110 ng/ml of FGF2 for at least 1 passage to thereby provide a cell culture comprising a population of expanded C-Met+ and Hnk1– myogenic progenitor cells, wherein at least 50% of said population of expanded C-Met+ and Hnk1– myogenic progenitor cells are myogenesis marker MyoD positive and myogenesis marker Pax7 negative.

4. The cell culture of claim 3, wherein the step of expanding said at least one C-Met+ and Hnk1– myogenic progenitor starting cell in step d) is performed in a culture medium comprising a ROCK inhibitor during at least the cultivation prior to the first passage.

5. The cell culture of claim 3, wherein said population of expanded myogenic progenitor cells is homogeneous.

6. The cell culture of claim 3, wherein expanded myogenic progenitor cells in said culture medium are expandable in vitro and inducible to terminal differentiation into myotubes and/or myofibers.

7. The cell culture of claim 3, wherein the culture is frozen or cryopreserved.

8. The method according to claim 1, wherein the PSC is an iPSC.

9. The method according to claim 1, wherein in step d) said at least one isolated C-Met+ and Hnk1– myogenic progenitor starting cell is expanded in the synthetic culture medium comprising FBS and 90-110 ng/ml of FGF2 for at least 7 passages.

10. The method according to claim 1, wherein at least 90% of said population of expanded C-Met+ and Hnk1– myogenic progenitor cells are myogenesis marker MyoD positive and myogenesis marker Pax7 negative.

11. The method according to claim 2, wherein the culture medium base is DMEM-HG.

12. The cell culture of claim 3, wherein the PSC is an iPSC.

13. The cell culture of claim 3, wherein in step d) said at least one isolated C-Met+ and Hnk1– myogenic progenitor starting cell is expanded in the synthetic culture medium comprising FBS and 90-110 ng/ml of FGF2 for at least 7 passages.

14. The cell culture of claim 3, wherein at least 90% of said population of expanded C-Met+ and Hnk1– myogenic progenitor cells are myogenesis marker MyoD positive and myogenesis marker Pax7 negative.

15. The cell culture of claim 4, wherein the culture medium base is DMEM-HG.

16. The method of claim 1 wherein said synthetic culture medium in step d) comprises about 100 ng/ml of FGF2.

* * * * *